US009056076B2

(12) United States Patent
Deschatelets et al.

(10) Patent No.: US 9,056,076 B2
(45) Date of Patent: *Jun. 16, 2015

(54) METHOD OF TREATING AGE-RELATED MACULAR DEGENERATION COMPRISING ADMINISTERING A COMPSTATIN ANALOG

(75) Inventors: Pascal Deschatelets, Louisville, KY (US); Paul Olson, Louisville, KY (US); Cedric Francois, Louisville, KY (US)

(73) Assignee: Potentia Pharmaceuticals, Inc., Crestwood, KY (US)

( * ) Notice: Subject to any disclaimer, the term of this patent is extended or adjusted under 35 U.S.C. 154(b) by 19 days.

This patent is subject to a terminal disclaimer.

(21) Appl. No.: 13/409,941

(22) Filed: Mar. 1, 2012

(65) Prior Publication Data

US 2013/0296254 A1    Nov. 7, 2013

Related U.S. Application Data

(63) Continuation of application No. 11/544,389, filed on Oct. 6, 2006, now Pat. No. 8,168,584.

(60) Provisional application No. 60/725,484, filed on Oct. 8, 2005, provisional application No. 60/726,447, filed on Oct. 12, 2005, provisional application No. 60/760,974, filed on Jan. 19, 2006.

(51) Int. Cl.
| | |
|---|---|
| *A61K 38/12* | (2006.01) |
| *A61K 38/10* | (2006.01) |
| *A61K 9/00* | (2006.01) |
| *A61K 31/00* | (2006.01) |
| *A61K 38/08* | (2006.01) |
| *A61K 38/17* | (2006.01) |
| *A61F 9/00* | (2006.01) |

(52) U.S. Cl.
CPC .............. *A61K 38/12* (2013.01); *A61F 9/0008* (2013.01); *A61K 9/0051* (2013.01); *A61K 31/00* (2013.01); *A61K 38/08* (2013.01); *A61K 38/10* (2013.01); *A61K 38/17* (2013.01)

(58) Field of Classification Search
CPC .......... A61K 38/08; A61K 38/10; A61K 9/00
USPC ................. 514/21.1, 21.5, 21.6, 20.8
See application file for complete search history.

(56) References Cited

U.S. PATENT DOCUMENTS

| | | | |
|---|---|---|---|
| 4,299,838 | A | 11/1981 | Durlach |
| 4,576,750 | A | 3/1986 | Pitzenberger |
| 4,816,567 | A | 3/1989 | Cabilly et al. |
| 4,870,097 | A | 9/1989 | Makovec et al. |
| 5,157,110 | A | 10/1992 | Kotwal et al. |
| 5,482,135 | A | 1/1996 | Phillips et al. |
| 5,492,135 | A | 2/1996 | DeVore et al. |
| 5,632,984 | A | 5/1997 | Wong et al. |
| 5,770,589 | A | 6/1998 | Billson et al. |
| 5,776,970 | A | 7/1998 | Shechter et al. |
| 5,797,898 | A | 8/1998 | Santini, Jr. et al. |
| 5,824,072 | A | 10/1998 | Wong |
| 5,844,099 | A | 12/1998 | Stahl et al. |
| 5,861,486 | A | 1/1999 | Devore et al. |
| 5,869,079 | A | 2/1999 | Wong et al. |
| 5,942,405 | A | 8/1999 | Ames et al. |
| 6,051,698 | A | 4/2000 | Janjic et al. |
| 6,129,761 | A | 10/2000 | Hubbell |
| 6,140,472 | A | 10/2000 | Rosengard et al. |
| 6,169,057 | B1 | 1/2001 | Lovatt |
| 6,197,934 | B1 | 3/2001 | DeVore et al. |
| 6,204,365 | B1 | 3/2001 | Devore et al. |
| 6,214,790 | B1 | 4/2001 | Richelson et al. |
| 6,319,897 | B1 | 11/2001 | Lambris et al. |
| 6,331,313 | B1 | 12/2001 | Wong et al. |
| 6,378,526 | B1 | 4/2002 | Bowman et al. |
| 6,436,427 | B1 | 8/2002 | Hammang et al. |
| 6,534,058 | B2 | 3/2003 | Fung et al. |
| 6,551,595 | B1 | 4/2003 | Rosengard et al. |
| 6,582,959 | B2 | 6/2003 | Kim |
| 6,692,759 | B1 | 2/2004 | Wong et al. |
| 6,818,447 | B1 | 11/2004 | Pavco et al. |

(Continued)

FOREIGN PATENT DOCUMENTS

| | | |
|---|---|---|
| EP | 0737484 A2 | 10/1996 |
| JP | 11-197234 | 7/1999 |

(Continued)

OTHER PUBLICATIONS

Fung, A.E. et al., An Optical Coherence Tomography-Guided, Variable Dosing Regimen with Intravitreal Ranibizumab (Lucentis) for Neovascular Age-related Macular Degeneration, Am. J. Ophthalmol., 143:566-583 (2007).

Morikis, D. et al., The Structural Basis of Compstatin Activity Examined by Structure-Function-based Design of Peptide Analogs and NMR, J. Biol. Chem., 277(17):14942-14953 (2002).

Ricklin, D. et al., Complement—a key system for immune surveillance and homeostasis, Nat. Immunol., 11(9):785-797 (2010).

Soulika, et al., Compstatin Inhibits Complement Activation by Binding to the Beta-Chain of Complement Factor 3, Mol. Immunol., 43:2023-2029 (2006).

Acosta, J. et al. "Complement and complement regulatory proteins as potential molecular targets for vascular diseases," Curr Pharm Des. (2004) 10(2):203-11, Bentham Science Publishers Ltd., Bussum, the Netherlands.

(Continued)

*Primary Examiner* — Gyan Chandra
(74) *Attorney, Agent, or Firm* — Choate, Hall & Stewart, LLP; Brenda Herschbach Jarrell

(57) ABSTRACT

The present invention features the use of compstatin and complement inhibiting analogs thereof for treating and/or preventing age related macular degeneration and other conditions involving macular degeneration, choroidal neovascularization, and/or retinal neovascularization. The invention also provides compositions comprising compstatin or a complement inhibiting analog thereof and a second therapeutic agent. The invention also provides compositions comprising compstatin or a complement inhibiting analog thereof and a gel-forming material, e.g., soluble collagen, and methods of administering the compositions.

19 Claims, 5 Drawing Sheets

(56) References Cited

U.S. PATENT DOCUMENTS

| | | |
|---|---|---|
| 6,821,950 B1 | 11/2004 | Fairlie et al. |
| 6,897,290 B1 | 5/2005 | Atkinson et al. |
| 6,976,982 B2 | 12/2005 | Santini, Jr. et al. |
| 7,084,106 B1 | 8/2006 | Kotwal et al. |
| 7,108,982 B1 | 9/2006 | Hageman |
| 7,112,327 B2 | 9/2006 | Fung et al. |
| 7,745,389 B2 | 6/2010 | Hageman |
| 7,989,589 B2 | 8/2011 | Lambris |
| 2002/0086356 A1 | 7/2002 | Tuschl et al. |
| 2002/0102581 A1 | 8/2002 | Hageman et al. |
| 2003/0017501 A1 | 1/2003 | Hageman et al. |
| 2003/0171320 A1 | 9/2003 | Guyer |
| 2003/0175950 A1 | 9/2003 | McSwiggen |
| 2003/0191084 A1 | 10/2003 | Biesecker et al. |
| 2003/0207309 A1 | 11/2003 | Hageman et al. |
| 2004/0018176 A1 | 1/2004 | Tolentino et al. |
| 2004/0038869 A1 | 2/2004 | Finney et al. |
| 2004/0092470 A1 | 5/2004 | Leonard et al. |
| 2004/0115774 A1 | 6/2004 | Kochendoerfer et al. |
| 2004/0177387 A1 | 9/2004 | Jayakrishna |
| 2004/0229266 A1 | 11/2004 | Tuschl et al. |
| 2005/0020525 A1 | 1/2005 | McSwiggen et al. |
| 2005/0032733 A1 | 2/2005 | McSwiggen et al. |
| 2005/0048099 A1 | 3/2005 | Shiah et al. |
| 2005/0054596 A1 | 3/2005 | McSwiggen et al. |
| 2005/0090448 A1 | 4/2005 | Johnson et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0260198 A1 | 11/2005 | Holers et al. |
| 2005/0281861 A1 | 12/2005 | Hughes et al. |
| 2005/0287601 A1 | 12/2005 | Hageman et al. |
| 2006/0002852 A1 | 1/2006 | Salzman et al. |
| 2006/0002971 A1 | 1/2006 | Salzman et al. |
| 2006/0105980 A1 | 5/2006 | Benedict et al. |
| 2006/0115476 A1 | 6/2006 | Tedesco et al. |
| 2006/0140939 A1 | 6/2006 | Fung |
| 2006/0142191 A1 | 6/2006 | Francois et al. |
| 2006/0257359 A1 | 11/2006 | Francois et al. |
| 2006/0263819 A1 | 11/2006 | Hageman et al. |
| 2007/0020647 A1 | 1/2007 | Hageman et al. |
| 2007/0065433 A1 | 3/2007 | Mollnes et al. |
| 2007/0149616 A1 | 6/2007 | Clark et al. |
| 2007/0196367 A1 | 8/2007 | Dinu |
| 2007/0238654 A1 | 10/2007 | Deschatelets et al. |
| 2008/0075755 A1 | 3/2008 | Deschatelets et al. |
| 2011/0182877 A1 | 7/2011 | Francois et al. |

FOREIGN PATENT DOCUMENTS

| | | |
|---|---|---|
| JP | 2004-065461 A | 3/2004 |
| WO | WO-96/30046 A1 | 10/1996 |
| WO | WO-97/33603 | 9/1997 |
| WO | WO-99/13899 | 3/1999 |
| WO | WO-00/47130 | 8/2000 |
| WO | WO-01/84149 | 11/2001 |
| WO | WO-02/11793 A1 | 2/2002 |
| WO | WO-03/047633 | 6/2003 |
| WO | WO-03/086448 | 10/2003 |
| WO | WO-2004/026326 A2 | 4/2004 |
| WO | WO-2004/026328 | 4/2004 |
| WO | WO-2004/037310 | 5/2004 |
| WO | WO-2004/041160 | 5/2004 |
| WO | WO-2005/110435 A1 | 11/2005 |
| WO | WO-2005/110436 | 11/2005 |
| WO | WO-2006/080951 | 3/2006 |
| WO | WO-2006/042329 | 4/2006 |
| WO | WO-2006062716 | 6/2006 |
| WO | WO-2006099330 | 9/2006 |
| WO | WO-2007/062249 | 5/2007 |
| WO | WO-2007/076437 | 5/2007 |
| WO | WO-2007056227 | 5/2007 |
| WO | WO-2007084765 | 7/2007 |

OTHER PUBLICATIONS

Acosta, J. et al. "Molecular basis for a link between complement and the vascular complications of diabetes," Proc. Nat. Acad. Sci. (2000) 97(10):5450, National Academies of Science, Washington, DC.

Ambati, J. et al. "Age-related macular degeneration: etiology, pathogenesis, and therapeutic strategies." Survey of Ophthalmology (2003) 48(3):257-293, Elsevier Inc., Amsterdam, the Netherlands.

American Academy of Ophthalmology. "Age-Related Macular Degeneration, Preferred Practice Pattern." (2006) American Academy of Ophthalmology, San Francisco, CA.

Anderson, DH, et al. A role for local inflammation in the formation of drusen in the aging eye. Am J Ophthalmol (2002) 134:411-431.

Bourges, J.-L. et al. "Ocular drug delivery targeting the retina and retinal pigement epithelium using polylactide nanoparticles." Investigative Ophthalmology and Visual Sciences (2003) 44(8):3562-3569, Association for Research in Vision and Ophthalmology, Rockville, MD.

Bora, PS, et al. "Role of complement system in choroidal neovascularization". Invest Ophthalmol Vis Sci (2002) 43: E-Abstract 1291. Association for Research in Vision and Ophthalmology, Rockville, MD.

Bora, PS, et al. "Complement Activation is Required in the Murine Model of Laser-induced Choroidal Neovascularization" Invest Ophthalmol Vis Sci (2003) 44: E-Abstract 3940. Association for Research in Vision and Ophthalmology, Rockville, MD.

Bora, PS et al. "Neovascularization in a mouse model that simulates exudative macular degeneration is complement dependent." Invest Ophthalmol Vis Sci (2004) 45: E-Abstract 1871. Association for Research in Vision and Ophthalmology, Rockville, MD.

Bora, PS et al. Complement activation by alternative pathway is critical in the development of laser-induced choroidal neovascularization. Invest Ophthalmol Vis Sci (2006) 47: E-Abstract 4167. Association for Research in Vision and Ophthalmology, Rockville, MD.

Bora, PS et al.: "Role of complement and complement membrane attack complex in neovascularization," Journal of Immunology (2005) 174 (1): 491-497, American Association of Immunologists, Bethesda, MD.

Braun, J. Daily Nexus (2003) vol. 83, Issue 135, pp. 1-5.

Conley YP, et al. Candidate gene analysis suggests a role for fatty acid biosynthesis and regulation of the complement system in the etiology of age-related maculopathy. Hum Mol Genet (2005) 14:1991-2002.

Davenport, R.J. Sci. Aging Knowl. Environ. (2004) vol. 2004, Issue 37, p. nf85.

Donoso, L. et al. "The role of inflammation in the pathogenesis of age-related macular degeneration," Survey of Ophthalmology (2006) 51(2):137-152, Elsevier Inc., Amsterdam, the Netherlands.

Edwards, AO et al. "Complement Factor H Polymorphism and Age-Related Macular Degeneration," Science (2005) 308(5720):421-424, American Association for the Advancement of Science, Washington, DC.

Gaudreault, J. et al. "Preclinical pharmacokinetics of Ranibizumab (rhuFabV2) after a single intravitreal administration." Investigative Ophthalmology and Visual Science (2005) 46(2):726-733, Association for Research in Vison and Ophthalmology, Rockville, MD.

Gerl, V et al. "Extensive Deposits of Complement C3d and C5b-9 in the Choriocapillaris of Eyes of Patients with Diabetic Retinopathy," Investigative Ophthalmology and Visual Sciences, (2002) 43(4):1104-1108, Association for Research in Vision and Ophthalmology, Rockville, MD.

Gold, B. et al. "Variation in factor B (BF) and complement component 2 (C2) genes is associated with age-related macular degeneration," Nature Genetics, (2006) 38: 458-462, Nature Publishing Group, New York, NY.

Hageman, GS et al. "An integrated hypothesis that considers drusen as biomarkers of immune-mediated processes at the RPE-Bruch's membrane interface in aging and age-related macular degeneration," Progress in Retinal and Eye Research, (2001) 20(6):705-732, Elsevier Ltd., Amsterdam, the Netherlands.

Hageman, GS et al. "A common haplotype in the complement regulatory gene factor H (HF1/CFH) predisposes individuals to age-

(56) References Cited

OTHER PUBLICATIONS related macular degeneration," Proceedings of the National Academy of Sciences (2005) 102(20):7053-7054, National Academy of Sciences, Washington, DC.
Haines, JL et al. "Complement factor H variant increases the risk of age-related macular degeneration," Science (2005) 308(5720):419-421, American Association for the Advancement of Science, Washington, DC.
Holland, MCH, et al., "Synthetic small-molecule complement inhibitors", Curr. Op. Invest. Drugs (2004) 5(11) 1164-1173. The Thomson Corporation.
Hughes et al. "A common CFH haplotype, with deletion of CFHR1 and CFHR3, is associated with lower risk of age-related macular degeneration," Nature Genetics (2006) 38(10):1173-1177, Nature Publishing Group, New York, NY.
Hrynchak, PK, et al. Optometry and Vision Science (2000), vol. 77, No. 7, pp. 347-356. American Academy of Optometry.
International Search Report for International Patent Application No. PCT/US06/039397 dated Oct. 24, 2007.
Jaffe, G. "Safety and pharmacokinetics of an intraocular fluocinolone acetonide sustained delivery device," Investigative Ophthalmology and Visual Sciences, (2000) 41(11): 3569-3575, Association for Research in Vision and Ophthalmology, Rockville, MD.
Johnson, L V et al.: "Complement activation and inflamatory processes in drusen formation and age related macular degeneration," Experimental Eye Research (2001) 73(6):887-896, Academic Press Ltd., London, GB.
Jha, P. et al. "The complement system plays a critical role in the development of experimental autoimmune anterior uveitis," Investigative Ophthalmology and Visual Sciences, (2006)47(3): 1030-1038, Association for Research in Vision and Ophthalmology, Rockville, MD.
Katragadda et al.: "Expression of compstatin in *Escherichia coli*: Incorporation of unnatural amino acids enhances its activity," Protein Expression and Purification (2006) 47 (1):289-295, Academic Press, San Diego, CA.
Katragadda et al. "Hydrophobic effect and hydrogen bonds account for the improved activity of a complement inhibitor, compstatin," Journal of Medicinal Chemistry (2006) 49 (15):4616-4622, American Chemical Society, Washington, DC.
Katragadda et al.: "Structure-activity-based design of potent compstatin analogs," Molecular Immunology (2006) 44(1-3):192, Elsevier, Elmsford, NY.
Katragadda et al. "Thermodynamic studies on the interaction of the third complement component and its inhibitor, compstatin," Journal of Biological Chemistry, (2004) 279(53):54987-54995, American Society for Biochemistry and Molecular Biology, Bethesda, MD.
Klein, RJ et al. "Complement Factor H Polymorphism in Age-Related Macular Degeneration," Science (2005) 308(5720):385-389, American Association for the Advancement of Science, Washington, DC.
Li, M. et al. "CFH haplotypes without the Y402H coding variant show strong association with susceptibility to age-related macular degeneration," Nature Genetics (2006) 38(9):1049-1054, Nature Publishing Group, New York, NY.
Magnusson, KP, et al. "CFH Y402H Confers Similar Risk of Soft Drusen and Both Forms of Advanced AMD." PLoS Med 2006;3:e5.
Makrides, SC et al. "Therapeutic inhibition of the complement system," Pharmacological Reviews (1998) 50(1):59-87, American Society for Pharmacology and Experimental Therapeutics, Bethesda, MD.
Maller, J. et al. "Common variation in three genes, including a noncoding variant in CFH, strongly influences risk of age-related macular degeneration," Nature Genetics (2006) 38(9):1055-1059, Nature Publishing Group, New York, NY.
Mallik, B et al.: "Design and NMR characterization of active analogues of compstatin containing non-natural amino acids," Journal of Medicinal Chemistry (2005) 48 (1):274-286.

Midena, E., et al. "Macular function impairment in eyes with early age-related macular degeneration." Invest. Ophthalmol. Vis. Sci. (1997), vol. 38, pp. 467-477. Association for Research in Vision and Ophthalmology, Rockville, MD.
Morikis, D et al.: "Improvement of the anti-C3 activity of compstatin using rational and combinatorial approaches," Biochemical Society Transactions (2004) 32 (1): 28-32, Biochemical Society, London, UK.
Nozaki, M. et al. "Drusen complement components C3a and C5a promote choroidal neovascularization." Proc Natl Acad Sci U S A (2006) 103:2328-2333. National Academies of Science, Washington, DC.
Sahu, A., et al. Binding kinetics, structure-activity relationship, and biotransformation of the complement inhibitor compstatin. J Immunol. (2000)165(5).2491-9. The American Association of Immunologists, Bethesda, MD.
Sahu, A, et al. "Compstatin, a peptide inhibitor of complement, exhibits species-specific binding to complement component C3" Mol Immunol. (2003) 39(10):557-66. Elsevier, Elmsford, NY.
Sepp, T. et al. "Complement Factor H Variant Y402H is a Major Risk Determinant for Geographic Atrophy and Choroidal Neovascularization in Smokers and Nonsmokers." Invest Ophthalmol Vis Sci (2006) 47:536-540. Association for Research in Vision and Ophthalmology, Rockville, MD.
Sivaprasad, S. and Chong, NV. The complement system and age-related macular degeneration. Eye (2006), 20: 867-872. The Nature Publishing Group, New York, NY.
Soulika, AM, et al. "Studies of structure-activity relations of complement inhibitor compstatin" J Immunol. (2003) 171(4):1881-90. The American Association of Immunologists, Bethesda, MD.
Written Opinion of the International Searching Authority for International Application No. PCT/US06/039397 dated Aug. 11, 2007.
Yates J.R.W. et al., "Complement C3 variant and the risk of age-related macular degeneration", N Engl J Med., (2007) 357(6):553-61. Massachusetts Medical Society.
Yannuzzi, L. et al. "Retinal angiomatous proliferation in age-related macular degeneration," Retina (2001) 21 (5): 416-34, Lippincott Williams & Wilkins, Hagerstown, MD.
Zareparsi, S, et al. Strong association of the Y402H variant in complement factor H at 1q32 with susceptibility to age-related macular degeneration. Am J Hum Genet (2005) 77:149-153. The American Society of Human Genetics.
Zhang et al. "Early complement activation and decreased levels of glycosylphosphatidylinositol-anchored complement inhibitors in human and experimental diabetic retinopathy" Diabetes (2002) 51(12):3499-3504, American Diabetes Association, Washington, DC.
Zhou, J, et al. "Complement activation by photooxidation products of A2E, a lipofuscin constituent of the retinal pigment epithelium." Proc Natl Acad Sci U S A (2006) 103:16182-16187. National Academies of Science, Washington, DC.
Zhou et al, "Complement Activation by Bisretinoid Constituents of RPE Lipofusion", Ophthalmol. Vis. Sci., 50:1392-1399 (2009).
Jager et al., "Age-Related Macular Degeneration", N. Engl. J. Med., 358:2606-2617 (2008).
Ng et al., Targeting Angiogenesis, the Underlying Disorder in Neovascular Age-Related Macular Degeneration, Canadian Journal of Ophthalmology, 40(3): 352-368 (2005).
Database BIOSIS on STN, BIOSIS, (Philadelphila, PA, USA), DN: PREV200600053073, & Raisler, B.J. et al., Drusen Complement Components C3a and C5a Promote Choroidal Neovascularization, IOVS, 2005, vol. 46, No. Suppl, p. 1214.
Albrecht, J.C. and Fleckenstein, B., New Member of the Multigene Family of Complement Control Proteins in Herpes Saimiri, Journal of Virology, 66(6):3937-3940 (1992).
Albrecht, J.C. et al., Herpesvirus Siamiri Has a Gene Specifying a Homologue of the Cellular Membrane Glycoprotein CD59, Virology, 190(1):527-530 (1992).
Allen, T.M., Ligand-Targeted Therapeutics in Anticancer Therapy, Nature Reviews Cancer, 2(10):750-765 (2002).
Altschul, S.F. et al., Basic local alignment search tool, Journal of Molecular Biology, 215(3):403-410 (1990).

(56) References Cited

OTHER PUBLICATIONS

Altschul, S.F., Gapped BLAST and PSI-BLAST: a New Generation of Protein Database Search Programs, Nucleic Acids Research, 25(17):3389-3402 (1997).
Ambati, J. et al., An Animal Model of Age-Related Macular Degeneration in Senescent CcI-2- or Ccr-2-Deficient Mice, Nature Medicine, 9(11):1390-1397 (2003).
Babitzke, P. and Yanofsky, C., Structural Features of L-Tryptophan Required for Activation of TRAP, the trp RNA-Binding Attenuation Protein of Bacillus subtilis, Journal of Biological Chemistry, 270(21):12452-12456 (1995).
Barlett, J.B. et al., The Evolution of Thalidomide and its IMiD Derivatives as Anticancer Agents, Nature Reviews Cancer, 4(4):314-322 (2004).
Beene, D.L. et al., Cation-πInteractions in Ligand Recognition by Serotonergic (5-HT3A) and Nicotinic Acetylcholine Receptors: The Anomalous Binding Properties of Nicotine, Biochemistry, 41(32):10262-10269 (2002).
Bora, P.S. et al., Immunotherapy for Choroidal Neovascularization in a Laser-Induced Mouse Model Simulating Exudative (Wet) Macular Degeneration, Proceedings of the National Academy of Science, 100(5):2679-2684 (2003).
Chapple, J.P. et al., Unfolding retinal dystrophies: a role for molecular chaperones?, Trends in Mol. Med., 7: 414-421 (2001).
Eguchi, M. And Kahn, M., Design, Synthesis, and Application of Peptide Secondary Structure Mimetics, Mini Reviews in Medicinal Chemistry, 2(5):447-462 (2002).
Einmahl, S. et al., Evaluation of a Novel Biomaterial in the Suprachoroidal Space of the Rabbit Eye, Investigative Ophthalmology and Visual Science, 43(5):1533-1539 (2002).
Ferrara, N., Vascular Endothelial Growth Factor: Basic Science and Clinical Progress, Endocrine Reviews, 25(4):581-611 (2004).
Fish et al., Anti-vascular Endothelial Growth Factor Therapy for Subfoveal Choroidal Neovascularization Secondary to Age-related Macular Degeneration, Phase II Stufy Results, The Eyetech Study Group, Ophthalmology, 110: 978-986 (2003).
Gonzales, N.R. et al., Minimizing the Immunogenicity of Antibodies for Clinical Application, Tumour Biology, 26(1):31-43 (2005).
Gragoudas et al., Pegaptanib for Neovascular Age-Related Macular Degeneration, NE J Med., 351(27): 2805-2816 (2004).
Hanes, J. and Plückthun, A., In Vitro Selection and Evolution of Functional Proteins by Using Ribosome Display, Proceedings of the National Academy of Science, 94(10):4937-4947 (1997).
International Search Report from PCT/US2007/001649 (Mar. 31, 2008).
Internet Citation: URL:http://www.rsinewsrxreportingfrom.com/content.asp?myid+40&tid=365> Anti-VEGF Agents Useful in Age-Related Macular Degeneration, Am Acad of Ophthalm, (Oct., 15, 2005).
Ishida, T. et al., A Combinational Approach to Producing Sterically Stabilized (Stealth) Immunoliposomal Drugs, FEBS Letters, 460(1):129-133 (1999).
Kalayoglu, M.V., Emerging Treatment Strategies for Age-related Macular Degeneration, Internet Citation, URL: <www.medcompare.com/spotlight.asp?spotlightid=62> (retreived Jun. 30, 2004).
Karlin, S. and Altschul, S.F., Applications and Statistics for Multiple High-Scoring Segments in Molecular Sequences, Proceedings of the National Academy of Science, 90(12):5873-5877 (1993).
Karlin, S. and Altschul, S.F., Methods for Assessing the Statistical Significance of Molecular Sequence Features by Using General Scoring Schemes, Proceedings of the National Academy of Science, 87(6):2264-2268 (1990).
Keam, S.J. et al., Verteporfin, A Review of its Use in the Management of Subfoveal Chorodial Neovascularisation, Drugs, 63: 2521-2554 (2003).
Kent, S., Total Chemical Synthesis of Enzymes, Journal of Peptide Science, 9(9):574-593 (2003).
Kohler, G. and Milstein, C., Continuous Cultures of Fused Cells Secreting Antibody of Predetermined Specificity, Nature, 256(5517): 495-497 (1975).
Lippinvott Co., Anti-Vascular Endothelial Growth Factor Therapy for Subfoveal choroidal Neovascularization Secondary to Age-Related Macular Degeneration: Phase II Study Results, Opthal., 110(5): 979-986 (2003).
Michels, S. and Rosenfeld, P.J., Treatment of Neovascular Age-Related Macular Degeneration With Ranibizumab/Lucentis, Klin Monbl Augenheikd, 222(6): 480-484 (2005).
Miller, C.G., The Cowpox Virus-Encoded Homolog of the Vaccinia Virus Complement Control Protein is an Inflammation Modulatory Protein, Virology, 229(1):129-133 (1997).
Novina, C.D. and Sharp, P.A., The RNAi Revolution, Nature, 430(6996):161-164 (2004).
Rakoczy, P.E. et al., Progressive Age-Related Changes Similar to Age-Related Macular Degeneration in a Transgenic Mouse Model, American Journal of Pathology, 161(4):1515-1524 (2002).
Reid, K.B. and Day, A.J., Structure-Function Relationships of the Complement Components, Immunology Today, 10(6):177-180 (1989).
Rosenfeld et al., URL: http://www.revophth.com/index.asp-?page+1_857.htm> An Update on Bevacizumab (Dec. 1, 2005).
Rosengard, A.M. et al., Variola Virus Immune Evasion Design: Expression of a Highly Efficient Inhibitor of Human Complement, Proceedings of the National Academy of Science, 99(13):8803-8813 (2002).
Sahu, A. et al., Interaction of Vaccinia Virus Complement Control Protein with Human Complement Proteins: Factor I-Mediated Degradation of C3b to iC3b1 Inactivates the Alternative Complement Pathway, Journal of Immunology, 160(11): 5596-5604 (1998).
Scullica, L. and Benedetto, F., Diagnosis and classification of macular degenerations: an approach based on retinal function testings, Documenta Ophthalmologica, 102: 237-250 (2001).
Smith, S.S. et al., Conserved Surface-Exposed K/R-X-K/R Motifs and Net Positive Charge on Provirus Complement Control Proteins Serve as Putative Heparin Binding Sites and Contribute to Inhibition of Molecular Interactions with Human Endothelial Cells: a Novel Mechanism for Evasion of Host Defense, Journal of Virology, 74(12):5659-5666 (2000).
Tamai, K. et al., Lipid Hydroperoxide Stimulates Subretinal Choroidal Neovascularization in the Rabbit, Experimental Eye Research, 74(2):301-308 (2002).
Tezel, T.H. et al., Pathogenesis of Age-Related Macular Degeneration, Trends in Molecular Medicine, 10(9):417-420 (2004).
Torchilin, V.P. et al., p-Nitrophenylcarbonyl-PEG-PE-Liposomes: Fast and Simple Attachment of Specific Ligands, Including Monoclonal Antibodies, to Distal Ends of PEG Chains Via p-Nitrophenylcarbonyl Groups, Biochimica Biophysica Acta, 1511(2):497-522 (2001).
Uvarova, E.A. and Shchelkunov, S.N., Species-specific Differences in the Structure of Orthopoxvirus Complement-Binding Protein, Virus Research, 81(1-2):39-45 (2001).
Wang, F. et al., AAV-Mediated Expression of Vascular Endothelial Growth Factor Induces Choroidal Neovascularization in Rat, Investigative Ophthalmology and Visual Science, 44(2):781-790 (2003).
Winter, G. et al., Making Antibody by Phage Display Technology, Annual Reviews in Immunology, 12:433-455 (1994).
Written Opinion for PCT/US2007/001649, 9 pages (Mar. 31, 2008).
Zacks, D.N. et al., Verteporfin Photodynamic Therapy in the Rat Model of Choroidal Neovascularization: Angiographic and Histologic Characterization, Investigative Ophthalmology and Visual Science, 43(7):2384-2391 (2002).

METHOD OF TREATING AGE-RELATED MACULAR DEGENERATION COMPRISING ADMINISTERING A COMPSTATIN ANALOG

CROSS-REFERENCE TO RELATED APPLICATIONS

This application is a continuation of application Ser. No. 11/544,389, filed Oct. 6, 2006, which claims priority to and the benefit of provisional applications U.S. Ser. No. 60/725,484, filed Oct. 8, 2005, U.S. Ser. No. 60/726,447, filed Oct. 12, 2005, and U.S. Ser. No. 60/760,974, filed Jan. 19, 2006, all of which are incorporated herein by reference.

SEQUENCE LISTING

In accordance with 37 CFR §1.52(e)(5), the present specification makes reference to a Sequence Listing (submitted electronically on Jul. 18, 2013 as a .txt file named "SeqListing.txt" in parent application Ser. No. 11/544,389, filed Oct. 6, 2006). The .txt file was generated on Jul. 15, 2013 and is 14 kb in size. The entire contents of the Sequence Listing are herein incorporated by reference.

BACKGROUND OF THE INVENTION

The macula is a small area in the retina of the eye, approximately 3 to 5 millimeters in size, adjacent to the optic nerve. It is the most sensitive area of the retina and contains the fovea, a depressed region that allows for high visual acuity and contains a dense concentration of cones, the photoreceptors that are responsible for color vision.

Macular degeneration is a term that refers to a number of different diseases characterized by degenerative changes in the macula, all of which lead to a loss of central vision. Age-related macular degeneration (ARMD) is the most common cause of functional blindness in developed countries for those over 50 years of age (Seddon, J M. Epidemiology of age-related macular degeneration. In: Ogden, T E, et al., eds. Ryan S J, ed-in-chief. *Retina* Vol II. 3rd ed. St. Louis, Mo.: Mosby; 2001:1039-50). The disease is characterized by progressive degeneration of the retina, retinal pigment epithelium (RPE), and underlying choroid (the highly vascular tissue that lies beneath the RPE, between the retina and the sclera). The retinal pigment epithelial layer is believed to be crucial for photoreceptor health. Cells in this layer recycle visual pigment (rhodopsin), phagocytose photoreceptor tips daily as part of rod and cone regeneration, and transport fluid across the membrane to the choroid, which is believed to help prevent detachment of the neural retina. Central vision deteriorates when cells in the RPE cease to function properly, which can lead to photoreceptor degeneration.

A variety of factors including oxidative stress, inflammation with a possible autoimmune component, genetic background (e.g., mutations), and environmental or behavioral factors such as smoking and diet may contribute to the pathogenesis of ARMD in ways that are as yet not fully understood. Regardless of the underlying etiology, a clinical hallmark of ARMD is the appearance of drusen, localized deposits of lipoproteinaceous material that accumulate in the space between the RPE and Bruch's membrane, which separates the RPE from the choroidal vessels (choriocapillaris). Drusen are typically the earliest clinical finding in ARMD, and the existence, location, and number of drusen are used in classifying the disease into stages and for monitoring its progression (Ambati, J., et al., *Surv. Ophthalmol.*, 48(3): 257-293, 2003; "Preferred Practice Pattern: Age-Related Macular Degeneration", American Academy of Ophthalmology, 2003). Drusen are typically the earliest clinical finding in ARMD.

ARMD has been classified into both "dry" and "wet" (exudative, or neovascular) forms. Dry ARMD is much more common than wet ARMD, but the dry form can progress to the wet form, and the two occur simultaneously in a significant number of cases. Dry ARMD is typically characterized by progressive apoptosis of cells in the RPE layer, overlying photoreceptor cells, and frequently also the underlying cells in the choroidal capillary layer. Confluent areas (typically at least 175 μm in minimum diameter) of RPE cell death accompanied by overlying photoreceptor atrophy are referred to as geographic atrophy. Patients with this form of ARMD experience a slow and progressive deterioration in central vision.

Wet ARMD is characterized by bleeding and/or leakage of fluid from abnormal vessels that have grown from the choroidal vessels (choriocapillaris) beneath the RPE and the macula, which can be responsible for sudden and disabling loss of vision. It has been estimated that much of the vision loss that patients experience is due to such choroidal neovascularization (CNV) and its secondary complications. A subtype of neovascular ARMD in which angiomatous proliferation originates from the retina and extends posteriorly into the subretinal space, eventually communicating in some cases with choroidal new vessels has been identified (Yannuzzi, L. A., et al., *Retina,* 21(5):416-34, 2001). This form of neovascular ARMD, termed retinal angiomatous proliferation (RAP) can be particularly severe. The existence of macular drusen is a strong risk factor for the development of both wet and dry forms of ARMD (Ambati, J., et al., supra).

Treatment options for ARMD are limited, and none are fully effective (Ambati, J., et al., *Surv. Ophthalmol.,* 48(3): 257-293, 2003, and references therein). Thus there is a need in the art for new approaches to the treatment of ARMD and also of other diseases and conditions of the eye characterized by macular degeneration, choroidal neovascularization, retinal neovascularization, retinal angiomatous proliferation, and/or blood vessel leakage. Such diseases and conditions include, but are not limited to, diabetic retinopathy and retinopathy of prematurity. There is also a need in the art for new approaches to the treatment of eye disorders characterized by ocular inflammation.

SUMMARY OF THE INVENTION

The present invention addresses the foregoing needs, among others. The invention provides a method of treating an eye disorder comprising (i) providing a subject in need of treatment for the eye disorder; and (ii) administering a composition comprising a compstatin or a complement inhibiting analog thereof to the subject. Any of a wide variety of eye disorders can be treated. For example, disorders characterized by macular degeneration, choroidal neovascularization, retinal neovascularization, ocular inflammation, or any combination of these, can be treated.

The invention further provides a composition comprising: (i) compstatin or a complement inhibiting analog thereof; and (ii) a moiety that binds to a component present in the eye of a subject at risk of or suffering from an eye disorder characterized by macular degeneration, choroidal neovascularization, retinal neovascularization, ocular inflammation, or any combination of these. The component can be a cellular marker or a noncellular entity, e.g., a molecule or complex that is present in deposits found in the eye of a subject with macular degeneration, ocular inflammation, etc.

The invention further provides a composition comprising: (i) compstatin or a complement inhibiting analog thereof; and (ii) an angiogenesis inhibitor.

The invention further provides a composition comprising a plurality of compstatin analog molecules, or moieties, attached to a polymeric backbone or scaffold or a multimer of compstatin molecules and/or compstatin analogs. The compstatin analog moieties may be identical or different. The composition may contain, e.g., 2, 3, 4, or more different compstatin analogs attached to a polymeric backbone or scaffold.

The invention further provides a composition comprising: (i) compstatin or a complement inhibiting analog thereof; and (ii) a soluble gel-forming material. The composition forms a gel following introduction into the body, e.g., upon contact with a physiological fluid. In one embodiment, the compstatin analog is attached to a polymeric backbone or scaffold. In one embodiment, the composition comprises a plurality of compstatin analog molecules linked to one another. In certain embodiments of the foregoing compositions, the soluble gel-forming material is soluble collagen. The composition may further comprise fibrillar collagen solids. In certain embodiments of the invention any of the compositions comprising a soluble gel-forming material further comprises an angiogenesis inhibitor. The composition may be formed into a gel implant in vitro and administered to, or in the vicinity of, the eye.

The invention further provides ocular implants and polymeric delivery vehicles comprising compstatin or a complement inhibiting analog thereof. In some embodiments of the invention the composition further comprises a moiety that binds to a component present in the eye of a subject at risk of or suffering from an eye disorder characterized by macular degeneration, choroidal neovascularization, retinal neovascularization, or any combination of these. In certain embodiments of the invention either of the foregoing compositions further comprises an angiogenesis inhibitor.

The invention further provides a supramolecular complex comprising compstatin or a complement inhibiting analog thereof or comprising compstatin and one or more complement inhibiting analogs thereof, or comprising multiple different complement inhibiting analogs of compstatin. In some embodiments the composition contains a plurality of compstatin molecules (and/or compstatin analog molecules) attached to a polymeric backbone or scaffold or a multimer of compstatin molecules (and/or compstatin analogs). In some embodiments the composition further comprises a soluble gel-forming material.

The invention further provides methods of treating an eye disorder characterized by macular degeneration, choroidal neovascularization, retinal neovascularization, ocular inflammation, or any combination of these, comprising administering any of the compositions of the invention to a subject at risk of or suffering from the eye disorder. The compositions can be administered as sole therapy, or one or more other treatments for the disorder may also be administered either concurrently or sequentially. Such treatments include, but are not limited to, laser photocoagulation, photodynamic therapy (e.g., Visudyne®), or anti-angiogenic therapy.

Methods for testing the compositions and methods of the invention are also provided.

Methods for making the compositions of the invention are also provided.

In any of the embodiments of the present invention, the eye disorder can be a macular degeneration related condition, diabetic retinopathy, retinopathy of prematurity, uveitis, keratitis, scleritis, retinitis pigmentosa, or any condition featuring choroidal and/or retinal neovascularization and/or ocular inflammation. In certain embodiments the eye disorder is a macular degeneration related condition, e.g., ARMD. In certain embodiments the eye disorder is diabetic retinopathy.

Included among the eye disorders that can be treated with the compositions and methods of the invention are eye disorders in which retinal angiomatous proliferation (RAP) is present. RAP involves abnormal proliferation of retinal blood vessels (retinal neovascularization) and is a feature of a subtype of neovascular ARMD, but the compositions and methods of the invention can be used to treat RAP due to any cause, whether or not associated with macular degeneration. The invention therefore provides a method of inhibiting an eye disorder characterized by retinal angiomatous proliferation comprising (i) providing a subject in need of treatment for the eye disorder; and (ii) administering a composition comprising compstatin or a complement inhibiting analog thereof, to the subject. The composition can be administered using any of the methods described herein. In some embodiments the composition is delivered intravitreally or in close proximity to the posterior segment of the eye.

In any of the embodiments of the invention that features an angiogenesis inhibitor, the angiogenesis inhibitor may be any angiogenesis inhibitor known in the art. For example, the angiogenesis inhibitor may, but need not be, selected from the group consisting of: Macugen® or another VEGF nucleic acid ligand; Lucentis®, Avastin®, or another anti-VEGF antibody; combretastatin or a derivative or prodrug thereof such as Combretastatin A4 Prodrug (CA4P); VEGF-Trap; EVIZON™ (squalamine lactate); AG-013958 (Pfizer, Inc.); JSM6427 (Jerini AG), β2-glycoprotein 1 (β2-GP1), and a short interfering RNA (siRNA) that inhibits expression of one or more VEGF isoforms (e.g., $VEGF_{165}$) or inhibits expression of a VEGF receptor (e.g., VEGFR1).

Unless otherwise stated, the invention makes use of standard methods of molecular biology, chemistry, cell culture, animal maintenance, ophthalmologic examination, and administration of therapeutic agents to subjects, etc., and uses art-accepted meanings of terms. This application refers to various patents and publications. The contents of all scientific articles, books, patents, and other publications, mentioned in this application are incorporated herein by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; *Kuby Immunology*, 4$^{th}$ ed., Goldsby, R. A., Kindt, T. J., and Osborne, B. (eds.), W.H. Freeman, 2000, *Goodman and Gilman's The Pharmacological Basis of Therapeutics*, 10$^{th}$ Ed. McGraw Hill, 2001, Katzung, B. (ed.) *Basic and Clinical Pharmacology*, McGraw-Hill/Appleton & Lange; 9th edition (December 2003), *Ophthalmic Surgery: Principles and Practice*, 3$^{rd}$ ed., W.B. Saunders Company, 2002; Albert, D M and Lucarelli, M J (eds.), *Clinical Atlas of Procedures in Ophthalmic Surgery*, American Medical Association, 2003. It will be appreciated that the state of the art may have progressed beyond that represented in certain of the references incorporated herein. In the event of a conflict or inconsistency between any of the incorporated references and the instant specification, the specification shall typically control unless modified by amendment, it being understood that the determination of whether a conflict or inconsistency exists is within the discretion of the inventors and can be made at any time. Art-accepted abbreviations for the standard amino acids are used herein.

BRIEF DESCRIPTION OF THE DRAWING

FIG. 1C depicts a normal eye. FIG. 1D depicts an eye suffering from dry ARMD. FIG. 1E depicts an eye suffering from exudative ARMD. ONL=outer nuclear layer; IS=inner segment; OS=outer segment; RPE=retinal pigment epithelial layer; BM=Bruch's membrane; CC=choriocapillaris. Adapted from Tezel, T., et al., *Trends in Molecular Medicine*, 10(9), 417-420, 2004.

DEFINITIONS

Figure 1A:
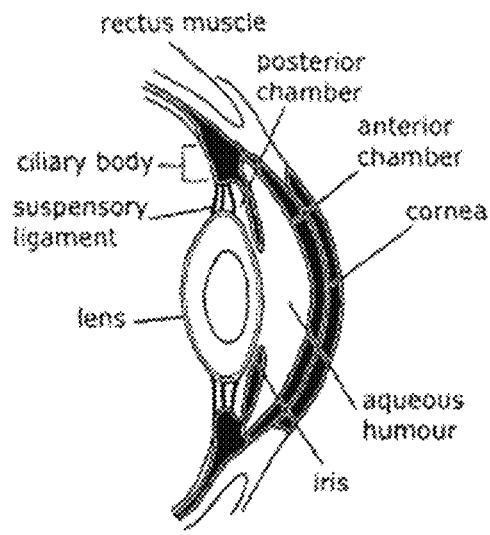
FIGS. 1A-1E show schematic representations of the anterior and posterior segments of the eye (1A and 1B) and the outer layers of the eye (1C-1E).

"Angiogenesis" or "angiogenic" refer to formation, growth, and/or development of new blood vessels.

The terms "angiogenesis inhibitor" and "antiangiogenic agent" are used interchangeably herein to refer to agents that are capable of inhibiting or reducing one or more processes associated with angiogenesis including, but not limited to, endothelial cell proliferation, endothelial cell migration, and capillary tube formation. In addition, such agents may inhibit fluid exudation from blood vessels.

The terms "approximately" or "about" in reference to a number generally include numbers that fall within a range of 5% in either direction (greater than or less than) of the number unless otherwise stated or otherwise evident from the context (except where such number would impermissibly exceed 100% of a possible value).

"Biocompatible" refers to a material that is substantially non-toxic to cells in vitro, e.g., if its addition to cells in culture results in less than or equal to 20% cell death. A material is considered biocompatible with respect to a recipient if it is substantially nontoxic to the recipient's cells in the quantities and at the location used, and also does not elicit or cause a significant deleterious or untoward effect on the recipient's body, e.g., an immunological or inflammatory reaction, unacceptable scar tissue formation, etc.

"Biodegradable" means that a material is capable of being broken down physically and/or chemically within cells or within the body of a subject, e.g., by hydrolysis under physiological conditions, by natural biological processes such as the action of enzymes present within cells or within the body, etc., to form smaller chemical species which can be metabolized and, optionally, reused, and/or excreted or otherwise disposed of Preferably a biodegradable compound is biocompatible.

A "biological macromolecule" is a large molecule composed of smaller subunits of a type that are found in biological systems. Examples of biological macromolecules include polypeptides, nucleic acids, and polysaccharides. Typically a biological macromolecule contains at least 3 subunits (e.g., amino acids, nucleosides, monosaccharides, etc.). The biological macromolecule may, but need not be, a naturally occurring polypeptide, nucleic acid, or polysaccharide. The biological macromolecule may be modified, e.g., it may be conjugated to a nonbiological molecule such as synthetic polymer, etc.

"Choroidal neovascularization" (CNV) refers to the abnormal development, proliferation, and/or growth of blood vessels arising from the choriocapillaris. The blood vessels typically extend through Bruch's membrane, RPE layer, and/or subretinal space.

A "complement component" or "complement protein" is a molecule that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, H, and I, and properdin.

"Concurrent administration" as used herein with respect to two or more agents, e.g., therapeutic agents, is administration performed using doses and time intervals such that the administered agents are present together within the body, or at a site of action in the body such as within the eye) over a time interval in not less than de minimis quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks, etc. Accordingly, the agents may, but need not be, administered together as part of a single composition. In addition, the agents may, but need not be, administered simultaneously (e.g., within less than 5 minutes, or within less than 1 minute) or within a short time of one another (e.g., less than 1 hour, less than 30 minutes, less than 10 minutes, approximately 5 minutes apart). According to various embodiments of the invention agents administered within such time intervals may be considered to be administered at substantially the same time. In certain embodiments of the invention concurrently administered agents are present at effective concentrations within the body (e.g., in the blood and/or at a site of action such as the retina) over the time interval. When administered concurrently, the effective concentration of each of the agents needed to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. The de minimis concentration of an agent may be, for example, less than approximately 5% of the concentration that would be required to elicit a particular biological response, e.g., a desired biological response.

An "effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, an effective amount may be an amount sufficient to achieve one or more of the following: (i) inhibit or prevent drusen formation; (ii) cause a reduction in drusen number and/or size (drusen regression); (iii) cause a reduction in or prevent lipofuscin deposits; (iv) inhibit or prevent visual loss or slow the rate of visual loss; (v) inhibit choroidal neovascularization or slow the rate of choroidal neovascularization; (vi) cause a reduction in size and/or number of lesions characterized by choroidal neovascularization; (vii) inhibit choroidal neovascularization or slow the rate of retinal neovascularization; (viii) cause a reduction in size and/or number of lesions characterized by retinal neovascularization; (ix) improve visual acuity and/or contrast sensitivity; (x) inhibit or prevent photoreceptor or RPE cell atrophy or apoptosis, or reduce the rate of photoreceptor or RPE cell atrophy or apoptosis; (xi) inhibit or prevent progression of non-exudative macular degeneration to exudative macular degeneration; (xii) reduce one or more indicia of inflammation, e.g., the presence of inflammation-associated cells such as white blood cells (e.g., neutrophils, macrophages) in the eye, the presence of endogenous inflammatory mediators known in the art, one or more symptoms such as eye pain, redness, light sensitivity, blurred vision and floaters, etc.

An "expression control sequence" refers to a nucleotide sequence in a polynucleotide that regulates the expression (transcription and/or translation) of a nucleotide sequence operatively linked thereto.

"Exudative" macular degeneration is used herein synonymously with "wet" type macular degeneration, as those terms are generally understood in the art, i.e., to refer to a macular degeneration related condition such as ARMD characterized by neovascularization.

"Fibrillar collagen solids" means the dry collagen solid content of fibrillar collagen. Fibrillar collagen is an insoluble collagen material wherein the collagen molecules interact to form microfibrils which themselves aggregate by side-to-side and end-to-end association to form stabilized collagen fibrils.

"Fusion protein" refers to a polypeptide that contains two or more different polypeptides or portions thereof joined together to form a single polypeptide chain. A recombinant polynucleotide that encodes a fusion protein may be created by removing the stop codon from the polynucleotide that encodes the first polypeptide and appending a polynucleotide that encodes the second polypeptide in frame, so that the resulting recombinant polynucleotide encodes a single polypeptide comprising the two polypeptides.

"Identity" refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. By gap is meant a portion of a sequence that is not occupied by a residue. For example, the sequence A K L - - - SIG (SEQ ID NO: 1) contains a gap of three residues. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between a sequence of interest and sequences in any of a variety of public databases. The algorithm of Karlin and Altschul (Karlin and Altschul, *Proc. Natl. Acad. Sci. USA* 87:22264-2268, 1990) modified as in Karlin and Altschul, *Proc. Natl. Acad. Sci. USA* 90:5873-5877, 1993 is incorporated into the NBLAST and XBLAST programs of Altschul et al. (Altschul, et al., *J. Mol. Biol.* 215:403-410, 1990). To obtain gapped alignments for comparison purposes, Gapped BLAST is utilized as described in Altschul et al. (Altschul, et al. *Nucleic Acids Res.* 25: 3389-3402, 1997). When utilizing BLAST and Gapped BLAST programs, the default parameters of the respective programs may be used. A PAM250 or BLOSUM62 matrix may be used. See the Web site having URL www. followed immediately by_ncbi.nlm.nih.gov for these programs. In a specific embodiment, percent identity of a sequence of interest and a second sequence is calculated using BLAST2 with default parameters.

The term "isolated" means 1) separated from at least some of the components with which it is usually associated in nature; 2) prepared or purified by a process that involves the hand of man; and/or 3) not occurring in nature. For example, a molecule that is removed from a cell that produces it, is "isolated". A chemically synthesized molecule is "isolated".

The term "linked", when used with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

"Liposomes" are artificial microscopic spherical particles formed by a lipid bilayer (or multilayers) enclosing an aqueous compartment. Liposomes can be used for delivering certain of the compositions of the invention.

"Local administration" or "local delivery", in reference to delivery of a composition or agent of the invention, refers to delivery that does not rely upon transport of the composition or agent to its intended target tissue or site via the vascular system. The composition or agent may be delivered directly to its intended target tissue or site, or in the vicinity thereof, e.g., in close proximity to the intended target tissue or site. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site. It will be understood that once having been locally delivered a fraction of a therapeutic agent (typically only a minor fraction of the administered dose) may enter the vascular system and be transported to another location, including back to its intended target tissue or site.

"Macular degeneration related condition" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and/or capillary endothelial cells. ARMD is the major macular degeneration related condition, but a number of others are known including, but not limited to, Best macular dystrophy, Sorsby fundus dystrophy, Mallatia Leventinese and Doyne honeycomb retinal dystrophy.

"Marker", for the purpose of the description of the invention, may refer to any molecular moiety (e.g., protein, peptide, mRNA or other RNA species, DNA, lipid, carbohydrate) that characterizes, indicates, or identifies a particular diseased or physiological state (e.g., apoptotic, cancerous, normal) or characterizes, indicates, or identifies one or more cell type(s), tissue type(s), or embryological origin. The presence or absence of certain marker(s), or the amount of certain marker (s), may indicate a particular physiological or diseased state of a patient, organ, tissue, or cell. A cellular marker is a marker found in or on a cell. A cellular marker may, but need not be, cell type specific. For example, a cell type specific marker is generally a protein, peptide, mRNA, lipid, or carbohydrate that is present at a higher level on or in a particular cell type or cell types of interest than on or in many other cell types. In some instances a cell type specific marker is present at detectable levels only on or in a particular cell type of interest. However, it will be appreciated that useful markers need not be absolutely specific for the cell type of interest. For example, certain CD molecules are present on the cells of multiple different types of leukocytes. In general, a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. More preferably the cell type specific marker is present at levels at least 4-5 fold, between 5-10 fold, or more than 10-fold greater than its average expression in a reference population. Preferably detection or measurement of a cell type specific marker makes it possible to distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc.

"Non-exudative" macular degeneration is used herein synonymously with "dry" type macular degeneration as those terms are generally used in the art, to refer to a macular degeneration related condition, e.g., ARMD, in which neovascularization that would be detectable using standard methods such as fluorescein angiography has not occurred.

"Operably linked" or "operably associated" refers to a relationship between two nucleic acid sequences wherein the expression of one of the nucleic acid sequences is controlled by, regulated by, modulated by, etc., the other nucleic acid sequences, or a relationship between two polypeptides wherein the expression of one of the polypeptides is controlled by, regulated by, modulated by, etc., the other polypeptide. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport, stability, or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence, or a polypeptide that is operatively linked to a second polypeptide, is covalently linked, either directly or indirectly, to such a sequence, although any effective three-dimensional association is acceptable.

"Plurality" means more than one.

"Polynucleotide" or "oligonucleotide" refers to a polymer of nucleotides. As used herein, an oligonucleotide is typically less than 100 nucleotides in length. A polynucleotide or oligonucleotide may also be referred to as a nucleic acid. Typically, a polynucleotide comprises at least three nucleotides. A nucleotide comprises a nitrogenous base, a sugar molecule, and a phosphate group. A nucleoside comprises a nitrogenous base linked to a sugar molecule. In a polynucleotide or oligonucleotide, phosphate groups covalently link adjacent nucleosides to form a polymer. The polymer may comprise or natural nucleosides found in DNA or RNA (e.g., adenosine, thymidine, guanosine, cytidine, uridine, deoxyadenosine, deoxythymidine, deoxyguanosine, and deoxycytidine), other nucleosides or nucleoside analogs, nucleosides containing chemically modified bases and/or biologically modified bases (e.g., methylated bases), intercalated bases, modified sugars, etc. The phosphate groups in a polynucleotide or oligonucleotide are typically considered to form the internucleoside backbone of the polymer. In naturally occurring nucleic acids (DNA or RNA), the backbone linkage is via a 3' to 5' phosphodiester bond. However, polynucleotides and oligonucletides containing modified backbones or non-naturally occurring internucleoside linkages can also be used in the present invention. Such modified backbones include ones that have a phosphorus atom in the backbone and others that do not have a phosphorus atom in the backbone. Examples of modified linkages include, but are not limited to, phosphorothioate and 5'-N-phosphoramidite linkages. See Kornberg and Baker, *DNA Replication,* 2nd Ed. (Freeman, San Francisco, 1992), Scheit, *Nucleotide Analogs* (John Wiley, New York, 1980), U.S. Patent Pub. No. 20040092470 and references therein for further discussion of various nucleotides, nucleosides, and backbone structures that can be used in the polynucleotides or oligonucleotides described herein, and methods for producing them. Typically a polynucleotide of this invention is DNA or RNA.

Polynucleotides and oligonucleotides need not be uniformly modified along the entire length of the molecule. For example, different nucleotide modifications, different backbone structures, etc., may exist at various positions in the polynucleotide or oligonucleotide. Any of the polynucleotides described herein may utilize these modifications.

The polynucleotide may be of any size or sequence and may be single- or double-stranded. If single-stranded the polynucleotide may be the coding (sense) strand or non-coding (anti-sense) strand.

The polynucleotide may be provided by any means known in the art. In certain embodiments, the polynucleotide has been engineered using recombinant techniques (for a more detailed description of these techniques, please see Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may be synthesized using enzymatic techniques, either within cells or in vitro. The polynucleotide may also be chemically synthesized in a laboratory, e.g., using standard solid phase chemistry. The polynucleotide may be modified by chemical and/or biological means. In certain preferred embodiments, these modifications lead to increased stability of the polynucleotide. Modifications include methylation, phosphorylation, end-capping, etc.

The term "polynucleotide sequence" or "nucleic acid sequence" as used herein can refer to the nucleic acid material itself and is not restricted to the sequence information (i.e. the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated.

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328. The polypeptide may be acetylated, e.g., at the N-terminus and/or amidated, e.g., at the C-terminus.

The natural or other chemical modifications such as those described above can occur anywhere in a polypeptide, including the peptide backbone, the amino acid side-chains and the amino or carboxyl termini. A given polypeptide may contain many types of modifications. Polypeptides may be branched, for example, as a result of ubiquitination, and they may be cyclic, with or without branching. Polypeptides may be conjugated with, encapsulated by, or embedded within a polymer or polymeric matrix, dendrimer, nanoparticle, microparticle, liposome, or the like.

Polypeptides may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or methods involving chemical ligation of synthesized peptides (see, e.g., Kent, S., *J Pept Sci.*, 9(9):574-93, 2003), or any combination of the foregoing. These methods are well known, and one of skill in the art will be able to select and implement an appropriate method for synthesizing the peptides and polypeptides described herein. A polypeptide may comprise one or more chemical ligation sites as described, for example, in U.S. Pub. No. 20040115774. In certain embodiments a polypeptide of the invention is modified with a polymer using one or more of the methods described or referenced therein.

The term "polypeptide sequence" or "amino acid sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. A polypeptide sequence presented herein is presented in an N-terminal to C-terminal direction unless otherwise indicated.

"Posterior segment of the eye" refers to the portion of the eye behind the lens, including the vitreous, choroid, and retina (including the macula).

"Purified", as used herein, means that an entity or substance is separated from one or more other entities or substances with which it was previously found before being purified. An entity or substance may be partially purified, substantially purified, or pure. A substance or entity such as a nucleic acid or polypeptide is considered pure when it is removed from substantially all other compounds or entities other than a solvent and any ions contained in the solvent, i.e., it constitutes at least about 90%, more preferably at least about 91%, 92%, 93%, 94%, 95%, 96%, 97%, 98%, 99%, or greater than 99% of the dry weight of the composition. A partially or substantially purified compound or entity such as a nucleic acid or polypeptide may be removed from at least 50%, at least 60%, at least 70%, or at least 80% by weight of the material with which it is naturally found, e.g., cellular material such as cellular proteins and/or nucleic acids. In certain embodiments the of a purified nucleic acid or polypeptide constitutes at least 10%, 20%, 30%, 40%, 50%, 60%, 70%, 80%, 90%, 95%, 99% or even more, by dry weight, of the total nucleic acid or polypeptide, respectively, in a composition. Methods for assessing purity are known in the art and include chromatographic methods, immunological methods, electrophoretic methods, etc. Any of the polynucleotides or polypeptides described herein may be purified.

"Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those frequently used to prepare bioconjugates, e.g., N-hydroxysuccinimide esters, maleimides, sulfhydryls, and the like (see, for example, Hermanson, G., *Bioconjugate Techniques*, Academic press, San Diego, 1996). Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Recombinant host cells", "host cells", and other such terms, denote prokaryotic or eukaryotic cells or cell lines that have been used as recipients for an exogenous nucleic acid (typically DNA) such as an expression vector into which a nucleic acid portion that encodes a polypeptide of interest has been inserted. These terms include the progeny of the original cell into which the vector or other nucleic acid has been introduced. Appropriate unicellular host cells include any of those routinely used in expressing polynucleotides (e.g., eukaryotic, mammalian, and/or viral polynucleotides) including, for example, prokaryotes, such as *E. coli*; and eukaryotes, including for example, fungi, such as yeast (e.g., *Pichia pastoris*); insect cells (e.g., Sf9), plant cells, and animal cells, e.g., mammalian cells such as CHO, R1.1, B-W, L-M, African Green Monkey Kidney cells (e.g. COS-1, COS-7, BSC-1, BSC-40 and BMT-10) and cultured human cells. Terms such as "host cells", etc., are also used to refer to cells or cell lines that can be used as recipients for an exogenous nucleic acid, prior to its introduction. A "recombinant polynucleotide" is one that contains nucleic acid portions that are not found joined together in nature. A "recombinant polypeptide" is a polypeptide that is produced by transcription and translation of an exogenous nucleic acid by a recombinant host cell, typically after introduction of an expression vector that contains a portion that encodes the recombinant polypeptide into the host cell.

"Retinal neovascularization" refers to the abnormal development, proliferation, and/or growth of blood vessels on or in the retina, e.g., on the retinal surface.

"Sequential administration" of two or more agents refers to administration of two or more agents to a subject such that the agents are not present together in the subject's body, or at a relevant site of activity in the body, at greater than de minimis concentrations. Administration of the agents may, but need not, alternate. Each agent may be administered multiple times.

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant, epitope, binding pocket or cleft, recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. Binding of two or more molecules may be considered specific if the affinity (as measured by the equilibrium dissociation constant, Kd) is $10^{-3}$ M or less, preferably $10^{-4}$M or less, more preferably $10^{-5}$ M or less, e.g., $10^{-6}$M or less, $10^{-7}$M or less, $10^{-8}$M or less, or $10^{-9}$M or less under the conditions tested, e.g., under physiological conditions.

"Significant sequence homology" as applied to an amino acid sequence means that the sequence displays at least approximately 20% identical or conservatively replaced amino acids, preferably at least approximately 30%, at least approximately 40%, at least approximately 50%, at least approximately 60% identical or conservatively replaced amino acids, desirably at least approximately 70% identical or conservatively replaced amino acids, more desirably at least approximately 80% identical or conservatively replaced amino acids, and most desirably at least approximately 90% amino acid identical or conservatively replaced amino acids relative to a reference sequence. When two or more sequences are compared, any of them may be considered the reference sequence. Percent identity can be calculated using a FASTA or BLASTP algorithm, using default parameters. A PAM250 or BLOSUM62 matrix may be used. For purposes of calculating % identical or conservatively replaced residues, a conservatively replaced residue is considered identical to the residue it replaces. Conservative replacements may be defined in accordance with Stryer, L. *Biochemistry*, 3rd ed., 1988, according to which amino acids in the following groups possess similar features with respect to side chain properties such as charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; (7) Cyclic aliphatic side chain: P, which may be considered to fall within group (1).

"Subject", as used herein, refers to an individual to whom an agent is to be delivered, e.g., for experimental, diagnostic, and/or therapeutic purposes. Preferred subjects are mammals, particularly domesticated mammals (e.g., dogs, cats, etc.), non-human primates, or humans.

"Supramolecular complex" refers to an assembly comprising at least two entities that are physically associated with one another, in which one or more entities is not covalently linked to another entity but is instead associated with that entity by through one or more noncovalent interactions mechanisms such as ionic interactions, hydrogen bonds, hydrophobic interactions, π-stacking, dative bonds, etc. For example, one or more entities may be entrapped, embedded, enclosed, or encapsulated within another entity, or entangled with another entity, or dissolved in another entity, or impregnated with another entity, or adsorbed to another entity, or bound to another entity, so as to maintain a physical association between the entities. The entities may be naturally occurring or synthetic. They may be, for example, polypeptides, non-polypeptide polymers, nucleic acids, lipids, small molecules, carbohydrates, etc. One or more of the entities may be a rigid or flexible polymer scaffold, a three-dimensional structure such as a microparticle, nanoparticle, liposome, dendrimer, etc. The supramolecular complex can contain any number or combination of molecules and/or other entities.

"Treating", as used herein, refers to providing treatment, i.e, providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. "Prevent" refers to causing a disease, disorder, condition, or symptom or manifestation of such not to occur for at least a period of time in at least some individuals. Treating can include administering an agent to the subject following the development of one or more symptoms or manifestations indicative of a condition such as macular degeneration or diabetic retinopathy, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of this invention can be administered to a subject who has developed an eye disorder such as exudative or non-exudative ARMD or diabetic retinopathy or is at increased risk of developing such a disorder relative to a member of the general population. A composition of this invention can be administered prophylactically, i.e., before development of any symptom or manifestation of the condition. Typically in this case the subject will be at risk of developing the condition.

"Vector" is used herein to refer to a nucleic acid or a virus or portion thereof (e.g., a viral capsid) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part or all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral capsids. Plasmid vectors typically include an origin of replication and one or more selectable markers. Plasmids may include part or all of a viral genome (e.g., a viral promoter, enhancer, processing or packaging signals, etc.). Viruses or portions thereof (e.g., viral capsids) that can be used to introduce nucleic acid molecules into cells are referred to as viral vectors. Useful viral vectors include adenoviruses, retroviruses, lentiviruses, vaccinia virus and other poxviruses, herpes simplex virus, and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not, be supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Where sufficient information is lacking it may, but need not be, supplied by a host cell or by another vector introduced into the cell.

Expression vectors are vectors that include regulatory sequence(s), e.g., expression control sequences such as a promoter, sufficient to direct transcription of an operably linked nucleic acid. An expression vector comprises sufficient cis-acting elements for expression; other elements for expression can be supplied by the host cell or in vitro expression system. Such vectors typically include one or more appropriately positioned sites for restriction enzymes, to facilitate introduction of the nucleic acid to be expressed into the vector.

A "variant" of a particular polypeptide or polynucleotide has one or more alterations (e.g., additions, substitutions, and/or deletions, which may be referred to collectively as "mutations") with respect to the polypeptide or nucleic acid, which may be referred to as the "original polypeptide or polynucleotide". Thus a variant can be shorter or longer than the polypeptide or polynucleotide of which it is a variant. The terms "variant" encompasses "fragments". A "fragment" is a continuous portion of a polypeptide that is shorter than the original polypeptide. In certain embodiments of the invention a variant polypeptide has significant sequence homology to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In certain embodiments of the invention a variant polypeptide has substantial sequence homology to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In a non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In another non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In specific embodiments the sequence of a variant polypeptide has N amino acid differences with respect to an original sequence, wherein N is any integer between 1 and 10. In other specific embodiments the sequence of a variant polypeptide has N amino acid differences with respect to an original sequence, wherein N is any integer between 1 and 20. An amino acid "difference" refers to a substitution, insertion, or deletion of an amino acid.

In certain embodiments of the invention a fragment or variant possesses sufficient structural similarity to the original polypeptide so that when its 3-dimensional structure (either actual or predicted structure) is superimposed on the structure of the original polypeptide, the volume of overlap is at least 70%, preferably at least 80%, more preferably at least 90% of the total volume of the structure of the original polypeptide. A partial or complete 3-dimensional structure of the fragment or variant may be determined by crystallizing the protein, which can be done using standard methods. Alternately, an NMR solution structure can be generated, also using standard methods. A modeling program such as MODELER (Sali, A. and Blundell, T L, *J. Mol. Biol.*, 234, 779-815, 1993), or any other modeling program, can be used to generate a predicted structure. If a structure or predicted structure of a related polypeptide is available, the model can be based on that structure. The PROSPECT-PSPP suite of programs can be used (Guo, J T, et al., *Nucleic Acids Res.* 32(Web Server issue):W522-5, Jul. 1, 2004).

Preferably one, more than one, or all biological functions or activities of a variant or fragment is substantially similar to that of the corresponding biological function or activity of the original molecule. For example, an activity of a variant or fragment is considered substantially similar to the activity of the original molecule if the activity of the variant or fragment is at least 20%, at least 50%, at least 60%, at least 70%, at least 80%, or at least 90% of the activity of the original molecule, up to approximately 100%, approximately 125%, or approximately 150% of the activity of the original molecule. In other nonlimiting embodiments an activity of a variant or fragment is considered substantially similar to the activity of the original molecule if the amount or concentration of the variant needed to produce an effect is within 0.5 to 5-fold of the amount or concentration of the original molecule needed to produce that effect.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

Detailed Description of Certain Embodiments of the Invention

Overview

The present invention provides compositions and methods for treatment of eye disorders characterized by macular degeneration, choroidal neovascularization, retinal neovascularization, ocular inflammation, or any combination of the foregoing. The phrase "characterized by" is intended to indicate that macular degeneration, CNV, RNV, and/or ocular inflammation is a characteristic (i.e., typical) feature of the disorder. Macular degeneration, CNV, RNV, and/or ocular inflammation may be a defining and/or diagnostic feature of the disorder. Exemplary disorders that are characterized by one or more of these features and can be treated with the compositions and methods of the invention include, but are not limited to, macular degeneration related conditions, diabetic retinopathy, retinopathy of prematurity, proliferative vitreoretinopathy, uveitis, keratitis, and scleritis. As mentioned above, macular degeneration refers to a variety of degenerative conditions characterized by central visual loss due to deterioration of the macula. The most common of these conditions is age related macular degeneration (ARMD), which exists in both "dry" and "wet" forms.

Ocular inflammation can affect a large number of eye structures including the conjunctiva, cornea, episclera, sclera, uveal tract, retina, vasculature, optic nerve, and orbit. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. Uveitis can arise from a number of different causes and is associated with a number of different diseases, including, but not limited to, rheumatic diseases such as rheumatic diseases (e.g., ankylosing spondylitis and juvenile rheumatoid arthritis), certain infectious diseases such as tuberculosis and syphilis, other conditions such as sarcoidosis, systemic lupus erythematosus, chemical injury, trauma, surgery, etc. In one embodiment, the type of uveitis is anterior uveitis. In another embodiment the type of uveitis is posterior uveitis. Keratis refers to inflammation of the cornea. Keratitis has a diverse array of causes including bacterial, viral, or fungal infection, trauma, and allergic reaction. Amoebic infection of the cornea, e.g., caused by Acanthamoeba, is a particular problem for contact lens wearers. Scleritis refers to inflammation of the sclera. Uveitis, keratitis, and scleritis, and methods for their diagnosis are well known in the art. Symptoms of the various inflammatory conditions that affect the eye can include, but are not limited to, eye pain, redness, light sensitivity, tearing, blurred vision, floaters. Ocular inflammation of various types is well known to occur in association with a variety of local or systemic diseases, some of which are noted above. In some instances the cause may remain unknown.

The invention provides a method of treating an eye disorder characterized by macular degeneration, choroidal neovascularization, retinal neovascularization, proliferative vitreoretinopathy, glaucoma, ocular inflammation, or any combination of these, comprising (i) providing a subject in need of treatment for the eye disorder; and (ii) administering a composition comprising compstatin or a complement inhibiting analog thereof to the subject. The invention further provides a method of inhibiting CNV, RNV, or both in the eye of a subject suffering from or at risk of an eye disorder characterized by macular degeneration, choroidal neovascularization, retinal neovascularization, proliferative vitreoretinopathy, glaucoma, or any combination of these, comprising the step of: administering a composition comprising compstatin or a complement inhibiting analog thereof to or in close proximity to the posterior segment of the subject's eye. The invention further provides a method of inhibiting CNV, RNV, or both in the eye of a subject suffering from or at risk of an eye disorder characterized by ocular inflammation, comprising the step of: administering a composition comprising compstatin or a complement inhibiting analog thereof to or in close proximity to the posterior segment of the subject's eye.

The invention further provides a method of treating an eye disorder associated with or caused at least in part by complement activation, the method comprising the step of administering a compstatin analog to a subject suffering from or at risk of the eye disorder. In one embodiment the disorder is ARMD. In one embodiment the disorder is diabetic retinopathy. In one embodiment the disorder is uveitis. In one embodiment the disorder is glaucoma. The invention further provides a method of treating an eye disorder characterized in that a polymorphism in, or in linkage disequilibrium with, a gene that encodes a complement component is associated with an increased risk of the disorder, the method comprising the step of administering a compstatin analog to a subject suffering from or at risk of the eye disorder. The polymorphism may be one that results in increased complement activity. The subject may be homozygous or heterozygous for the polymorphism or may not exhibit the polymorphism. The subject may have one or more other risk factors for developing the disorder. The invention further provides a method of treating an eye disorder characterized in that a polymorphism in, or in linkage disequilibrium with, a gene that encodes a complement component is associated with a decreased risk of the disorder, the method comprising the step of administering a compstatin analog to a subject suffering from or at risk of the eye disorder. The polymorphism may be one that results in decreased complement activity. The subject may be homozygous or heterozygous for the polymorphism or may not exhibit the polymorphism. The subject may have one or more risk factors for developing the disorder. In certain embodiments of the invention the disorder is ARMD.

The events that occur in ARMD may be understood with reference to the various panels of FIG. 1. FIGS. 1A and 1B show structures present in the anterior and posterior segments of the eye, including the retina, which contains the macula. FIGS. 1C-1E depict the outer layers of a normal eye (1C), an eye suffering from dry ARMD (1D), and an eye suffering from exudative (wet) ARMD (1E). The outer nuclear layer (ONL), contains nuclei of rod and cone photoreceptors. Each photoreceptor contains an inner segment (IS) and outer segment (OS), the latter of which contains the pigment rhodopsin, which initiates the phototransduction cascade following exposure to light. The retinal pigment epithelial layer (RPE) lies below the photoreceptors and above Bruch's membrane, a layer of extracellular matrix that separates the RPE from a network of capillaries, the choriocapillaris (CC).

Dry ARMD is characterized by the existence of deposits known as drusen and the
separation of the RPE from BM, which is often accompanied by RPE atrophy and apoptosis and loss of underlying choriocapillaris and overlying photoreceptors, resulting in some instances in areas of geographic atrophy which can eventually coalesce to form large patches. In exudative ARMD, new blood vessels grow from the choriocapillaris through Bruch's membrane and can extend into the RPE and photoreceptor cell layers (choroidal neovascularization). These blood vessels can bleed and leak fluid, frequently resulting in sudden visual loss due to events such as RPE and/or retinal detachment. Eventually a fibrovascular scar may form, leading to irreversible visual loss. In some forms of neovascular ARMD, angiomatous proliferation originates from the retina and extends posteriorly into the subretinal space, eventually communicating in some cases with new choroidal vessels. This form of neovascular ARMD, termed retinal angiomatous proliferation (RAP), can be particularly severe. It has been suggested that angiomatous proliferation within the retina is the first manifestation of the vasogenic process in this form of neovascular ARMD. Dilated retinal vessels and pre-, intra-, and subretinal hemorrhages and exudate evolve, surrounding the angiomatous proliferation as the process extends into the deep retina and subretinal space. The present invention provides compositions and methods that inhibit one or more of the events or processes that take place in ARMD. The invention is based in part on the discovery that certain complement inhibitors are particularly suitable as therapeutic agents for macular degeneration and related conditions, for diabetic retinopathy, and/or for choroidal neovascularization associated with any of these disorders, or others. As described in Example 1, an analog of the cyclic peptide compstatin was shown to be effective in significantly inhibiting the development of CNV in an animal model, i.e., the compstatin analog was effective in preventing at least some of the CNV that would otherwise have occurred. Example 1 also presents data showing that another inhibitor of complement activation, vaccinia virus complement control protein (VCP) also significantly inhibits the development of CNV in an animal model, i.e., VCP is effective in preventing at least some of the CNV that would otherwise have occurred. To the best of the inventors' knowledge, this work represents the first demonstration that administration of an inhibitor of complement activation is effective in inhibiting and at least partially preventing development of CNV and the first demonstration that these agents will be effective treatments for eye disorders such as those discussed herein.

To facilitate understanding of the invention, the complement system will first be briefly outlined. Further information is found in the references cited herein. Subsequent sections describe compstatin and analogs thereof, compositions containing compstatin and/or analog(s) thereof, methods of use, etc.

Complement Pathways

The complement system plays a crucial role in a number of physiological processes including the response to injury and defense against foreign entities such as infectious agents. The complement system is also known to play a role in a number of diseases (Makrides, S C, *Pharm Rev.*, 50(1): 59-87). The complement system comprises more than 30 serum and cellular proteins that are involved in two major pathways, known as the classical and alternative pathways (*Kuby Immunology*, 2000).

The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils. C3 and C5 convertase activity is controlled by a number of endogenous members of the Regulators of Complement Activation (RCA) family, also called Complement Control Protein (CCP) family, which includes complement receptor type 1 (CR1; C3b:C4b receptor), complement receptor type 2 (CR2), membrane cofactor protein (MCP; CD46), decay-accelerating factor (DAF), factor H (fH), and C4b-binding protein (C4 bp). Makrides, 1998, and references therein describe the complement system and its components. RCA proteins are also described in U.S. Pat. No. 6,897,290.

The alternative pathway is initiated by microbial surfaces and various complex polysaccharides. In this pathway, C3b, resulting from cleavage of C3, which occurs spontaneously at a low level, binds to targets, e.g., on cell surfaces and forms a complex with factor B, which is later cleaved by factor D, resulting in a C3 convertase. Cleavage of C3 and binding of another molecule of C3b to the C3 convertase gives rise to a C5 convertase. C3 and C5 convertases of this pathway are regulated by CR1, DAF, MCP, and fH. The mode of action of these proteins involves either decay accelerating activity (i.e., ability to dissociate convertases), ability to serve as cofactors in the degradation of C3b or C4b by factor I, or both.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

A third complement pathway, the lectin complement pathway is initiated by binding of mannose-binding lectin (MBL) and MBL-associated serine protease (MASP) to carbohydrates. In the human lectin pathway, MASP-1 and MASP-2 are involved in the proteolysis of C4, C2 and C3, leading to a C3 convertase described above.

As mentioned above, complement activity is regulated by various mammalian proteins referred to as complement control proteins (CCPs). These proteins differ with respect to ligand specificity and mechanism(s) of complement inhibition (Lisczewski, M K and Atkinson, J P, in *The Human Complement System in Health and Disease*, eds. Volanakis, J E and Frank, M M, Dekker, N.Y., pp. 149-66, 1998). They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains (Reid, K B M and Day, A J, *Immunol Today*, 10:177-80, 1989). These domains, consisting of approximately 50-70 amino acids, typically about 60 amino acids, are characterized by a conserved motif that includes four disulfide-bonded cysteines (two disulfide bonds), proline, tryptophan, and many hydrophobic residues.

Compstatin, Compstatin Analogs, and Methods of Use Thereof

Compstatin is a cyclic peptide that binds to complement component C3 and inhibits complement activation. Compstatin inhibits cleavage of C3 to C3a and C3b by convertase. Since C3 is a central component of all three pathways of complement activation, compstatin and analogs thereof are able to inhibit activation of the converging protein of all three pathways. Without wishing to be bound by any theory, the ability of compstatin and analogs thereof to inhibit the alternative pathway of complement activation may contribute significantly to efficacy in certain of the ophthalmic conditions described herein.

The inventors propose that delivery of a therapeutic agent in a sustained manner over a prolonged period of time (e.g., 3-6 months, 6-12 months, 1-2 years) will offer opportunities to inhibit progression of chronic ophthalmic diseases such as ARMD and allow intervention early in the disease process before significant vision loss has occurred. The invention encompasses the recognition that complement inhibitors, and compstatin analogs in particular, possess unique and unexpected advantages in this and other respects as compared, for example, with existing or proposed therapeutics such as angiogenesis inhibitors and anti-inflammatory steroids.

The invention further encompasses the recognition that compstatin and analogs thereof possess unique and unexpected advantages as compared with other complement inhibitors. The relatively low molecular weight (~1.6 kD) and various other properties of compstatin analogs facilitate their incorporation into sustained delivery formulations and devices suitable for providing therapeutic concentrations to ocular tissues. In addition, the inventors determined that the half-life of a compstatin analog (compstatin C) in vitro in the vitreous was high (~6.9 hours) as compared with the rate at which compstatin is degraded and/or cleared from the bloodstream in vivo (half-life of <15 min). The inventors' calculations establish, for the first time, the feasibility of substantially inhibiting C3 activation at levels at or above those expected to be present in the vitreous of a subject with wet ARMD by sustained intravitreal delivery of amounts as little as 5 µg/day of a therapeutic agent, which amounts may, according to the invention, be delivered by intravitreal implant technology over prolonged periods of time (as described further below). The inventors' calculations also establish, for the first time, the feasibility of substantially inhibiting C3 activation at levels at or above those expected to be present in the vitreous of a subject with dry ARMD by sustained intravitreal delivery of amounts as low as 2 µg/day of a therapeutic agent, which amounts may be delivered over prolonged periods of time by intravitreal implant technology according to the present invention.

The invention provides a method of inhibiting complement activation in the eye of a subject comprising administering a compstatin analog to the subject in an amount effective to detectably inhibit complement activation in the vitreous, retina, or both, of the subject over a period of at least 3 months, e.g., 3-6 months, 6-12 months, 12-24 months, 24-36 months, etc. In certain embodiments of the invention the compstatin analog is administered by one or more intravitreal injections. In certain embodiments of the invention the compstatin analog is administered by release from an ocular insert or other sustained release formulation such as microparticles or nanoparticles. The compstatin analog may be released by diffusion out of the formulation or may be released as the formulation erodes. The treatment may be repeated multiple times. In certain embodiments the administration is performed at intervals of, on average, every 6-12 months, or every 12-24 months. In certain embodiments the ocular insert or other sustained release formulation is biodegradable. In certain embodiments the subject suffers from an ocular disorder. In certain embodiments the effective concentration is between 10% and 250% of the average concentration of C3 in the vitreous of eyes suffering from the ocular disorder. In certain embodiments the subject is at risk of an ocular disorder. In certain embodiments the subject has one or more genetic polymorphisms that are associated with increased risk of an ocular disorder, e.g., ARMD. The genetic polymorphism may be in a gene that encodes a complement component such as complement factor H(CFH) or B (CFB). The genetic polymorphism may be in LOC387715 or PLEKHA1. In any of the foregoing embodiments the ocular disorder may be wet or dry ARMD. Exemplary polymorphisms that increase risk of ARMD are located in genes that encode CFH (e.g., Y402H—see Donoso, L, et al, Survey of Ophthalmology, Vol. 51, No. 2, 137-152, 2006, and references therein which are incorporated herein by reference), toll-like receptor 4 (TLR4) (e.g., D299G—see Zareparsi, et al., Human Molecular Genetics, vol. 14, no. 11, pp. 1449-1455, 2005), or in LOC387715 or PLEKHA1 (Donoso, supra). Li, M., et al., Nat. Genet. 38(9):1049-1054, 2006, and Maller, J., et al., Nat. Genet., 38(9):1055-1059, 2006, describe additional polymorphisms in coding and noncoding portions of the CFH gene that are associated with increased risk of ARMD. It will be appreciated that some polymorphisms are associated with a decreased risk of ARMD. See, e.g., Hughes, et al., Nat. Genet., 38(10):1173-7, 2006, describing a haplotype with deletion of CFHR1 and CFHR3 associated with decreased risk of ARMD. These polymorphisms may be protective against ARMD. It will further be appreciated that polymorphisms that are in linkage disequilibrium with any of the afore-mentioned polymorphisms may also be informative for purposes of determining whether a subject is at increased risk of ARMD and/or for quantitatively determining the risk. In certain embodiments the alternative pathway is inhibited. In certain embodiments the classical pathway is inhibited. In certain embodiments the lectin pathway is inhibited. In certain embodiments at least two of the alternate, classical, and lectin pathways is inhibited.

Compstatin is described in U.S. Pat. No. 6,319,897, which is incorporated herein by reference. As described therein, compstatin has the sequence Ile-[Cys-Val-Val-Gln-Asp-Trp-Gly-His-His-Arg-Cys]-Thr (SEQ ID NO: 8), with the disulfide bond between the two cysteines denoted by brackets. Compstatin is an N-terminal cyclic region of a larger peptide (SEQ ID NO: 1 in U.S. Pat. No. 6,319,897) that also shows complement inhibiting activity. In addition, a number of fragments and variants of compstatin inhibit complement, some of them having a higher inhibitory activity than compstatin itself Any of these peptides are of use in the compositions and methods of the present invention. For example, peptides designated by SEQ ID NOs: 13, 15, 20, 21, and 22 in U.S. Pat. No. 6,319,897 show complement inhibiting activity and are of use. In certain embodiments of the invention a peptide having higher complement inhibiting activity than compstatin, e.g., at least 5-fold higher activity, at least 10-fold higher activity, etc., is used.

A variety of compstatin analogs that have higher complement inhibiting activity than compstatin have been synthesized. Certain of these are described in WO2004/026328 (PCT/US2003/029653), Morikis, D., et al., *Biochem Soc Trans.* 32(Pt 1):28-32, 2004, Mallik, B., et al., *J. Med. Chem.*, 274-286, 2005, and/or in Katragadda, M., et al. *J. Med. Chem.*, 49: 4616-4622, 2006, all of which are incorporated herein by reference. Any of the complement inhibiting peptides and peptidomimetics described therein can be used in the present invention. For example, SEQ ID NOs: 4-13 as described in WO2004/026328 can be used in the present invention.

Compstatin and any of its analogs may be acetylated or amidated, e.g., at the N-terminus and/or C-terminus. For example, compstatin and any of its analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

A supramolecular complex comprising compstatin and/or one or more complement inhibiting analogs thereof is also an aspect of the present invention and of use in the methods of the invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain compstatin analogs and suitable assays are described in U.S. Pat. No. 6,319,897, WO2004/026328, Morikis, supra, Mallik, supra, and/or Katragadda 2006, supra. The assay may, for example, measure alternative pathway-mediated erythrocyte lysis or be an ELISA assay (see Examples 4 and 5). WO2004/026328, Morikis, supra, Mallik, supra, and Katragadda 2006, supra, among other references, describe compstatin analogs having higher activity than compstatin and methods for determining their ability to inhibit complement activation. Additional compstatin analogs are an aspect of this invention. The invention includes embodiments in which any one or more of the compstatin analogs or compositions described herein is used in any the methods of treatment described herein.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 µM using an alternative pathway-mediated erythrocyte lysis assay (WO2004/026328). In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 264 and 300, 300 and 350, 350 and 400, or 400 and 500 times as great as that of compstatin. The invention further contemplates compstatin analogs having activities between 500 and 1000 times that of compstatin.

The $K_d$ of compstatin binding to C3 has been measured as 1.3 µM using isothermal titration calorimetry (Katragadda, et al., *J. Biol. Chem.*, 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 µM and 1.0 µM, between 0.05 µmM and 0.1 µM, between 0.025 µM and 0.05 µM, between 0.015 µM and 0.025 µM, between 0.01 µM and 0.015 µM, or between 0.001 µM and 0.01 µM. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence shown in the upper portion of FIG. 2, in which X4 and X9 represent modifiable side chains.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-Nal), 1-naphthylalanine (1-Nal), 2-indanylglycine carboxylic acid (2Ig1), dihydrotrpytophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH—W), 5-hydroxy-L-tryptophan (5OH—W), 6-hydroxy-L-tryptophan (6OH—W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, *J. Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of $(X'aa)_n$-Gln-Asp-Xaa-Gly-$(X''aa)_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Tip, aromatic amino acids, and aromatic amino acid analogs.

In certain preferred embodiments of the invention the peptide is cyclic. The peptide may be cyclized via a bond between any two amino acids, one of which is $(X'aa)_n$ and the other of which is located within $(X''aa)_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used.

In certain embodiments, the compstatin analog is a compound that comprises a peptide having a sequence:
Xaa1-Cys-Val-Xaa2-Gln-Asp-Xaa2*-Gly-Xaa3-His-Arg-Cys-Xaa4 (SEQ ID NO: 6); wherein:
Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-Nal), 1-naphthylalanine (1-Nal), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or vitreous. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—NH$_2$ or —NHR$^1$, wherein R is an organic moiety such as an alkyl group).

In certain embodiments of the invention blocking moiety $B^1$ is any moiety that neutralizes or reduces the negative charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 7); wherein:

Xaa1 is Ile, Val, Leu, Ac-Ile, Ac-Val, Ac-Leu or a dipeptide comprising Gly-Ile or Ac-Gly-Ile;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH$_2$; and the two Cys residues are joined by a disulfide bond.

Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

Table 1 provides a non-limiting list of compstatin analogs useful in the present invention. The analogs are referred to in abbreviated form in the left column by indicating specific modifications at designated positions (1-13) as compared to the parent peptide, compstatin (amidated at the C-terminus). Unless otherwise indicated, peptides are amidated at the C-terminus. Bold text is used to indicate certain modifications. Activity relative to compstatin (in this case compstatin amidated at the C-terminus) is based on published data and assays described therein (WO2004/026326, Mallik, 2005; Katragadda, 2006). Where multiple publications reporting an activity were consulted, the more recently published value is used, and it will be recognized that values may be adjusted in the case of differences between assays. It will also be appreciated that the peptides listed in Table 1 are cyclized via a disulfide bond between the two Cys residues when used in the therapeutic compositions and methods of the invention.

TABLE 1

| Peptide | Sequence | SEQ ID NO: | Activity over compstatin |
|---|---|---|---|
| compstatin | H-ICVVQDWGHHRCT-CONH2 | 8 | * |
| Ac-compstatin | Ac-ICVVQDWGHHRCT-CONH2 | 9 | 3xmore |
| Ac-V4Y/H9A | Ac-ICVYQDWGAHRCT-CONH2 | 10 | 14xmore |
| Ac-V4W/H9A —OH | Ac-ICVWQDWGAHRCT-COOH | 11 | 27xmore |
| Ac-V4W/H9A | Ac-ICVWQDWGAHRCT-CONH2 | 12 | 45xmore |
| Ac-V4W/H9A/T13dT —OH | Ac-ICVWQDWGAHRCdT-COOH | 13 | 55xmore |
| Ac-V4(2-Nal)/H9A | Ac-ICV(2-Nal)QDWGAHRCT-CONH2 | 14 | 99xmore |
| Ac V4(2-Nal)/H9A —OH | Ac-ICV(2-Nal)QDWGAHRCT-COOH | 15 | 38xmore |
| Ac V4(1-Nal)/H9A —OH | Ac-ICV(1-Nal)QDWGAHRCT-COOH | 16 | 30xmore |
| Ac-V42Igl/H9A | Ac-ICV(2-Igl)QDWGAHRCT-CONH2 | 17 | 39xmore |
| Ac-V42Igl/H9A —OH | Ac-ICV(2-Igl)QDWGAHRCT-COOH | 18 | 37xmore |
| Ac-V4Dht/H9A —OH | Ac-ICVDhtQDWGAHRCT-COOH | 19 | 5xmore |
| Ac-V4(Bpa)/H9A —OH | Ac-ICV(Bpa)QDWGAHRCT-COOH | 20 | 49xmore |
| Ac-V4(Bpa)/H9A | Ac-ICV(Bpa)QDWGAHRCT-CONH2 | 21 | 86xmore |
| Ac-V4(Bta)/H9A —OH | Ac-ICV(Bta)QDWGAHRCT-COOH | 22 | 65xmore |

TABLE 1-continued

| Peptide | Sequence | SEQ ID NO: | Activity over compstatin |
|---|---|---|---|
| Ac-V4(Bta)/H9A | Ac-ICV(Bta)QDWGAHRCT-CONH2 | 23 | 64xmore |
| Ac-V4W/H9(2-Abu) | Ac-ICVWQDWG(2-Abu)HRCT-CONH2 | 24 | 64xmore |
| +G/V4W/H9A +AN —OH | H-GICVWQDWGAHRCTAN-COOH | 25 | 38xmore |
| Ac-V4(5fW)/H9A | Ac-ICV(5fW)QDWGAHRCT-CONH$_2$ | 26 | 31xmore |
| Ac-V4(5-MeW)/H9A | Ac-ICV(5-methyl-W)QDWGAHRCT-CONH$_2$ | 27 | 67xmore |
| Ac-V4(1-MeW)/H9A | Ac-ICV(1-methyl-W)QDWGAHRCT-CONH$_2$ | 28 | 264xmore |
| Ac-V4W/W7(5fW)/H9A | Ac-ICVWQD(5fW)GAHRCT-CONH$_2$ | 29 | 121xmore |
| Ac-V4(5fW)/W7(5fW)/H9A | Ac-ICV(5fW)QD(5fW)GAHRCT-CONH$_2$ | 30 | NA |
| Ac-V4(5-MeW)/W7(5fW)H9A | Ac-ICV(5-methyl-W)QD(5fW)GAHRCT-CONH$_2$ | 31 | NA |
| Ac-V4(1MeW)/W7(5fW)/H9A | Ac-ICV(1-methyl-W)QD(5fW)GAHRCT-CONH$_2$ | 32 | 264xmore |

NA = not available

In certain embodiments of the compositions and methods of the invention the compstatin analog has a sequence selected from sequences 9-32. In certain embodiments of the compositions and methods of the invention the compstatin analog has a sequence selected from SEQ ID NOs: 14, 21, 28, 29, and 32. In certain embodiments of the compositions and methods of the invention the compstatin analog has a sequence selected from SEQ ID NOs: 30 and 31. In one embodiment of the compositions and methods of the invention the compstatin analog has a sequence of SEQ ID NO: 28. In one embodiment of the methods of the invention the compstatin analog has a sequence of SEQ ID NO: 32.

The invention further provides compstatin analogs, having sequences as set forth in Table 1, but where the Ac-group is replaced by an alternate blocking moiety B$^1$, as described above. The invention further provides compstatin analogs, having sequences as set forth in Table 1, but where the —NH$_2$ group is replaced by an alternate blocking moiety B$^2$, as described above.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., *Mol. Immunol.*, 35:160, 1998; Soulika, A. M., et al., *Mol. Immunol.* 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 1, e.g., SEQ ID NO: 14, 21, 28, 29, or 32 in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-32, e.g., SEQ ID NO: 14, 21, 28, or 32 in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 1, e.g., SEQ ID NO: 14, 21, 28, 29, or 32, or in other embodiments SEQ ID NO: 30 or 31.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, and/or WO2004026328. Potentially reactive moieties such as amino and carboxyl groups, reactive functional groups, etc., may be protected and subsequently deprotected using various protecting groups and methodologies known in the art. See, e.g., "Protective Groups in Organic Synthesis", 3$^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

Compstatin Mimetics

The structure of compstatin is known in the art, and NMR structures for a number of compstatin analogs having higher activity than compstatin are also known (Malik, supra). Structural information may be used to design compstatin mimetics.

In one embodiment, the compstatin mimetic is any compound that competes with compstatin or any compstatin analog (e.g., a compstatin analog whose sequence is set forth in Table 1) for binding to C3 or a fragment thereof (such as a 40 kD fragment of the β chain to which compstatin binds) and that has an activity equal to or greater than that of compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In embodiments the compstatin mimetic is a compound that binds to the binding site of a peptide having a sequence set forth in Table 1, e.g., SEQ ID NO: 14, 21, 28, 29, or 32, or in certain embodiments SEQ ID NO: 30 or 31, in a peptide-C3 structure. In certain embodiments the compstatin mimetic is a compound that could substitute for a peptide having a sequence set forth in Table 1, e.g., SEQ ID NO: 14, 21, 28, 29, or 32, or in certain embodiments SEQ ID NO: 30 or 31, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med. Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

The invention encompasses use of virtual screening methods to identify compstatin mimetics that bind to C3. Such methods may comprise use of suitable algorithms to computationally dock, score, and optionally rank a plurality of candidate structures. In one embodiment, an induced-fit algorithm is employed. In one embodiment, the invention provides a method comprising (i) providing a three-dimensional structure of C3 or a portion thereof to which compstatin binds; (ii) computationally docking a plurality of molecular structures with the structure of C3; and (iii) selecting a molecular structure that binds to substantially the same site as that to which a compstatin or an analog thereof binds. Any of a wide variety of available software programs can be used to perform the virtual screening method. Exemplary programs useful for flexible molecular docking include DOCK 4.0, FlexX 1.8, AutoDock 3.0, GOLD 1.2, ICM 2.8, and more recent versions thereof.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far.

Combination Therapies

The present invention contemplates the use of compstatin analogs and mimetics together with one or more other agents effective for treatment of the retinal and other ocular conditions discussed herein, e.g., one or more other complement inhibitors, angiogenesis inhibitors, etc. Suitable complement inhibitors include inhibitors of complement activation such as viral complement control proteins (VCCPs) (e.g., vaccinia complement control protein (VCP), smallpox inhibitor of complement (SPICE)), peptides, etc. The invention specifically contemplates use of any of the agents described in U.S. Ser. No. 60/616,983, filed Oct. 8, 2004, U.S. Ser. No. 60/660,752, filed Mar. 11, 2005, and U.S. patent application entitled VIRAL COMPLEMENT CONTROL PROTEINS FOR EYE DISORDERS, filed Oct. 8, 2005. These or other complement inhibitors may be administered together with compstatin or a complement inhibiting analog thereof as part of a single composition or the agents may be administered separately. The complement inhibitors may be administered sequentially or concurrently and may be administered by the same or different routes of administration. For example, certain agents may be more advantageously administered intravitreally and other agents may be more advantageously administered in close proximity to, but outside of, the posterior segment of the eye, e.g., behind the sclera.

In one embodiment, the invention provides a method comprising administering a compstatin analog and an angiogenesis inhibitor to a subject suffering from or at risk of developing wet ARMD. The compstatin analog and the angiogenesis inhibitor may be administered in either order. In one embodiment, an angiogenesis inhibitor such as an anti-VEGF antibody, aptamer, or siRNA (e.g., Lucentis, Avastin, Macugen) is administered by intravitreal injection using methods and amounts of angiogenesis inhibitor typically used in the art for treating wet ARMD. A compstatin analog is administered, e.g., by intravitreal injection, at a time up to 4 weeks following administration of the angiogenesis inhibitor, e.g., within 24, 48, or 72 hours after administration of the angiogenesis inhibitor, or within 1, 2, 3, or 4 weeks after administration of the angiogenesis inhibitor. In one embodiment the compstatin analog is administered after the subject has shown a favorable response to the angiogenesis inhibitor, e.g., a decrease in retinal thickness (measured, e.g., using optical coherence tomography) or an improvement in visual acuity. In one embodiment, the compstatin analog is administered in an ocular, e.g., intravitreal, insert. In another embodiment the compstatin analog is administered in a microparticle or nanoparticle formulation. In certain embodiments the compstatin analog is administered in an ocular insert or microparticle/nanoparticle formulation that contains between 100 and 10,000 µg of a compstatin analog. In certain embodiments the compstatin analog is administered in an ocular insert that contains between 100 and 1,000 µg of a compstatin analog, e.g., between 100 and 500 µg. In certain embodiments the compstatin analog is released from the insert of microparticle/nanoparticle formulation at a rate between 0.1 and 5 µg/day. In certain embodiments the compstatin analog is released from the insert of microparticle/nanoparticle formulation at a rate between 0.5 and 5 µg/day. In certain embodiments the compstatin analog is released from the insert of microparticle/nanoparticle formulation at a rate between 5 and 10 µg/day. In certain embodiments the compstatin analog is released from the insert of microparticle/nanoparticle formulation at a rate between 10 and 20 µg/day. One aspect of the invention comprises providing instructions to those of skill in the art, e.g., ophthalmologists, regarding methods for administering the compstatin analog and, optionally, a second therapeutic agent such as an angiogenesis inhibitor. The instructions may be provided together with, or separately from, one or more of the therapeutic agents.

Assessing Properties of Compstatin and Compstatin Analogs

Any suitable method can be used for assessing any of the properties of compstatin or an analog or mimetic thereof. A number of in vitro assays can be used. For example, ability of an agent to inhibit the classical or alternative complement pathway may be assessed by measuring complement-mediated hemolysis of erythrocytes (e.g., antibody-sensitized or unsensitized rabbit or sheep erythrocytes) by serum, e.g., human serum, plasma, or a set of complement components in the presence or absence of the agent. An agent inhibits complement if it decreases hemolysis in this inhibition assay to a statistically significant degree ($p<0.05$).

The ability of an agent to bind to one or more complement component such as C3 can be assessed using isothermal titration calorimetry or other methods suitable for performing in liquid phase. In another embodiment, the ability of an agent to bind to a complement component is measured using an ELISA assay. For example, the wells of a microtiter plate are coated with the agent. A compstatin analog or mimetic may be functionalized in order to facilitate binding it to a plate. For example, the agent could be biotinylated, and a streptavidin-coated plate is used. Complement component(s) are added to the wells. After a period of incubation the wells are washed, and bound complement components are detected using antibodies to the complement component of interest. Other methods of use include surface plasmon resonance, equilibrium dialysis, etc.

Certain of the foregoing methods are described in U.S. Pat. No. 6,319,897; PCT publication WO2004/026328 (PCT/US2003/029653), Morikis, D., et al., *Biochem Soc Trans.* 32(Pt 1):28-32, 2004, and Mallik, B., et al., *J. Med. Chem.*, 274-286, 2005. Any of these methods or variants thereof, or others known in the art, can be used. In one embodiment, the assay described in Example 4 or 5 is used.

Targeting Compstatin and Compstatin Analogs and Mimetics

The invention provides a composition comprising (i) compstatin or a complement inhibiting analog thereof; and (ii) a binding moiety that binds to a component present in the eye of a subject at risk of or suffering from a retinal disorder characterized by macular degeneration, choroidal neovascularization, or both, e.g., a macular degeneration related condition, diabetic retinopathy, or retinopathy of prematurity. The composition can be used to treat or prevent any of the foregoing disorders. Preferably the binding moiety and the compstatin or compstatin analog are linked. The linkage can be covalent or noncovalent and can be direct or indirect in various embodiments of the invention. The binding moiety can be, for example, an antibody or ligand, as discussed below. According to certain embodiments of the invention the component is a cellular marker. In other embodiments of the invention the component is a drusen constituent. The cellular marker can be any marker that is expressed on or at the surface of a cell, preferably an endothelial cell or retinal pigment epithelial cell. In certain embodiments of the invention the cellular marker is a cell type specific marker.

In general, the component can be any molecule present on or at the surface of a cell or noncellular molecular entity. By "on or at the surface of the cell or noncellular molecular entity" is meant that the component is accessible to molecules present in the extracellular environment so that it can be recognized and bound by the moiety. The component may be entirely extracellular. The component may be inserted into the cell membrane. In certain embodiments of the invention the component may be partly or entirely within the membrane, in which case the entity must partially penetrate the membrane to gain access. In general, the component is not located in the cytoplasm of a cell. As long as a sufficient portion of the component is exposed or accessible so that it can be recognized and bound, it will be said to be present on or at the surface. In preferred embodiments of the invention the component is a cellular marker, e.g., a cell type specific marker. Where the target is a molecular entity other than a cell, the component can be any chemical entity present on or at the surface of the molecule that is recognizable by an antibody or ligand.

A number of cellular markers that are expressed on or at the surface of endothelial cells and can be used to target compstatin or an analog thereof to endothelial cells in the eye (e.g., in the choroidal vasculature) are disclosed in U.S. Ser. No. 10/923,940. Tissue factor (TF), a molecule involved in hemostasis, is a preferred marker. Briefly, tissue factor is a cell membrane-bound glycoprotein (MW 46 kDa) and a member of the class 2 cytokine receptor family. It is composed of a hydrophilic extracellular domain, a membrane-spanning hydrophobic domain, and a cytoplasmic tail of 21 residues, including a non-disulfide-linked cysteine. Upon exposure to blood, perivascular cell-bound TF binds to factor VII (FVII), a vitamin K-dependent serine protease. TF is expressed on endothelial cells lining the luminal surface of various forms of pathological neovasculature, including pathological vasculature associated with the exudative (wet) form of age-related macular degeneration and diabetic retinopathy but typically is not expressed (or is expressed at a much lower level) in normal vasculature, thus providing a specific and accessible target. By linking a compstatin or a compstatin analog to factor VII or a derivative thereof, the compstatin or analog is targeted to cells that express TF, e.g., endothelial cells in pathological neovasculature. Integrin alpha(v) beta(3) is another preferred marker.

A number of markers are expressed on or at the surface of retinal pigment epithelial cells. These include, but are not limited to, CD68 antigen (Elner SG, *Exp Eye Res*. 1992 July; 55(1):21-8), claudin (Nishiyama K, et al., *Anat Rec*. 2002 Jul. 1; 267(3):196-203, the protein encoded by the RPE65 gene (Nicoletti A., et al., *Invest Ophthalmol Vis Sci*. 1998 March; 39(3):637-44), CD45 and ICAM-1 (Limb, G A, et al., *Curr Eye Res*. 1997 October; 16(10):985-91). See also Chowers, I., et al., Studies on retinal and retinal pigment epithelial gene expression, Novartis Found Symp. 2004; 255:131-45, 145-6, 177-8 for additional examples.

A large number of molecular components have been identified in drusen. Such components are suitable noncellular molecular entities to which compstatin or a compstatin analog can be targeted. These constituents include α1-antichymotrypsin, α1-antitrypsin, Alzheimer amyloid β peptide, advanced glycation end products, amyloid P component, apolipoproteins B and E, carbohydrate moieties recognized by various lectins, cholesterol esters, clusterin, complement factors, cluster differentiation antigen, complement receptor 1, factor X, heparan sulfate proteoglycan, human leukocyte antigen DR, immunoglobulin light chains, major histocompatibility complex class II antigens, membrane cofactor protein, peroxidized lipids, phospholipids and neutral lipids, tissue inhibitor of matrix metalloproeinases-3, transthyretin, ubiquitin, and vitronectin (Zarbin, M A, *Arch Ophthalmol*. 122:598-614, 2004). A number of these components are also found in deposits associated with a variety of different diseases including atherosclerosis.

In certain preferred embodiments of the invention the binding moiety is linked to compstatin or a complement inhibiting analog thereof. In other embodiments the binding moiety comprises a portion that binds to another molecule to which compstatin or an analog thereof is attached. Suitable binding moieties include antibodies that specifically bind to a cellular marker or noncellular molecular entity such as a drusen constituent and ligands that specifically bind to a cellular marker or noncellular molecular entity such as a drusen constituent. In general, the linkage between the binding moiety and the compstatin or a complement inhibiting analog thereof can be covalent or noncovalent and can be direct or indirect in various embodiments of the invention. Similarly, a moiety that binds to a noncellular marker such as a drusen constituent may be linked to compstatin or a complement inhibiting analog thereof or to another molecule to which compstatin or a complement inhibiting analog thereof is attached.

In those embodiments of the invention in which the binding moiety is an antibody, the antibody may be any immunoglobulin or a derivative thereof, which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. Monovalent, bivalent or multivalent antibodies can be used. The antibody may be a chimeric or "humanized" antibody in which, for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., (1998), *Nature Biotechnology*, 16: 535-539. The antibody may be partially or completely humanized. An antibody may be polyclonal or monoclonal, though for purposes of the present invention monoclonal antibodies are generally preferred. Preferably the antibody specifically binds to its target on the cell surface, e.g., to a cell-type specific marker. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture.

In certain embodiments of the invention it is preferable to use F(ab')2 or F(ab') fragments rather than antibodies that contain an Fc portion since the Fc portion may have a proinflammatory effect or cause other undesirable effects. However, in certain embodiments of the invention it is preferred to use antibodies comprising an Fc domain. F(ab')$_2$ fragments can be generated, for example, through the use of an Immunopure F(ab')$_2$ Preparation Kit (Pierce) in which the antibodies are digested using immobilized pepsin and purified over an immobilized Protein A column. The digestion conditions (such as temperature and duration) may be optimized by one of ordinary skill in the art to obtain a good yield of F(ab')$_2$. The yield of F(ab')$_2$ resulting from the digestion can be monitored by standard protein gel electrophoresis. F(ab') can be obtained by papain digestion of antibodies, or by reducing the S—S bond in the F(ab')$_2$.

In various embodiments of the invention an appropriate binding moiety to which compstatin or a complement inhibiting analog thereof is linked can be any molecule that specifically binds to a target molecule (e.g., polypeptide or a portion thereof such as a carbohydrate moiety), through a mechanism other than an antigen-antibody interaction. Such a binding moiety is referred to as a "ligand". For example, in various embodiments of the invention a ligand can be a polypeptide, peptide, nucleic acid (e.g., DNA or RNA), carbohydrate, lipid or phospholipid, or small molecule (e.g., an organic compound, whether naturally-occurring or artificially created that has relatively low molecular weight and is not a protein, polypeptide, nucleic acid, or lipid, typically with a molecular weight of less than about 1500 g/mol and typically having multiple carbon-carbon bonds).

Ligands may be naturally occurring or synthesized, including molecules whose structure has been invented by man. Examples of ligands include, but are not limited to, hormones, growth factors, or neurotransmitters that bind to particular receptors. For example, Factor VII is a ligand for TF. Exemplary TF binding moieties are FVII, activated FVII (FVIIa), inactive FVIIa, antibodies that bind to tissue factor, engineered polypeptides, aptamers, and small molecules that bind to tissue factor. Inactive FVII or inactive FVIIa is a derivative of FVII or FVIIa that is catalytically inactivated in the active site, e.g., by derivatization with an inhibitor. Many irreversible serine protease inhibitors, which generally form covalent bonds with the protease active site, are known in the art. Examples of suitable inhibitors include peptide halomethyl ketones, e.g., peptide chloromethyl ketones (see, Williams et al., *J. Biol. Chem.* 264:7536-7540, 1989 and U.S. Pat. No. 5,817,788). In some embodiments FVII or FVIIa activity is inhibited by substitution, deletion, and/or insertion of one or more amino acids in FVII. Generally, the substitution(s), insertion(s), and/or deletion(s) are made at or adjacent to a catalytic site residue. In certain embodiments, the alteration(s) is a substitution or deletion of Ser344, Asp242, and/or His193. As mentioned above, TF binds to factor VII that is normally present in the blood. Thus according to one embodiment of the invention compstatin analog is linked to a TF binding moiety. The binding moiety binds to TF, present on endothelial cells in choroidal neovasculature, thereby providing an increased amount of the compstatin analog at the cell surface and preventing additional complement activation.

It will also be appreciated that fragments or variants of the above-mentioned polypeptide ligands differing in sequence from their naturally occurring counterparts but retaining the ability to bind to endothelial cells or retinal pigment epithelial cells can also be used. In certain embodiments of the invention, a polypeptide ligand contains 5 or fewer amino acid differences, 10 or fewer amino acid differences, 25 or fewer amino acid differences, 50 or fewer amino acid differences, or 100 or fewer amino acid differences with respect to its naturally occurring counterpart. In certain embodiments of the invention the number of amino acid differences between a naturally occurring polypeptide ligand and a fragment or variant thereof for use in the invention is 5% or less, 10% or less, or 25% or less of the total number of amino acids in the naturally occurring polypeptide.

In certain embodiments of the invention a fragment or variant of a naturally occurring polypeptide ligand is at least 70% identical, at least 80% identical, at least 90% identical, at least 95% identical, over an amino acid portion that constitutes at least 10%, at least 20%, at least 30%, at least 40%, at least 50%, at least 60%, at least 70%, at least 80%, or at least 90%, or 100% of the length of the naturally occurring counterpart. For example, variant that exhibits at least 50%, at least 60%, at least 70%, at least 80%, at least 90%, or greater sequence identity, over the relevant portion of the sequence could be used, wherein % identity is determined as described above. The amino acid portion is preferably at least 20 amino acids in length, more preferably at least 50 amino acids in length. Alternately, a fragment or variant can display significant or, preferably, substantial homology to a naturally occurring counterpart. Generally a fragment or variant of a naturally occurring polypeptide ligand possesses sufficient structural similarity to its naturally occurring counterpart that it is recognized by an antibody (e.g., a polyclonal or monoclonal antibody) that recognizes the naturally occurring counterpart. Peptide ligands can be identified using phage display (Arap W, et al, *Nature Medicine* 8(2):121-7, 2002); Zurita AJ, et al., *J Control Release,* 91(1-2):183-6, 2003; Pasqualini, R. & Ruoslahti, E. *Nature* 380, 364-366, 1996; Pasqualini, R., et al., *Trends Mol. Med.* 8, 563-571, 2002).

In certain embodiments of the invention the ligand is an aptamer that binds to a cell type specific marker. In general, an aptamer is an oligonucleotide (e.g., DNA or RNA or) that binds to a particular protein. Aptamers are typically derived from an in vitro evolution process called SELEX, and methods for obtaining aptamers specific for a protein of interest are known in the art. See, e.g., Brody E N, Gold L. *J Biotechnol.* 2000 March; 74(1):5-13.

Small molecules can also be used as ligands. Methods for identifying such ligands are known in the art. For example in vitro screening of small molecule libraries, including combinatorial libraries, and computer-based screening, e.g., to identify small organic compounds that bind to concave surfaces (pockets) of proteins, can identify small molecule ligands for numerous proteins of interest (Huang, Z., *Pharm. & Ther.* 86: 201-215, 2000).

In certain embodiments of the invention binding moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In certain embodiments of the invention the cell binding moiety is not an Fc portion of an immunoglobulin molecule.

Methods for covalently or noncovalently linking a compstatin analog to a binding moiety are known in the art and are described in U.S. Ser. No. 10/923,940. General methods for conjugation and cross-linking are described in "Cross-Linking", Pierce Chemical Technical Library, available at the Web site having URL www. followed immediately by piercenet-.com and originally published in the 1994-95 Pierce Catalog and references cited therein, in Wong S S, *Chemistry of Protein Conjugation and Crosslinking*, CRC Press Publishers, Boca Raton, 1991; and G. T. Hermanson, supra. See also, Allen, T. M., *Nature Reviews Cancer,* 2, 750-763, 2002, which describes methods of making targeted therapeutic agents. For example, according to certain embodiments of the invention a bifunctional crosslinking reagent is used to couple a compstatin analog with an antibody or ligand. In general, bifunctional crosslinking reagents contain two reactive groups, thereby providing a means of covalently linking two target groups. The reactive groups in a chemical crosslinking reagent typically belong to various classes including succinimidyl esters, maleimides, pyridyldisulfides, and iodoacetamides. Bifunctional chelating agents may also be used.

Alternately, the compstatin analog and the moiety can be produced as a fusion protein. Thus the invention provides a fusion protein comprising: (i) a first domain comprising a compstatin analog; and (ii) a second domain comprising a binding moiety that binds to a cellular marker or noncellular molecular entity present in the eye of a subject suffering from or at risk of a macular degeneration related condition or CNV. The first domain may be at the N or C terminus of the fusion protein. The fusion protein may contain one or more additional domains at either the N or C terminus or between the first and second domains. The fusion protein can contain multiple regions having the sequence of the compstatin analog, e.g., the fusion protein can comprise a concatamer of the compstatin analog. Optionally the different compstatin analog units are separated by a spacer, which may comprise a cleavage site for an enzyme (e.g., a protease) or chemical such as hydrazine. Also provided are nucleic acids encoding the fusion protein, expression vectors comprising the nucleic acid, host cells that contain the expression vector, and transgenic animals and plants containing the nucleic acid in their genome.

Targeted versions of a compstatin analog, and novel compstatin analogs and mimetics provided herein can be used for treatment of a number of conditions other than macular degeneration related conditions, diabetic retinopathy, RNV, CNV, ocular inflammation, etc. Such methods of treatment are an aspect of this invention. For such purposes the binding moiety need not bind to a site in the eye. In general, the binding moiety is selected to target the complement inhibiting protein to any site in the body at which complement inhibition is desired. For example, the compounds can be used to treat atherosclerosis, Alzheimer's disease, CNS injury (including spinal cord injury), transplant rejection, or any other disease in which complement activation plays a role (e.g., certain forms of glomerulonephritis, certain inflammatory conditions), etc. They can be used to prevent complement activation during cardiac bypass surgery or ischemia/reperfusion in myocardial infarction or stroke. In one embodiment, a compstatin analog or mimetic is used to treat chronic pain. Atherosclerotic plaques, organ transplants (e.g., xenotransplants, allotransplants, etc.) may be targeted. The targeted compositions can also be used in vitro, e.g., to treat platelets (which are considered cells for purposes of the invention) or other blood preparations in order to inhibit complement, or to treat organs prior to transplantation. Appropriate binding moieties, e.g., cell binding moieties or moieties that bind to a component in an atherosclerotic plaque, an Alzheimer's disease plaque (e.g., β-amyloid), etc. are used to target the compstatin or a complement inhibiting analog thereof to the plaque. A Gal (1,3-Gal) epitope on the surface of a transplanted organ can be targeted.

Additional Modifications

Compstatin or an analog thereof, optionally linked to a binding moiety, can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458 (2002; Hinds, K. D. & Kim, S. W. *Adv. Drug Deliv. Rev.* 54, 505-530 (2002; Roberts, M. J., Bentley, M. D. & Harris, J. M. *Adv. Drug Deliv. Rev.* 54, 459-476 (2002; Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. In another embodiment compstatin or a compstatin analog is fused to the Fc domain of an immunoglobulin or a portion thereof. Thus in some embodiments compstatin or a complement inhibiting analog thereof is modified with one or more polypeptide or non-polypeptide components, e.g., the compstatin or analog is pegylated or conjugated to another moiety. In some embodiments the component is not the Fc domain of an immunoglobulin or a portion thereof. Compstatin and/or a compstatin analog can be provided as multimers or as part of a supramolecular complex, which can include either a single molecular species or multiple different species (e.g., multiple different analogs).

The invention provides a multivalent compound comprising a plurality of compstatin analog moieties covalently or noncovalently linked to a polymeric backbone or scaffold. The compstatin analog moieties may be the same or different compstatin analog. The invention further provides a compstatin analog comprising a reactive functional group or comprising a linker comprising a reactive functional group, wherein the reactive functional group facilitates the attachment of the compstatin analog to the polymeric backbone. The compstatin analog can be any of the compstatin analogs described herein. It will be appreciated that following attachment to the polymeric backbone, the structure of the compstatin analog moiety will differ slightly from that of the compstatin analogs described herein. For example, a compstatin analog molecule comprising an amine ($NH_2$) group, represented as $NH_2$—$R^1$, may react with a moiety comprising a carboxylic acid (COOH), represented as $R^2$—(C═O)OH to form a conjugate having formula $R^2$—(C═O)—NH—$R^1$, in which one of the hydrogens present in the compstatin analog is no longer present and a new covalent bond (C—N) has been formed. Thus the term "compstatin analog moiety" includes molecules having the precise formula of a compstatin analog as described herein as well as molecular structures in which a functional group of a compstatin analog has reacted with a second functional group, which typically entails loss of at least one atom or group of atoms that was present in the compstatin analog molecule prior to the reaction and formation of a new covalent bond. The new covalent bond is formed between an atom that was previously attached to one of the atoms that is lost from the compstatin analog and an atom to which the compstatin analog becomes attached.

The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two of more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In one embodiment, the compstatin analog comprises an amino acid having a side chain comprising a primary or secondary amine, e.g., a Lys residue. For example, a Lys residue, or a sequence comprising a Lys residue, is added at the C-terminus of the compstatin analog. In one embodiment, the Lys residue is separated from the cyclic portion of the compstatin analog by a rigid or flexible spacer. The spacer may, for example, be a substituted or unsubstitued, saturated or unsaturated alkyl chain. The length of the alkyl chain may be, e.g., between 2 and 20 carbon atoms. In other embodiments the spacer is a peptide. The peptide spacer may be, e.g., between 1 and 20 amino acids in length, e.g., between 4 and 20 amino acids in length. Suitable spacers comprise or consist of multiple Gly residues, Ser residues, or both.

Any of a variety of polymeric backbones or scaffolds could be used. For example, the polymeric backbone or scaffold may be a polyamide, polysaccharide, polyanhydride, polyacrylamide, polymethacrylated, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

Pharmaceutical Compositions and Delivery Vehicles and Methods

Suitable preparations, e.g., substantially pure preparations of the compstatin analog or mimetic, or any of the compounds described above, may be combined with pharmaceutically acceptable carriers, diluents, solvents, etc., to produce an appropriate pharmaceutical composition. Such pharmaceutical compositions are an aspect of the invention. The invention further provides a pharmaceutically acceptable composition comprising (i) a compstatin analog linked to a moiety that binds to a component present on or at the surface of a cell or noncellular molecular entity; and (ii) a pharmaceutically acceptable carrier or vehicle. The moiety may be an antibody or ligand. The component may be a marker such as a cell type specific marker for RPE or endothelial cells, a drusen constituent, etc.

In certain embodiments of the invention the pharmaceutical composition detectably inhibits neovascularization in an eye, following administration to a subject. In other words, administration of the compound measurably reduces neovascularization relative to the expected level in the absence of the composition. In certain embodiments of the invention the pharmaceutical composition detectably inhibits development or progression of geographic atrophy and/or drusen formation in an eye, following administration to a subject. In other words, administration of the compound measurably reduces development or progression of geographic atrophy and/or drusen formation relative to the expected level in the absence of the composition. In certain embodiments the composition inhibits increase in retinal thickness (e.g., as measured by OCT) associated with the disease (e.g., the wet type of ARMD). In certain embodiments of the invention the pharmaceutical composition detectably inhibits vision loss in an eye, following administration to a subject. In other words, administration of the compound measurably reduces vision loss relative to the expected level in the absence of the composition. In certain embodiments of the invention the pharmaceutical composition detectably inhibits inflammation in an eye, following administration to a subject. In other words, administration of the compound measurably reduces inflammation relative to the expected level in the absence of the composition. It is to be understood that the pharmaceutical compositions of the invention, when administered to a subject, are preferably administered for a time and in an amount sufficient to treat or prevent the disease or condition for whose treatment or prevention they are administered. A useful pharmaceutical composition may provide one or more than one of the afore-mentioned beneficial effects.

Further of use in the invention are pharmaceutically acceptable compositions comprising a pharmaceutically acceptable derivative (e.g., a prodrug) of compstatin or a complement inhibiting analog thereof, by which is meant any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also able to detectably inhibit complement, e.g., inhibit complement activation.

In various embodiments of the invention an effective amount of the pharmaceutical composition is administered to a subject by any suitable route of administration including, but not limited to, intravenous, intramuscular, by inhalation, by catheter, intraocularly, orally, rectally, intradermally, by application to the skin, by eyedrops, etc. When a composition of the invention is used to treat an ophthalmic condition it will be appreciated that administration to the eye to or in the vicinity of the eye, may be preferred. In certain embodiments of the invention the intravenous route is used. For example, a compstatin analog may be administered in a solid implant, or in a microparticle or nanoparticle formulation, whereby it is protected from clearance and/or degradation in the bloodstream.

Inventive compositions may be formulated for delivery by any available route including, but not limited to parenteral, oral, by inhalation to the lungs, nasal, bronchial, ophthalmic, transdermal (topical), transmucosal, rectal, and vaginal routes. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered either locally to the eye or intravenously.

The term "pharmaceutically acceptable carrier or vehicle" refers to a non-toxic carrier or vehicle that does not destroy the pharmacological activity of the compound with which it is formulated. Pharmaceutically acceptable carriers or vehicles that may be used in the compositions of this invention include, but are not limited to, water, physiological saline, and the like.

The composition may include other components as appropriate for the formulation desired, e.g., buffer substances such as phosphates, glycine, sorbic acid, potassium sorbate, partial glyceride mixtures of saturated vegetable fatty acids, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$(C1-4 alkyl)4 salts. This invention also envisions the quaternization of any basic nitrogen-containing groups of the compounds disclosed herein. Water or oil-soluble or dispersible products may be obtained by such quaternization.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, dimethyl sulfoxide (DMSO), fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In general, the composition should be sterile, if possible, and should be fluid so that easy syringability exists.

Preferred pharmaceutical formulations are stable under the conditions of manufacture and storage and may be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present invention also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For local delivery to the eye, the pharmaceutically acceptable compositions may be formulated in isotonic, pH adjusted sterile saline or water, either with or without a preservative such as benzylalkonium chloride. Alternatively, for ophthalmic uses, the pharmaceutically acceptable compositions may be formulated in an ointment such as petrolatum or as eyedrops.

Methods of local administration to the eye include, e.g., choroidal injection, transscleral injection or placing a scleral patch, selective arterial catheterization, eyedrops or eye ointments, intraocular administration including transretinal, subconjunctival bulbar, intravitreous injection, suprachoroidal injection, subtenon injection, scleral pocket and scleral cutdown injection, by osmotic pump, etc. The agent can also be alternatively administered intravascularly, such as intravenously (IV) or intraarterially. In choroidal injection and scleral patching, the clinician uses a local approach to the eye after initiation of appropriate anesthesia, including painkillers and ophthalmoplegics. A needle containing the therapeutic compound is directed into the subject's choroid or sclera and inserted under sterile conditions. When the needle is properly positioned the compound is injected into either or both of the choroid or sclera. When using either of these methods, the clinician can choose a sustained release or longer acting formulation. Thus, the procedure can be repeated only every several months or several years, depending on the subject's tolerance of the treatment and response.

Intraocular administration of drugs intended for treatment of macular degeneration and other intraocular conditions is well known in the art. See, e.g., U.S. Pat. Nos. 5,632,984 and 5,770,589. U.S. Pat. No. 6,378,526 provides methods for intrascleral injection of a therapeutic or diagnostic material at a location overlying the retina, which provide a minimally invasive technique for delivering the agent to the posterior segment of the eye.

In certain embodiments of the invention a composition is delivered to the vicinity of the eye, e.g., in close proximity to the posterior segment of the eye. The "vicinity of the eye" refers to locations within the orbit, which is the cavity within the skull in which the eye and its appendages are situated. Typically the compositions would be delivered close to their intended target within the eye, e.g., close to (within several millimeters of) the portion of the sclera that overlies the posterior segment of the eye, or immediately adjacent to the exterior surface of the sclera.

A number of polymeric delivery vehicles for providing controlled release have been used in an ocular context and can be used to administer the compositions of the invention. Various polymers, e.g., biocompatible polymers, which may be biodegradable, can be used. For example, U.S. Pat. No. 6,692,759 describes methods for making an implantable device for providing controlled release of therapeutic agents in the eye. Other useful polymers and delivery systems for ocular administration of a therapeutic agent have been described. The active agent may be released as the polymer degrades. Polymers that have been used for drug delivery include, but are not limited to, poly(lactic-co-glycolic acid), polyanhydrides, ethylene vinyl acetate, polyglycolic acid, chitosan, polyorthoesters, polyethers, polylactic acid, and poly (beta amino esters). Peptides, proteins such as collagen and albumin, and dendrimers (e.g., PAMAM dendrimers) have also been used. Any of these can be used in various embodiments of the invention.

Poly(ortho esters) have been introduced into the eye and demonstrated favorable properties for sustained release ocular drug delivery (Einmahl, S., *Invest. Ophthalmol. Vis. Sci.*, 43(5), 2002). Polylactide particles have been used to target an agent to the retina and RPE following intravitreous injection of a suspension of such particles (Bourges, J-L, et al, *Invest. Ophthalmol. Vis. Sci.*, 44(8), 2003). A macroscopic implantable device suitable for introduction into the posterior or anterior segment of the eye is referred to herein as an ocular implant (Jaffe, G., *Invest. Ophthalmol. Vis. Sci.*, 41(11), 2000; Jaffe, G., *Ophthalmology*). The invention provides an ocular implant comprising a compstatin analog, e.g., in an amount effective to treat an eye disorder such as ARMD. Such devices may be macroscopic implants comprising the agent or may be comprised of a plurality of nanoparticles or microparticles impregnated with or encapsulating the agent. In one embodiment, the ocular implant is any ocular implant known in the art. Exemplary implants and methods for manufacture thereof are described, e.g., in provisional patent application entitled "Injectable Combination Therapy for Eye Disorders" (U.S. Ser. No. 60/760,974) filed Jan. 19, 2006. Other implants known in the art can also be used. In certain embodiments the implant comprises between 100 and 2000 µg of a compstatin analog, e.g., between 100 and 1000 µg, e.g., between 100 and 500 µg.

Methods for making microparticles and nanoparticles are known in the art. Generally, a microparticle will have a diameter of 500 microns or less, e.g., between 50 and 500 microns, between 20 and 50 microns, between 1 and 20 microns, between 1 and 10 microns, and a nanoparticle will have a diameter of less than 1 micron. Preferably the device is implanted into the space occupied by the vitreous humor. The ocular implant may comprise a polymeric matrix. The invention also provides periocular implants, which are macroscopic implantable device suitable for introduction in the vicinity of the eye, e.g., in close proximity to the eye. In certain embodiments the periocular implant is made of similar materials to those described above.

Cells that express compstatin or a complement inhibiting analog thereof can be implanted into the eye. U.S. Pat. No. 6,436,427 provides a method for delivering biologically active molecules to the eye by implanting biocompatible capsules containing a cellular source of the biologically active molecule.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In addition to the agents described above, in certain embodiments of the invention, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. Certain of the materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811 and other references listed herein. Liposomes, including targeted liposomes (e.g., antibody targeted liposomes) and pegylated liposomes have been described (Hansen CB, et al., *Biochim Biophys Acta.* 1239(2):133-44, 1995; Torchilin V P, et al., *Biochim Biophys Acta,* 1511(2): 397-411, 2001; Ishida T, et al., *FEBS Lett.* 460(1):129-33, 1999). One of ordinary skill in the art will appreciate that the materials and methods selected for preparation of a controlled release formulation, implant, etc., should be such as to retain activity of the compound. For example, it may be desirable to avoid excessive heating of polypeptides, which could lead to denaturation and loss of activity.

The invention also encompasses gene therapy, in which a nucleic acid that encodes compstatin or a complement inhibiting analog thereof in operable association with expression control signals, e.g., regulatory elements such as a promoter, terminator, polyadenylation signal, etc., sufficient to direct expression of the fragment or variant is introduced into a subject. The nucleic acid may encode a fusion protein comprising compstatin or a complement inhibiting analog thereof. Nucleic acids can be introduced into a subject by any of a number of methods. For instance, a pharmaceutical preparation of a nucleic acid therapeutic can be introduced systemically, e.g., by intravenous injection. Expression of the polypeptide in particular target cells may result from specificity of transfection provided by the vector, cell-type or tissue-type expression due to the transcriptional regulatory sequences controlling expression of the gene, or a combination thereof. Alternatively, initial delivery of the nucleic acid can be more limited. For example, the vector can be locally introduced into the eye using any of the methods described above for ocular administration.

A pharmaceutical composition comprising a nucleic acid therapeutic of the invention can consist essentially of the nucleic acid or a gene therapy vector comprising in an acceptable diluent, or can comprise a slow release matrix in which the nucleic acid or gene therapy vector is encapsulated or embedded. The gene therapy vector can be a plasmid, virus, or other vector. Alternatively, the pharmaceutical composition can comprise one or more cells which produce a therapeutic nucleic acid or polypeptide such as compstatin or a complement inhibiting analog thereof. Preferably such cells secrete the peptide into the extracellular space or bloodstream.

Viral vectors that have been used for gene therapy protocols include, but are not limited to, retroviruses, lentiviruses, other RNA viruses such as poliovirus or Sindbis virus, adenovirus, adeno-associated virus, herpes viruses, SV 40, vaccinia and other DNA viruses. Replication-defective murine retroviral or lentiviral vectors are widely utilized gene transfer vectors. Chemical methods of gene therapy involve carrier-mediated gene transfer through the use of fusogenic lipid vesicles such as liposomes or other vesicles for membrane fusion. A carrier harboring a nucleic acid of interest can be conveniently introduced into the eye or into body fluids or the bloodstream. The carrier can be site specifically directed to the target organ or tissue in the body. Cell or organ-specific DNA-carrying liposomes, for example, can be developed and the foreign nucleic acid carried by the liposome absorbed by those specific cells. Carrier mediated gene transfer may also involve the use of lipid-based compounds which are not liposomes. For example, lipofectins and cytofectins are lipid-based compounds containing positive ions that bind to negatively charged nucleic acids and form a complex that can ferry the nucleic acid across a cell membrane. Cationic polymers are known to spontaneously bind to and condense nucleic acids such as DNA into nanoparticles. For example, naturally occurring proteins, peptides, or derivatives thereof have been used. Synthetic cationic polymers such as polyethylenimine (PEI), polylysine (PLL) etc., are also known to condense DNA and are useful delivery vehicles. Dendrimers can also be used.

Many of the useful polymers contain both chargeable amino groups, to allow for ionic interaction with the negatively charged DNA phosphate, and a degradable region, such as a hydrolyzable ester linkage. Examples of these include poly(alpha-(4-aminobutyl)-L-glycolic acid), network poly (amino ester), and poly (beta-amino esters). These complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid. It has been proposed that such agents may act as a "proton sponge" within the endosome.

It is typically advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments.

Exemplary doses include milligram or microgram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

The invention further provides pharmaceutical compositions comprising two or more molecular species of the invention, each comprising a moiety that binds to a cellular marker on noncellular molecular entity, wherein the binding moieties in each molecular species bind to a different cellular marker. The invention further provides pharmaceutical compositions comprising one or more molecular species of the invention and an additional active agent. The additional active agent may be an agent that is effective for treatment of a macular degeneration related condition, diabetic retinopathy, or CNV. In certain embodiments of the invention the additional active agent is selected from the group consisting of: angiogenesis inhibitors, antiinflammatory agents, antiangiogenic steroids, and growth factors. Angiogenesis inhibitors are discussed further below. The additional active agent can be an antibiotic or an antiinflammatory agent not necessarily effective specifically for treatment of a macular degeneration related condition, diabetic retinopathy, or CNV.

Angiogenesis Inhibitors

Certain embodiments of the present invention make use of one or more angiogenesis inhibitors. Angiogenesis inhibitors can be divided into several groups based on their primary mechanism of action. One group includes cytotoxic agents that damage or kill target cells (e.g., endothelial cells) or that trigger an immune-mediated response that results in damage to or killing of target cells. A second group includes agents that do not substantially damage or kill endothelial cells but instead inhibit their proliferation, migration, capillary tube formation, or other processes associated with angiogenesis. Angiogenesis inhibitors falling into either or both of these groups can be used.

Angiogenesis inhibitors include, but are not limited to, Macugen® or another VEGF nucleic acid ligand; Lucentis®, Avastin®, or another anti-VEGF antibody; combretastatin or a derivative or prodrug thereof such as Combretastatin A4 Prodrug (CA4P); VEGF-Trap; EVIZON™ (squalamine lactate); AG-013958 (Pfizer, Inc.); JSM6427 (Jerini A G); a short interfering RNA (siRNA) that inhibits expression of one or more VEGF isoforms (e.g., $VEGF_{165}$); and an siRNA that inhibits expression of a VEGF receptor (e.g., VEGFR1). Other angiogenesis inhibitors include various endogenous or synthetic peptides such as angiostatin, arresten, canstatin, combstatin, endostatin, thrombospondin, and tumstatin. Other antiangiogenic molecules include thalidomide and its antiangiogenic derivatives such as iMiDs (Bamias A, Dimopoulos MA. Eur J Intern Med. 14(8):459-469, 2003; Bartlett JB, Dredge K, Dalgleish AG. *Nat Rev Cancer.* 4(4): 314-22, 2004). β2-glycoprotein 1 (β2-GP1) is an angiogenesis inhibitor of particular interest in the present invention.

Macugen (Pfizer, Eyetech) is a VEGF nucleic acid ligand (also referred to as an aptamer) that binds to and inhibits $VEGF_{165}$ (U.S. Pat. No. 6,051,698). Lucentis (Genentech) is a humanized antibody fragment that binds and inhibits Vascular Endothelial Growth Factor A (VEGF-A). (Gaudreault, J., et al., *Invest Ophthalmol. Vis. Sci.* 46, 726-733 (2005) and references therein. Avastin (Genentech) is a full length humanized antibody that also binds to VEGF. Cand5 (Acuity Pharmaceuticals, Philadelphia, Pa.) is a short interfering RNA (siRNA) designed to inhibit expression of VEGF. sima-027 (Sima Therapeutics; Boulder Colo.) is a chemically modified siRNA designed to inhibit expression of the VEGF receptor known as VEGFR1.

Compositions Comprising Compstatin or a Complement Inhibiting Analog Thereof and a Gel-Forming Material The invention provides a variety of compositions comprising a gel-forming material and a therapeutic agent, wherein said therapeutic agent is effective for treating a retinal disorder characterized by macular degeneration, CNV, or both. In various embodiments of the invention the therapeutic agent is a compstatin analog. The composition may comprise one or more additional therapeutic agents effective for treating the retinal disorder. Suitable agents are described elsewhere herein. In certain embodiments the gel-forming material is soluble, e.g., in an aqueous medium.

The invention encompasses the recognition that gel-forming compositions comprising a soluble collagen are useful for the delivery of therapeutic agents such as peptides or peptidomimetics to the posterior segment of the eye. The collagen is initially soluble and forms a solution that has a low viscosity but is capable of rapid formation of a gel under appropriate conditions, e.g., conditions encountered upon administration to a mammalian subject. The invention therefore provides a system for delivery of peptides or peptidomimetics to the posterior segment of the eye for treatment of eye disorders. The system is designed to localize such molecules in sufficient concentration to provide sustained delivery while at the same time allowing the macromolecule to be released in sufficient amounts so that it can diffuse to a site of action in the posterior segment of the eye, e.g., the retina, RPE, subretinal space, Bruch's membrane, and/or choriocapillaris. In addition, the collagen gel may protect the peptides or peptidomimetics from degradation, e.g., by endogenous proteases.

In addition to their use for delivering peptides and peptidomimetics such as compstatin and analogs thereof, a variety of biological macromolecules useful for the treatment of eye disorders characterized by macular degeneration, CNV, RNV, ocular inflammation, or any combination of the foregoing, can be delivered using the collagen compositions of the invention. Any of the agents mentioned herein, e.g., angiogenesis inhibitors such as Macugen, Lucentis, etc., can be delivered either singly or in combination with one or more other agents. The collagen compositions can also be used to deliver agents that are not biological macromolecules. The invention therefore provides a composition comprising: (i) a therapeutic agent effective for the treatment of an eye disorder characterized by macular degeneration, CNV, RNV, ocular inflammation, or any combination of the foregoing; and (ii) a soluble gel-forming material. In certain embodiments of the invention the agent is a complement inhibitor, e.g., a viral complement control protein (VCCP) or viral complement inhibiting protein (VCIP). As noted above, VCCPs and VCIPs are discussed in copending U.S. patent application entitled VIRAL COMPLEMENT CONTROL PROTEINS FOR EYE DISORDERS, filed Oct. 8, 2005. VCCPs include, but are not limited to, vaccinia complement control protein (VCP), smallpox inhibitor of complement protein (SPICE), and complement inhibiting fragments and variants thereof, e.g., fragments that contain at least four short consensus repeats. The complement inhibitor may, but need not be, a polypeptide or peptide. The composition forms a gel following introduction into the body, e.g., upon contact with a physiological fluid. The composition can also form a gel upon contact with a fluid such as phosphate buffered saline, or other fluid containing appropriate ions. Thus the composition can be injected at an appropriate location, e.g., in close proximity to the posterior segment of the eye, where it forms a gel. Alternately, a preshaped gel implant can be made, e.g., by introducing the solution into a mold or cavity of the desired shape and allowing gel formation to occur in the presence of a suitable concentration of a salt. The salt can be added either prior to or following the introduction of the solution into the mold or cavity. The mold or cavity can be, e.g., any structure that contains a hollow space or concave depression into which a solution can be introduced. In another embodiment, a film or membrane is formed from the collagen solution containing a therapeutic agent.

Release of the agent from the gel can occur by any mechanism, e.g., by diffusion of the agent out of the gel, as a result of breakdown of the gel, or both. One aspect of the invention is the selection of suitable concentrations of soluble collagen and collagen solids that result in a gel that retains the agent within the gel so as to provide sustained delivery for a desired period of time while also permitting release of the agent from the gel in sufficient concentration to be effective at its site of action in the posterior segment of the eye.

In accordance with certain embodiments of the invention, a solution containing the soluble collagen and a therapeutic agent is prepared by combining the soluble collagen and therapeutic agent in solution using any suitable method, e.g., by adding the therapeutic agent to a solution containing soluble collagen. The composition is delivered locally to an appropriate location in or near the eye of a mammalian subject, typically to an area outside of and in close proximity to the posterior segment of the eye. The solution rapidly forms a gel at or close to of the site of administration. The therapeutic agent is entrapped within the gel. The therapeutic agent diffuses out of the gel or is released as the gel degrades over time, thereby providing a continuous supply of the agent to tissues and structures that are either in direct physical contact with the gel or located nearby. In certain embodiments the solution is administered behind the sclera of the eye, as discussed further below. Delivery can be accomplished by injection (e.g., using a 30 gauge needle or the like), by catheter, etc., as further described below.

A variety of different collagen preparations can be used in the present invention provided that the collagen is initially soluble and is capable of rapidly forming a gel under appropriate conditions. Suitable collagen preparations, and methods for their manufacture, are described, e.g., in U.S. Pat. Nos. 5,492,135; 5,861,486; 6,197,934; 6,204,365; and WO 00/47130, but the invention is not limited to such preparations or methods. These collagens are prepared in soluble form and rapidly form a gel upon exposure to physiological fluids or other fluids having suitable concentration of ions. In accordance with the present invention, injecting or otherwise introducing the collagen solution to the eye or near the eye results in gel formation, presumably induced by contact with physiological fluids. However it is noted that the invention is in no way limited by the mechanism by which gel formation occurs. In addition, as noted above, the gel can be formed in vitro and them implanted at an appropriate location, e.g., in close proximity to the posterior segment of the eye.

One suitable method of preparing a soluble collagen solution involves extracting collagen from a natural source, acid solubilizing the collagen, and dialyzing the solubilized collagen against a solution containing a chelating agent, e.g., a metal chelating agent such as ethylenediamine tetraacetic acid, disodium salt dihydrate (EDTA), while raising the pH. One or more dialysis steps against a solution such as deionized water lacking the chelating agent may also be performed. Unlike standard collagen solutions that undergo spontaneous fibrillogenesis at neutral pH and room temperature, collagen solutions for use in the present invention remain in solution during storage for extended periods of time and rapidly undergo gel formation when exposed to physiological fluids. While not wishing to be bound by any theory, the chelating agent may alter the concentration of one or more cations and thereby prevent fibrillogenesis that would otherwise occur as the pH is raised. The chelating agent may have other desirable effects on the collagen solution, and in certain embodiments of the invention the collagen solution comprises a chelating agent, e.g., EDTA. The chelating agent may remain in the collagen solution following dialysis or may be added to the collagen solution. The concentration of the chelating agent may range, for example, between about 0.02M and about 0.05M, e.g., between about 0.025M and about 0.035M. Other chelating agents may also be used including, but not limited to, those described in U.S. Pat. No. 5,861,486.

In certain embodiments the collagen solution has a concentration of soluble collagen ranging between 1 mg/ml and 100 mg/ml, e.g., between 10 mg/ml and 70 mg/ml, between 20 mg/ml and 50 mg/ml, e.g., 30 mg/ml, etc. In certain embodiments of the invention the pH of the collagen solution is between 6.0 and 8.0, e.g., between 6.5 and 7.5, e.g., 7.0.

In certain embodiments of the invention the collagen composition further comprises a fibrillar component comprising fibrillar collagen solids. For example, certain collagen compositions contain between 0.5 mg/ml and 30 mg/ml fibrillar collagen solids, or between 1 mg/ml and 20 mg/ml fibrillar collagen solids, e.g., 2 mg/ml, 3 mg/ml, 4 mg/ml, 5 mg/ml, 6 mg/ml, 8 mg/ml, 10 mg/ml, etc. In terms of percent fibrillar collagen solids on a weight/volume basis, certain collagen compositions contain between 0.05 and 3% fibrillar collagen solids or between 0.1 and 2% fibrillar collagen solids, e.g., 0.2%, 0.3%, 0.4%, 0.5%, 0.6%, 0.8%, 1%, 1.2%, etc. Any suitable fibrillar component can be used in the collagen compositions of the invention. Fibrillar collagen solids can be prepared using a variety of methods. For example, fibrillar collagen may be reconstituted collagen prepared from animal sources such as bovine hide (Frontiers in Matrix Biology, Vol. 10, pp. 1-58, in *Methods of Connective Tissue Research*, Eds. Robert, Moczar, and Moczar, S. Karger, Basel, 1985). Fibrillar collagen may be prepared from human or animal sources as described in U.S. Pat. Nos. 4,969,912 and 5,322,802. The fibrillar collagen solids are suspended in solution at a concentration typically ranging from about 10-100 mg/ml. The collagen suspension containing fibrillar collagen solids is combined with, e.g., added to, a soluble collagen composition either prior to or following addition of the therapeutic agent to a solution comprising soluble collagen.

In some embodiments of the invention the soluble collagen preparation comprises a chemical cross-linking agent. The agent may crosslink collagen molecules and/or fibrils to one another and/or may crosslink a therapeutic agent such as compstatin or an analog thereof to a collagen molecule or fibril. Typical cross-linking agents crosslink collagen amine groups to one another or to amine, carboxyl, phenol, sulfonyl, or carbohydrate groups of therapeutic agents. Suitable cross-linking agents include, but are not limited to, those described in WO 00/47130. Without wishing to be bound by any theory, cross-linking may stabilize the collagen gel (e.g., decrease its rate of breakdown) and/or decrease the rate of release of the therapeutic agent from the gel.

Without wishing to be bound by any theory, the presence of fibrillar collagen solids may have any of a variety of advantageous effects. By way of non-limiting example, the fibrillar collagen solids may increase the in vivo stability of the collagen gel, e.g., they may decrease the rate of breakdown of the gel. The fibrillar collagen solids may increase the stability of a therapeutic agent contained in the gel and/or decrease or modulate the rate at which the agent is released from the gel by diffusion and/or breakdown of the gel.

The collagen preparations preferably form a gel within 5 minutes (300 seconds) following contact with physiological fluids. More preferably the collagen preparations form a gel within 90 seconds, 2 minutes (120 seconds) or within 3 minutes (180 seconds) following contact with physiological fluids. Preparations that form a gel within shorter time periods, e.g., within 5-90 seconds, or longer time periods, e.g., 3-5 minutes, can also be used.

Any of collagen types I-XXVIII, or mixtures thereof, can be used in the present invention. The collagen can be purified from natural sources (e.g., human tissue or animal tissue such as bovine, rabbit, etc.) as described in the above-referenced patents and publications. Alternatively, the collagen can be manufactured using recombinant DNA techniques, in which case the sequence can be of human or animal origin. See, e.g., U.S. Pat. Nos. 5,593,854 and 5,667,839. Methods for the production of proteins, e.g., a polypeptide of interest such as a collagen chain, using recombinant DNA technology are well known in the art. Suitable methods include those described above. The term "collagen" includes collagen fragments. Thus in certain embodiments the soluble collagen comprises or consists of a collagen fragment or combination of fragments. In certain embodiments a complete collagen polypeptide chain is used.

While collagen preparations such as those described above are particularly preferred in certain embodiments of the invention, a variety of other gel-forming materials could also be used in a gel-forming composition of the invention. In certain embodiments the gel is a hydrogel, by which is meant a gel that contains a substantial amount of water. Preferably the material and the gel that it forms are biocompatible. In certain embodiments the material and the gel that it forms are biodegradable. A variety of modified or derivatized collagens are also of use in various embodiments of the invention. See, e.g., U.S. Pat. No. 5,201,764. For example, collagen can be acylated with one or more acylating agents such as glutaric anhydride, succinic anhydride, and maleic anhydride and at least one other acylating agent selected from the group consisting of methacrylic anhydride, beta-styrene sulfonyl chloride, ethylene-maleic anhydride copolymer, styrene-maleic anhydride copolymer or poly(vinyl) sulfonic acid.

Other gel-forming materials include, but are not limited to, hyaluronic acid and modified forms thereof, polysaccharides such as alginate and modified forms thereof, self-assembling peptides, etc. See, e.g., U.S. Pat. No. 6,129,761 for further description of alginate and modified forms thereof, hyaluronic acid and modified forms thereof, and additional examples of soluble gel-forming materials that are of use in various embodiments of the present invention. As described therein, other polymeric hydrogel precursors include polyethylene oxide-polypropylene glycol block copolymers such as Pluronics™ or Tetronics™ which are crosslinked by hydrogen bonding and/or by a temperature change, as described in Steinleitner et al., *Obstetrics & Gynecology*, 77:48-52 (1991); and Steinleitner et al., *Fertility and Sterility*, 57:305-308 (1992). Other materials which may be utilized include proteins such as fibrin or gelatin. Polymer mixtures also may be utilized. For example, a mixture of polyethylene oxide and polyacrylic acid which gels by hydrogen bonding upon mixing may be utilized.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., ASAID Trans., 38:154-157 (1992).

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin. In some embodiments a self-assembling peptide, such as those described in U.S. Pat. No. 6,800,481 is used. These peptides self-assemble to form a hydrogel structure upon contact with monovalent cations, e.g., such as those present in extracellular fluid.

In embodiments of the invention in which the gel is formed by cross-linking polymer chains to one another, the composition can include an appropriate cross-linking agent, which is selected according to the particular polymer. Alternately, the cross-linking agent can be administered after administration of the composition containing the gel-forming material, at substantially the same location. Any of these gels can be formed in vitro, e.g., as described above for gels comprising soluble collagen, and implanted at an appropriate location in or in the vicinity of the eye.

In certain embodiments of the invention the composition contains cells that produce and secrete compstatin or a complement inhibiting analog thereof instead of, or in addition to, containing the molecule itself. In these embodiments, the gel may be resistant to degradation, so that it traps the cells therein for a sustained period of time.

Figure 1B:
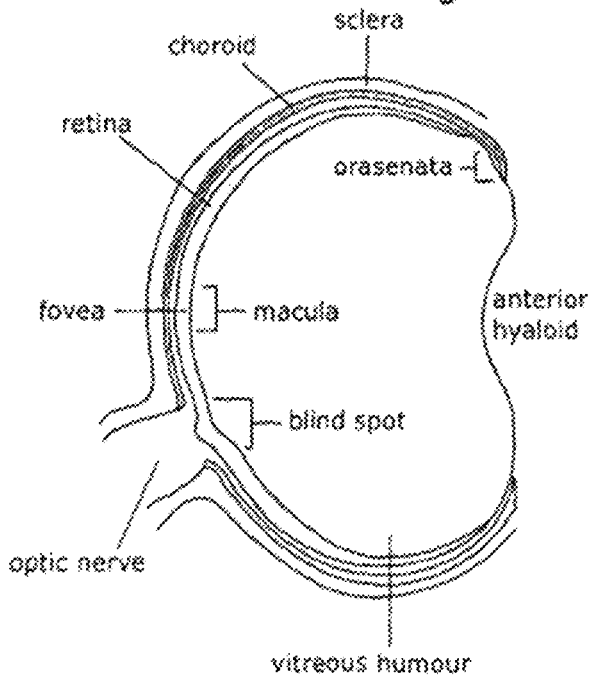
Figure 1C:
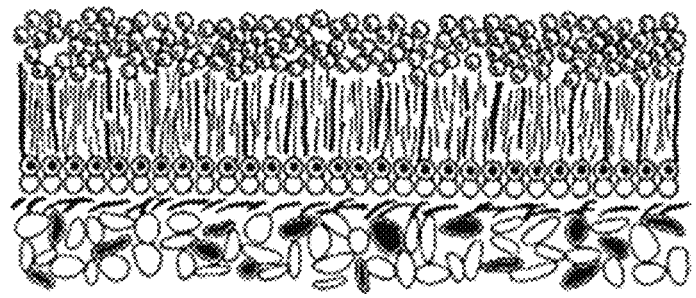
Figure 1D:
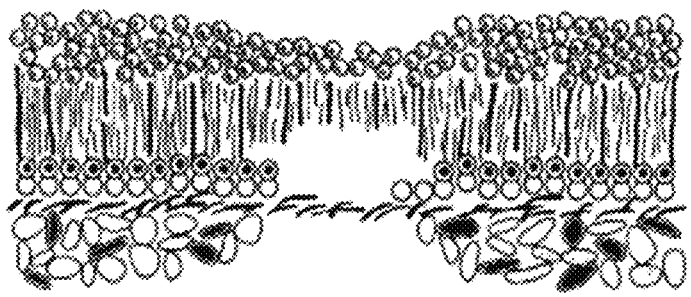
Figure 1E:
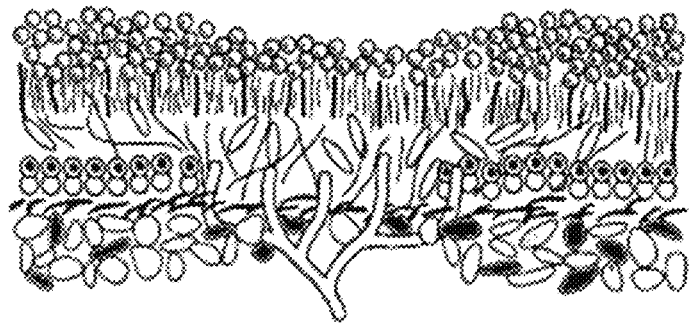

Methods of Administration, Dose, and Dosing Regimens for a Composition Comprising a Gel-Forming Material Any suitable method may be used to administer the gel-forming compositions of the invention to a location in or near the posterior segment of the eye. As shown in FIGS. 1A and 1B, the eye can be divided into an anterior segment and a posterior segment. The sclera, which is a thin, avascular layer of tissue, covers the outside of the eye around the posterior segment and part of the anterior segment and is continuous with the cornea, the transparent covering of the front of the eye. The choroid and retina underlie the sclera. The optic nerve transmits nerve impulses from the retina along the visual pathways.

The composition may be administered by a periocular approach, which term is used to refer to any route of administration that locally delivers a composition into the region outside the eye, i.e., exterior to the sclera. The composition is thus delivered to an area outside of and in close proximity to the posterior segment of the eye. In certain embodiments a composition administered in close proximity to the posterior segment of the eye is administered such that at least one edge or surface of the gel is within 10 mm of at least one point on the exterior surface of the portion of the sclera that covers the outside of the posterior segment of the eye. Preferably at least one edge or surface of the gel is within 5 mm of at least one point on the exterior surface of the portion of the sclera that covers the outside of the posterior segment of the eye. In certain embodiments at least one edge or surface of the gel is within 1-2 mm of at least one point on the exterior surface of the portion of the sclera that covers the outside of the posterior segment of the eye, or within 1 mm or less of at least one point on the exterior surface of the portion of the sclera that covers the outside of the posterior segment of the eye.

Periocular administration may be accomplished using, e.g., retrobulbar, peribulbar, sub-Tenon, or subconjunctival injection, by subretinal injection, by suprachoroidal injection, or by use of a catheter or cannula directed to any of the regions accessed by the afore-mentioned techniques. Most commonly a syringe is used, but a pump or any other source of pressure could also be used. In certain preferred embodiments of the invention the composition is administered adjacent to the sclera, outside the eye, e.g., by retrobulbar, sub-Tenon, or subconjunctival injection. At least one surface of the gel may be in direct contact with the sclera. Methods suitable for administration of local anesthesia for ophthalmic surgery are of use to deliver a composition of the invention. See, e.g., Dutton, J J, et al., "Anesthesia for intraocular surgery", *Surv Ophthalmol.* 46(2):172-84, 2001; Canavan, K. S., et al., "Sub-Tenon's administration of local anaesthetic: a review of the technique", *British Journal of Anaesthesia,* 90(6), 787-793, 2003. See also, Spaeth, supra, and Albert and Lucarelli, supra. Compositions delivered according to these standard techniques are considered to be delivered in close proximity to the posterior segment of the eye. The composition forms a gel which, in certain embodiments of the invention at least partially overlies the macula. In certain embodiments of the invention the composition is administered into the sclera itself, e.g., by injection or using a catheter or cannula (see, e.g., U.S. Pat. No. 6,378,526). The therapeutic agent is released from the composition and diffuses from its site of release across the sclera and into the eye, where it reaches a site of activity at the retina. Alternately, a gel structure formed in vitro can be implanted in or in the vicinity of the eye.

The amount and concentration of the therapeutic agent(s) in a composition comprising soluble collagen can vary depending on a number of factors including, but not limited to, the identity of the therapeutic agent(s), the condition being treated and its severity, the presence or absence of fibrillar collagen and/or chemical cross-linking agents in the composition, the total amount of composition administered (which itself can vary based on various considerations such as the anatomy of the patient, etc.) It may be desirable to employ a concentration and/or total amount of therapeutic agent(s) that will maximize the total amount of agent delivered to the eye, while keeping the concentration actually released from the gel below that which could cause unacceptable side effects. In certain embodiments of the invention the total amount and concentration of the agent(s) are selected to provide an effective concentration of the agent at the retina over a period of at least 4 weeks, e.g., 4-6 weeks, 6 weeks or greater, 8 weeks or greater, etc.

The dosing interval (i.e., the time between individual administrations of an inventive composition) and the dose of the therapeutic agent delivered with each administration can vary. In certain embodiments the composition is delivered at times more than 6 weeks apart, e.g., 2, 3, 4, 5, or 6 months apart, or any intervening number of weeks, e.g., 8, 10, 12, 14, 16 weeks, etc. In other embodiments the composition is delivered at even greater time intervals, e.g., at times 7, 8, 9, 10, 11, or 12 months apart. In other embodiments the time interval is 6 weeks or less. Of course the time interval can vary. For example, the time intervals between doses can alternate between 6 weeks or less and more than 6 weeks. In certain embodiments the average time interval between administrations of an inventive composition is at least 6 weeks, e.g., 2, 3, 4, 5, or 6 months, or any intervening number of weeks, e.g., 8, 10, 12, 14, 16 weeks, etc. In certain embodiments of the invention the composition is administered multiple times at time intervals on average at least 6 weeks apart, at least 8 weeks apart, at least 10 weeks apart, at least 12 weeks apart, etc. Typically the composition is administered at least 2, 5, 10, 20, 50, or more times. The composition can and often will be administered indefinitely to a subject suffering from or at risk of a macular degeneration related condition, CNV, RNV, ocular inflammation, etc.

The total amount of therapeutic agent and its concentration in the gel can also vary. Exemplary, nonlimiting, doses are between approximately 0.1 and 100 mg/dose for each eye to be treated, e.g., between approximately 0.5 and 50 mg/dose, between 1 and 10 mg/dose, etc. Exemplary, nonlimiting concentrations of a therapeutic agent in a composition of the invention are between approximately 0.1 and 100 mg of the therapeutic agent per milliliter of collagen solution, e.g., the concentration may be between 1 and 50 mg/ml, between 1 and 10 mg/ml, etc.

In some embodiments a dose of a first therapeutic agent such as compstatin or a complement inhibiting analog thereof is administered intravitreally, and a composition of the invention comprising a second therapeutic agent, which can be the same as or different to the first therapeutic agent, is administered to the subject using a periocular administration technique, with the two administrations occurring within a reasonably narrow period of time, e.g., within up to about 6 weeks of one another. The intravitreal administration may provide an initial high concentration of the therapeutic agent at the retina. The periocular administration then provides a sustained release of the therapeutic agent over time.

Testing Therapeutic Potential in Animal Models and Humans

A number of different animal models that attempt to replicate one or more features of macular degeneration, diabetic retinopathy, choroidal neovascularization, and/or ocular inflammation are known in the art. A composition containing compstatin or a complement inhibiting analog thereof can be administered in various doses to mice, rats, dogs, primates, etc. that have spontaneous macular degeneration and/or choroidal neovascularization or in which macular degeneration and/or choroidal neovascularization have been induced by a treatment. The ability of the compound to prevent or treat one or more signs or symptoms of macular degeneration (e.g. CNV, accumulation of lipofuscin in and/or drusen beneath the RPE, photoreceptor atrophy or hypertrophy, altered RPE pigmentation, photoreceptor loss, altered electroretinogram, etc.) is assessed. Visual examination, photography, histopathology, immunohistology, etc., can be used.

Useful models include animals (e.g., non-human primates, etc.) in which choroidal neovascularization is induced by laser treatment (Bora, P. S., et al., *Proc. Natl. Acad. Sci.* 100(5): 2679-2684, 2003; Zacks, D N, et al., *Invest Ophthalmol Vis Sci.* 243(7):2384-91, 2002). Other models include animals that have been treated with a variety of agents such as lipid hydroperoxide (Tamai, K., et al., *Exp Eye Res.* 74(2): 301-8, 2002), pellets comprising growth factors, etc. Animals genetically engineered to overexpress or underexpress one or more genes are also useful. It will be appreciated that since the affinity of compstatin for non-primate C3 is reported to be lower than that for human or non-human primate C3, doses that would inhibit primate C3 may be insufficient to inhibit non-primate C3. However, larger doses, relative to the amount of C3, may be used.

The candidate agent can be administered systemically or locally. The agent can be delivered orally, intravenously, intraperitoneally, intravitreally, transsclerally or topically. The agent can be delivered by intravitreal injection, transclerally, by sustained release implant, etc. The eye can be analyzed by ophthalmoscopy, angiography, histopathology or a combination thereof. Any of these methods can be used to assess efficacy of a candidate agent in any animal model. Models also exist for diabetic retinopathy. Animal models for ocular inflammation are also known in the art. For example, experimental allergic uveitis is a well-known model system (Singh, V K., et al., *Indian J Med. Res.*, 107:53-67, 1998). Endotoxin-induced uveitis is another useful model (Kozhich, A. T., et al., *Investigative Ophthalmology and Visual Science*, 41:1823-1826, 2000.) These examples are but a few of the model systems in which efficacy of the compounds of the invention can be assessed.

Compounds that show promising results in animal studies including, but not limited to, acceptable safety and feasibility of administering a dose expected to effectively inhibit complement in the human vitreous, are tested in humans, e.g., using standard protocols and endpoints for clinical trials for therapies for ARMD or diabetic retinopathy. It will be appreciated that in the case of many of the ocular conditions of interest herein, demonstrating efficacy in animal models is not necessary in order to establish that a compound described herein is considered therapeutically useful by those of skill in the art and/or for conducting clinical trials in humans.

In addition to protocols and endpoints that have typically been employed in evaluating therapies for wet ARMD in humans, the present invention contemplates testing the inventive compositions to establish their utility in inhibiting progression from the dry form of ARMD to the wet form, in inhibiting development of dry ARMD in a subject at risk thereof, or in inhibiting progression from a mild to a more severe form of dry ARMD. Accordingly, in some embodiments the compositions are administered to subjects who have been diagnosed with the dry type of ARMD or determined to be at risk of developing ARMD. The ability of the composition to inhibit progression of the dry form of ARMD to wet type ARMD or to inhibit development of dry ARMD is assessed. In certain embodiments of the invention subjects who are at increased risk of developing ARMD as compared with the general population of the same age, are selected for therapy. In certain embodiments of the invention subjects suffering from dry ARMD who are at high risk of progressing to wet ARMD, e.g., patients already suffering from wet ARMD in one eye, patients with a genetic disposition toward severe ARMD, or with any other indicators, are selected for therapy. Polymorphisms that increase risk of developing ARMD are mentioned above and described in more detail in the literature. In one embodiment the subject is tested to determine whether the subject has a polymorphism in the CFH, CFB, TLR4, or LOC387715 locus. Subjects determined to be at increased risk as a result of being homozygous or heterozygous one or more genetic polymorphisms known to be associated with ARMD are selected for therapy. In one embodiment, the subject is heterozygous or homozygous for 1, 2, 3, or more polymorphisms known to be associated with increased risk of ARMD, e.g., increased risk of developing ARMD, increased risk of progressing from dry to wet ARMD, increased risk of developing a severe form of ARMD, etc.

Subjects may be classified as having early, intermediate, or advanced ARMD in accordance with the classification scheme used in the Age-Related Eye Diseases Study (AREDS), which is set forth in guidelines developed American Academy of Ophthalmology (American Academy of Ophthalmology, Age Related Macular Degeneration Preferred Practice Pattern™, 2003; available for download at URL www. followed immediately by aao.org/aao/education/library/ppp/amd_new.cfm).

In one example, subjects with the dry type of ARMD are divided into two groups. One group receives a single intravitreal injection of the inventive composition, or a retrobulbar or sub-Tenon injection of the inventive composition in the vicinity one eye, e.g., in close proximity to the posterior segment of the eye, while the other group either receives either no treatment or a single intravitreal injection of another therapeutic agent such as Macugen or Lucentis into one eye. The groups are monitored over a period of 6 months to 2 years to determine the percentage of subjects that progress to the wet type of ARMD.

In another example, subjects with the dry type of ARMD are divided into two groups. One group receives a single intravitreal injection of the inventive composition, or a retrobulbar or sub-Tenon injection of the inventive composition in the vicinity of one eye, e.g., in close proximity to the posterior segment of the eye, every 6 months while the other group either receives either no treatment or a single intravitreal injection of another therapeutic agent such as Macugen or Lucentis into one eye every 6 months. The groups are monitored over a period of 1-2 years (or longer) to determine the percentage of subjects that progress to the wet type of ARMD. In another non-limiting example, subjects with dry type ARMD are divided into two groups. One group receives an intravitreal injection of the inventive composition, or a retrobulbar or sub-Tenon injection of the inventive composition in the vicinity of one eye, e.g., in close proximity to the posterior segment of the eye, every 3-6 months while the other group receives either no treatment or receives treatment with Macugen or Lucentis according to the standard protocols used for treating wet type ARMD, i.e., intravitreal injection every 4-6 weeks. The groups are monitored for a period of 1-2 years (or longer) to determine the percentage of subjects that progress to the wet form of ARMD.

In another example, subjects with wet ARMD in at least one eye are divided into two groups. One group is administered an intravitreal injection of Lucentis or Macugen to the study eye, followed by an intravitreal injection of an inventive composition shortly thereafter (e.g., within 2 weeks). The other group is given an intravitreal injection of Lucentis or Macugen into the study eye according to standard protocols. The groups are monitored over time (e.g., 6 months to 2 years) to evaluate progression, recurrence of symptoms, need for retreatment, etc.

In another example the ability of an inventive composition to inhibit progression of early ARMD (AREDS 2) to intermediate ARMD (AREDS 3) is assessed. Subjects with early ARMD are divided into two groups, one of which receives an inventive composition as described in any of the examples above while the other receives either no therapy or an alternative therapy such as Lucentis or Macugen as described above. The groups are monitored for a period of time (e.g., as described above) to determine the percentage of subjects that progress from early to intermediate ARMD.

In another example the ability of an inventive composition to inhibit progression of intermediate ARMD (AREDS 3) to advanced ARMD (AREDS 4) is assessed. Subjects with intermediate ARMD are divided into two groups, one of which receives an inventive composition as described in any of the examples above while the other receives either no therapy or an alternative therapy such as Lucentis or Macugen as described above. The groups are monitored for a period of time (e.g., as described above) to determine the percentage of subjects that progress from intermediate to advanced ARMD.

In addition to monitoring progression of ARMD, the incidence of side effects and complications may also be monitored. Consideration of side effects is an important aspect when evaluating the overall outcome and risk/benefit ratio of a therapy. For example, if two therapies are equally efficacious in terms of inhibiting progression of or treating ARMD, the therapy with a lower incidence of side effects is typically preferred for most subjects. In certain embodiments of the invention therapy of a macular degeneration related condition such as ARMD, or CNV or RNV from any cause, using a composition of the invention is associated with fewer side effects over time (e.g., over a 1-2 year period) than a FDA-approved therapy for ARMD.

Identifying Subjects and Assessing Response

The methods of the invention may include providing a subject to which a composition of the invention is to be administered. The subject is typically at risk of or suffering from an eye disorder characterized by macular degeneration, choroidal neovascularization, retinal neovascularization, or any combination of these. The composition is typically administered to the subject with the intent of treating or preventing development of such condition. Thus the subject will typically have been identified as being at risk of or suffering from such a condition. Methods for diagnosis of macular degeneration and choroidal neovascularization and for assessing response to therapy are known in the art. Any suitable tests and criteria can be used to identify a subject at risk of or suffering from a macular degeneration related condition, diabetic retinopathy, or choroidal neovascularization and/or to measure a response to therapy. Visual acuity can be measured using, for example, a Snellen chart, a Bailey-Lovie chart, a decimal progression chart, a Freiburg visual acuity test, a measurement of minimum angle of resolution (MAR) etc. Metamorphopsia (visual distortion) may be measured using an Amsler chart. Contrast sensitivity may be measured using a Pelli-Robson chart. Diagnostic studies include, but are not limited to, standard ophthalmologic examination of the fundus, stereo biomicroscopic examination of the macula, intravenous fundus fluorescein angiography, fundus photography, indocyanine green video-angiography, and optical coherence tomography. A subject displaying an abnormality on one or more of these diagnostic studies (e.g., a subject that falls outside a range that is considered normal for a healthy eye) may be treated in accordance with the present invention. As noted above, subjects may be classified as having early, intermediate, or advanced ARMD in accordance with the classification scheme used in the Age-Related Eye Diseases Study. A subject falling into any of the categories described therein, may be treated in accordance with the present invention. If the subject has already developed CNV, the subject may have classic CNV, occult CNV, or a mixture of the two. Of course alternate classification schemes, of which a variety is described in the literature, could also be used.

ARMD is known to have a genetic component, based on studies showing an increased incidence of ARMD in individuals with relatives suffering from ARMD (e.g., twin studies) and on a number of recent studies showing that polymorphisms in a number of complement factors are associated with increased risk of ARMD. Therefore, a subject may be considered at risk of developing ARMD if he or she has one or more close relatives (e.g., parent, grandparent, sibling, cousin, uncle, aunt), who has received a diagnosis of ARMD. Individuals who smoke and/or consume a high fat diet are also at increased risk. The incidence of ARMD increases with age. Therefore, an individual over approximately 50 years of age, generally at least 60 or at least 70 years of age may be considered at increased risk. An individual having drusen and one or more additional risk factors may be at particular risk for developing ARMD. An individual with multiple drusen, particularly if large and with indistinct borders, may be at particular risk. An individual with RPE hyperpigmentation or hypopigmentation or geographic atrophy may be at particular risk. In certain embodiments of the invention the subject has one or more genetic polymorphisms associated with increased likelihood of developing ARMD, some of which are noted above. In certain embodiments of the invention the method of treatment comprises determining whether the subject has a genetic polymorphism that increases the risk of ARMD. "Determining" as used here refers to establishing that a subject has a polymorphism that increases the risk of ARMD, either by performing or ordering a suitable test, or by receiving results of a test performed or ordered by another, wherein the test ascertains whether the subject has the polymorphism. It will be appreciated that a useful genetic test need not be 100% accurate. Specific genetic mutations are associated with various less common macular degeneration related conditions. A subject who has received a diagnosis of diabetes is at risk of developing diabetic retinopathy.

Response to therapy can be assessed by any of the methods mentioned above. Numerous studies have been conducted to assess the efficacy of a variety of different therapies in restoring vision, preventing visual loss, and/or resulting in improvement or slowing progression of ARMD or choroidal neovascularization as judged by diagnostic tests such as those described above. One of ordinary skill in the art will be able to select appropriate criteria by which to judge the efficacy of therapy.

Therapeutic Applications

The compositions of the invention can be administered to a subject (e.g., a human patient) to treat a macular degeneration related condition (e.g., ARMD), diabetic retinopathy, retinopathy of prematurity, persistent hyperplastic vitreous syndrome, choroidal neovascularization, etc. The subject may have exudative or nonexudative ARMD. In certain embodiments of the invention that subject has exudative ARMD but does not have RAP while in other embodiments the subject does have RAP. In certain embodiments, protocols that show promising results in clinical trials are employed.

One particularly advantageous use for the compositions and methods of the invention is to inhibit progression of non-exudative ARMD to exudative ARMD or to inhibit progression of non-exudative ARMD to a more severe form. In certain embodiments of the invention an inventive composition inhibits progression of early ARMD (AREDS 2) to intermediate ARMD (AREDS 3) or to advanced ARMD (AREDS 4). In certain embodiments of the invention the composition inhibits progression of intermediate ARMD (AREDS 3) to advanced ARMD (AREDS 4). Any of the compositions of the invention may be used for one or more of these purposes in various embodiments of the invention. Reference to various stages of ARMD as described in the AREDS is in no way intended to be limiting. It will be recognized that other classification schemes could be used.

In a specific embodiment a composition of the invention, e.g., a gel-forming composition of the invention, is used for treating subjects with non-exudative ARMD, e.g., to prevent or inhibit progression to exudative ARMD. In certain embodiments the subject has not developed detectable CNV and the composition prevents or delays the development of CNV. For example, the subject may have dry ARMD, and the composition prevents or delays the onset of wet ARMD. In certain embodiments the subject has developed detectable CNV and the composition slows the rate of progression of CNV and/or causes regression of existing CNV. In certain embodiments the subject has not developed detectable RNV and the composition prevents or delays the development of RNV. In certain embodiments the subject has developed detectable RNV and the composition slows the rate of progression of RNV and/or causes regression of existing RNV. The composition can be administered once or multiple times to a subject who does or does not have a condition such as CNV or RNV (or both), e.g., at approximately predetermined time intervals such as, for example, approximately every 4 weeks, approximately every 6 weeks, approximately every 8, 10, 12, 16, 20, 24 weeks, approximately every 6, 8, 10, or 12 months, etc. It will be understood that in any of the methods of this invention, the composition should be administered in an amount effective to achieve the indicated result, within sound medical judgment. It should also be understood that the result need not be achieved in every instance.

Ancillary therapies may also be used concurrently, prior to, or following treatment using the compositions and methods of the invention. Such therapies include, but are not limited to, administration of antioxidant vitamin and/or mineral therapy, photodynamic therapy (e.g., with verteporfin or other agents), administration of antiinflammatory agents, antiangiogenic therapy (e.g., administration of one or more angiogenesis inhibitors such as anecortave acetate or other angiostatic steroids; anti-VEGF or anti-VEGFR antibody, antibody fragment, siRNA, antisense RNA, or aptamer; or any other antiangiogenic agent including but not limited to a small molecule, siRNA, antisense RNA, or aptamer targeted to any proangiogenic gene), growth factor administration, implantation of cells (e.g., neural stem cells, RPE stems cells, RPE cells) into the eye, laser photocoagulation, radiation therapy, thermal therapy, and surgery (e.g., submacular surgery or macular translocation). In certain embodiments of the invention a growth factor for RPE cells is administered, e.g., REF-1/TFPI-2 (Tanaka, Y, et al., *Invest Ophthalmol Vis Sci.* 45(1): 245-52, 2004).

It may be desirable to treat an eye that already suffers from choroidal and/or retinal neovascularization (e.g., in a subject with diabetic retinopathy or ARMD) using photocoagulation or surgery and to also administer a composition of the invention to the subject to preserve vision in the other eye and/or prevent a recurrence of CNV and/or RNV in the eye treated with photocoagulation or surgery.

EXAMPLES

Example 1

Prevention of Choroidal Neovascularization in a Mouse Model by Administration of a Compstatin Analog Materials and Methods
Complement Inhibitors Recombinant VCP was produced in and purified from a *Pichia pastoris* expression system as described in (Sahu, A, et al., *J. Immunol.*, 160, 5596-5604, 1998). VCP was dissolved in physiological saline at various concentrations.

Figure 2:
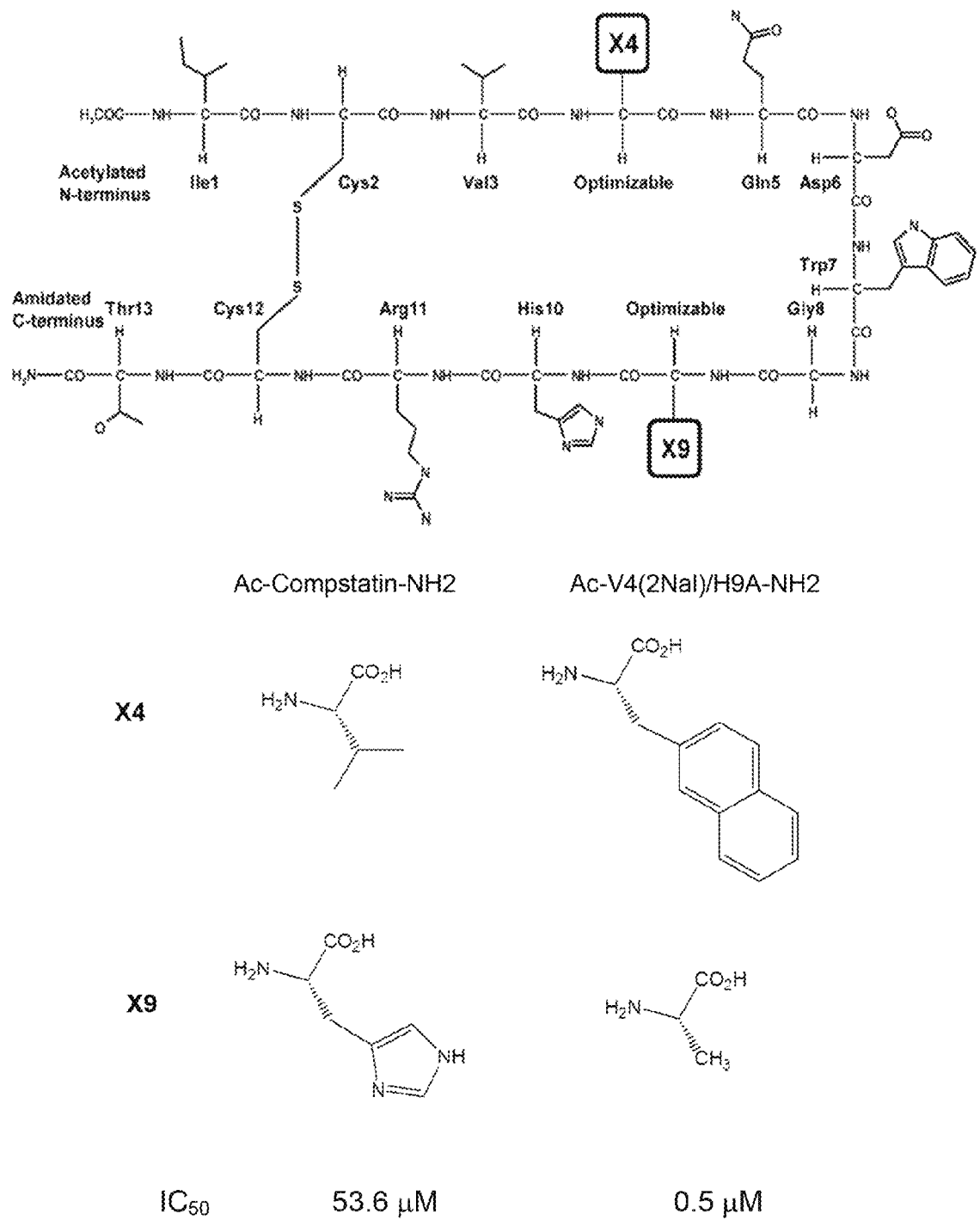
FIG. 2 shows a schematic diagram of compstatin and of a compstatin analog (SEQ ID NO: 14) that has increased complement inhibiting activity relative to compstatin. The figure also shows the IC50 of compstatin and the compstatin analog for inhibition of human complement. Amino acids 4 and 9 in the peptide chain depicted in the upper portion of the figure are as shown on the lower left for compstatin and as shown on the lower right for the compstatin analog. Thus the boxes labeled "X4" and "X9" in the peptide chain represent the side chains of the amino acids X4 and X9 shown in the lower portion of the figure for compstatin (left) and the compstatin analog (right) respectively.
Figure 3:
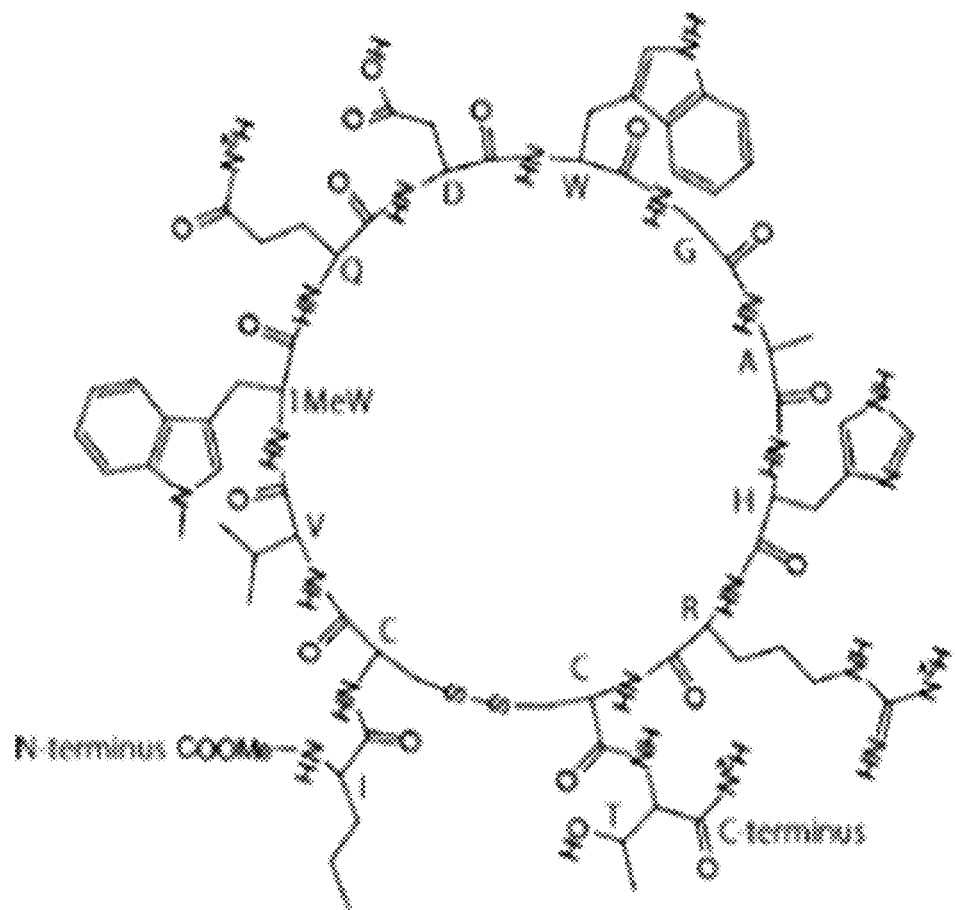
FIG. 3 shows a schematic diagram of a compstatin analog (compstatin C; SEQ ID NO: 28) with a higher inhibitory complement inhibiting activity than compstatin. (Katragadda, et al., 49(15) pp 4616-4622, 2006).

The compstatin analog shown in FIG. 2, in which positions 4 and 9 were altered relative to the compstatin peptide, was chemically synthesized and dissolved in physiological saline.

CNV Induction in Mice

C57BL/6 mice (The Jackson Laboratory) were anesthetized with a mixture of ketamine/xylazine (8:1) and the pupils were dilated with a single drop of 1% tropicamide. Krypton red laser photocoagulation (50-µm spot size, 0.05 s duration, 250 mW) will be used to generate laser spots in surrounding the optic nerve by using a hand-held coverslip as a contact lens. Formation of a bubble at the laser spot indicated rupture of Bruch's membrane. Multiple laser spots were generated in each eye.

Injection of VCP or Compstatin into the Eyes of Mice

Mice in which CNV has been previously laser-induced were administered solutions containing VCP or the compstatin analog by intravitreal injection. Different groups of mice were injected with different quantities of this molecule or of mouse albumin (as a control) to determine the effect of dosage on the efficacy and toxicity of VCP. Briefly, after anesthesia and dilation of the pupil, the anterior chamber was entered via the limbus with a 28-gauge needle to decompress the eye. Under an operating microscope, which allows visualization of the retina, a 32-gauge (blunt) needle was passed through a scleral incision, just behind the limbus, into the vitreous cavity. A Hamilton syringe was used to inject between 1 and 3 µl of a solution containing either VCP, the compstatin analog, or albumin.

Determination of Incidence and Size CNV

Seven days after CNV induction incidence of CNV was determined. Briefly, the mice were perfused with a FITC-dextran (Sigma-Aldrich) solution just prior to sacrifice. After the eyes were excised and fixed for 1 h in 10% phosphate-buffered formalin, RPE-choroid-scleral flat mounts were prepared as follows. The cornea and the lens were removed and the neurosensory retina carefully dissected from the eyecup. Five radial cuts were from the edge of the eyecup to the equator; the sclera-choroidretinal pigment epithelium (RPE) complex was flat-mounted, with the sclera facing down, on a glass slide in Aquamount. The flat mounts were stained with an anti-elastin specific monoclonal antibody (Sigma-Aldrich) and then with a CY3-conjugated secondary antibody (Sigma-Aldrich) at a suitable concentration, e.g., at a 1/200 dilution of a 1.0 mg/ml stock solution. Mounts were observed under confocal microscopy (LSM510, Zeiss). The prominent neovascular growth stained green whereas the underlying elastin in the Bruch's membrane stained red within a laser spot. Images were analyzed with the image analysis software AxioVision (Zeiss). The amount of CNV was determined by measuring the total green-fluorescent surface area in each picture. A mean green-fluorescent area was obtained for the various groups and compared using student t-test for comparisons between groups and ANOVA for comparison among multiple groups. The number of spots studied was as follows: No treatment control: 35 spots); mouse albumin control: 12 spots; VCP (10 µg): 26 spots; VCP (30 µg): 14 spots; compstatin analog (30 µg): 27 spots. Deposition of a variety of different complement components is also measured using immunological techniques and/or RT-PCR.

Results

Figure 4:
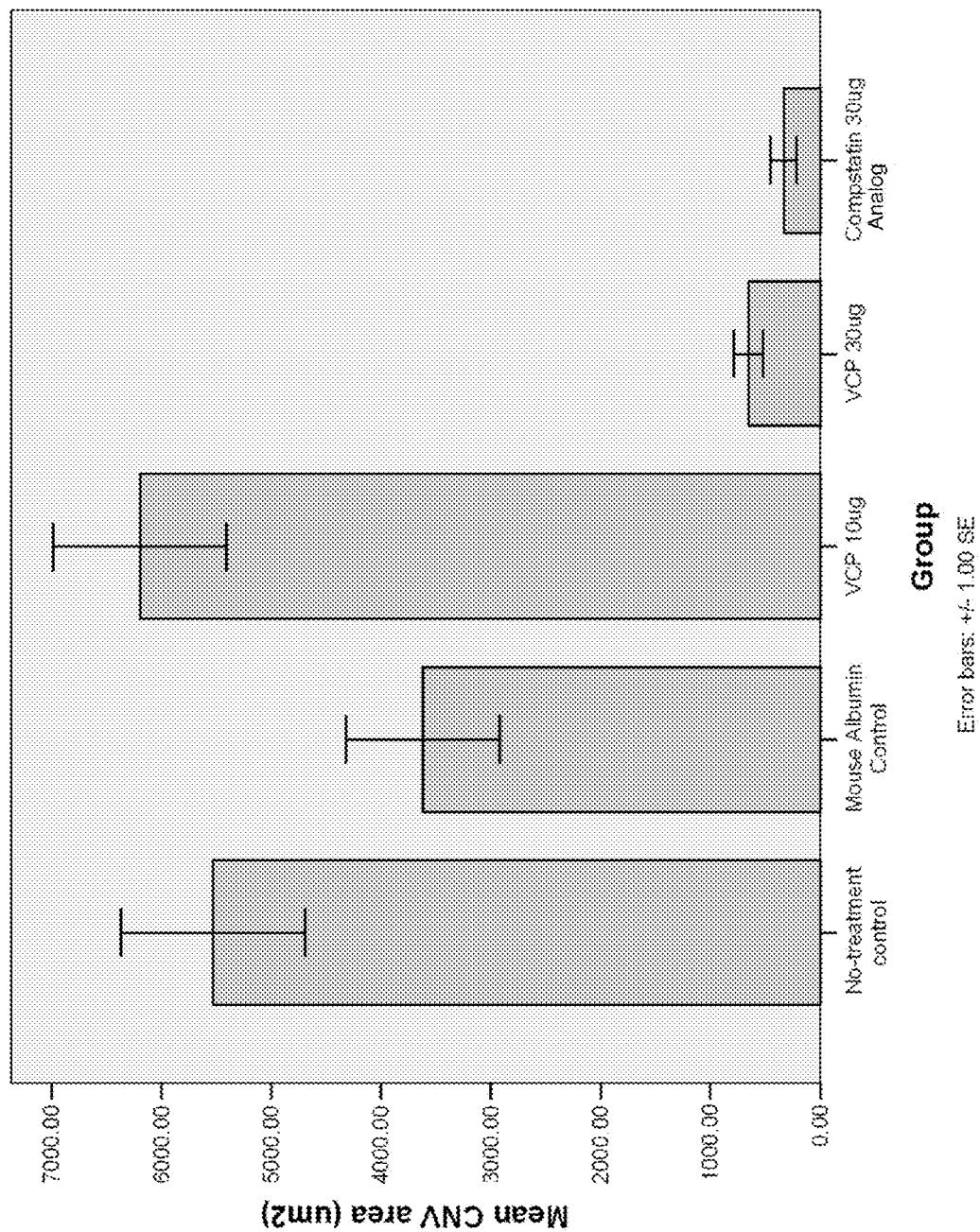
FIG. 4 is a graph showing a comparison of the mean CNV area (in $\mu m^2$) in mice that received either no treatment or received an intravitreal injection of albumin, an intravitreal injection of vaccinia complement control protein (VCP) (either 10 or 30 µg), or an intravitreal injection of a compstatin analog (30 µg).

The effects of VCP or the compstatin analog on the development of CNV was tested in a murine model of laser-induced CNV. Briefly, VCP (either 10 µg/eye or 30 µg/eye) or compstatin (30 µg/eye) was injected into the vitreous 24 hrs after laser induction. Seven days after CNV induction, incidence of CNV was determined. Just prior to sacrifice, the mice were perfused with a FITC-dextran (Sigma-Aldrich) solution. After the eyes were excised and fixed in 10% phosphate-buffered formalin, RPE-choroid-scleral flat mounts were prepared and stained with an anti-elastin specific monoclonal antibody (Sigma-Aldrich) and then with a CY3-conjugated secondary antibody (Sigma-Aldrich). Mounts were observed under confocal microscopy (LSM510, Zeiss). The prominent neovascular growth stained green whereas the underlying elastin in the Bruch's membrane stained red within a laser spot. Similar results were obtained with VCP and with the compstatin analog. Images were analyzed with the image analysis software AxioVision (Zeiss). The amount of CNV was determined by measuring the total green-fluorescent surface area in each picture. A mean green-fluorescent area was obtained for the various groups and compared using student t-test for comparisons between groups and ANOVA for comparison among multiple groups. Results are described in Table 2 and in the graph in FIG. 4. In Table 2, "compstatin" refers to the compstatin analog shown in FIG. 2. As is evident both from the table and the graph, administration of 30 µg of VCP or the compstatin analog caused a statistically significant reduction in the mean area of CNV relative to either no treatment or administration of albumin. The compstatin analog appeared to be somewhat more effective than VCP on a µg basis, although the difference was not statistically significant at these sample sizes.

TABLE 2

Effect of VCP or a Compstatin Analog on Development of CNV in a Mouse Model
Multiple Comparisons Dependent Variable: FldAreaGreen
Tamhane

| (I) Group | (J) Group | Mean Difference (I-J) | Std. Error | Sig. | 95% Confidence Interval Lower Bound | Upper Bound |
|---|---|---|---|---|---|---|
| No-treatment control | No-treatment control | | | | | |
| | Mouse Albumin Control | 1909.00993 | 1090.44317 | .601 | −1325.1110 | 5143.1309 |
| | VCP 10 ug | −666.84488 | 1151.10903 | 1.000 | −4015.6447 | 2681.9549 |
| | VCP 30 ug | 4877.53314* | 848.72770 | .000 | 2345.4558 | 7409.6105 |
| | Compstatin 30 ug | 5194.92113* | 846.05120 | .000 | 2668.9363 | 7720.9060 |
| Mouse Albumin Control | No-treatment control | −1909.00993 | 1090.44317 | .601 | −5143.1309 | 1325.1110 |
| | Mouse Albumin Control | | | | | |
| | VCP 10 ug | −2575.85481 | 1053.13838 | .182 | −5733.0303 | 581.3207 |
| | VCP 30 ug | 2968.52321* | 710.20220 | .013 | 533.9807 | 5403.0657 |
| | Compstatin 30 ug | 3285.91120* | 707.00147 | .006 | 853.1175 | 5718.7049 |
| VCP 10 ug | No-treatment control | 666.84488 | 1151.10903 | 1.000 | −2681.9549 | 4015.6447 |
| | Mouse Albumin Control | 2575.85481 | 1053.13838 | .182 | −581.3207 | 5733.0303 |
| | VCP 10 ug | | | | | |
| | VCP 30 ug | 5544.37802* | 800.23300 | .000 | 3101.1268 | 7987.6293 |
| | Compstatin 30 ug | 5861.76601* | 797.39374 | .000 | 3424.3034 | 8299.2287 |
| VCP 30 ug | No-treatment control | −4877.53314* | 848.72770 | .000 | −7409.6105 | −2345.4558 |
| | Mouse Albumin Control | −2968.52321* | 710.20220 | .013 | −5403.0657 | −533.9807 |
| | VCP 10 ug | −5544.37802* | 800.23300 | .000 | −7987.6293 | −3101.1268 |
| | VCP 30 ug | | | | | |
| | Compstatin 30 ug | 317.38799 | 176.41849 | .574 | −214.1787 | 848.9547 |
| Compstatin 30 ug | No-treatment control | −5194.92113* | 846.05120 | .000 | −7720.9060 | −2668.9363 |
| | Mouse Albumin Control | −3285.91120* | 707.00147 | .006 | −5718.7049 | −853.1175 |
| | VCP 10 ug | −5861.76601* | 797.39374 | .000 | −8299.2287 | −3424.3034 |
| | VCP 30 ug | −317.38799 | 176.41849 | .574 | −848.9547 | 214.1787 |
| | Compstatin 30 ug | | | | | |

*The mean difference is significant at the .05 level.

Example 2

Prevention of Choroidal Neovascularization in a Mouse Model by Administration of a Compstatin Analog Example 1 is repeated using a different compstatin analog. Doses ranging from 0.1-50 µg/eye are tested.

Example 3

Preparation of Collagen Solutions for a Gel-Forming Composition

Stock Collagen Preparation.

Collagen for all formulations will be prepared from porcine corium. Split porcine hide will be procured from Lampire Biological Laboratories (Pipersville, Pa.). Split hide will be rinsed with reagent alcohol and placed in frozen storage prior to receipt. Sections of split corium will be cut into small pieces (about 1 cm²), soaked in reagent alcohol, and then washed extensively with sterile water. The washed pieces will be placed in 20 volumes of 0.5M HCl for 30 minutes, washed with sterile water and then placed in 20 volumes of 0.5N NaOH for 30 minutes. Both treatments have been shown to be effective in reducing viral titers by up to 6 logs. In addition, both treatments have been shown to have significant bactericidal effects, reducing bacterial loads by up to 9 logs. The chemically disinfected corium will be washed extensively in sterile water, weighed and placed in 20 volumes (v/w) of 0.5M acetic acid. The pieces will be stirred for 72 hours and porcine mucosal pepsin added to the partially swollen corium.

Pepsin will be added at 2% (w/w wet corium) and stirred for 48 hours. An additional aliquot of pepsin will be added at 1% (w/w wet corium) and stirred for another 24 hours. At this point, the corium should be "dissolved" in acetic acid. Small, undissolved pieces will be removed by filtering the thick slurry through cheesecloth. The filtrate will be diluted with 0.5M acetic acid and dialyzed against 0.5N acetic acid using dialysis tubing having a 50,000 dalton nominal cut-off. An alternate dialysis method will utilize ultrafiltration/diafiltration cartridges procured from Amersham Biotech. The dialysis process removes pepsin and degraded pepsin. The retained liquid containing collagen will be subjected to differential NaCl precipitation to isolate predominantly Type I collagen. Purified Type I collagen at about 5 mg/mL will be then dialyzed against 0.1N acetic acid to remove residual salts (about 5,000 nominal molecular weight cut-off). The retained collagen solution will subsequently be filtered through 0.45 µm and 0.2 µm filters and placed in sterile, 2-liter glass bottles. Collagen concentration will be approximately 5 mg/mL. All steps will be conducted at room temperature. Stock solutions will be stored at 2-8° C.

Process Controls and Quality Control Tests: Final Stock Collagen Will be Examined by the Following Methods.

Analysis by SDS-PAGE to determine collagen purity;
Analysis of uronic acid to determine amounts of residual glycosaminoglycan
Assay of hydroxyproline to determine total collagen concentration;
Differential Scanning calorimetry to measure temperature of phase transition (pure, undenatured telopeptide-poor collagen has a transition onset of about 39° C.)
Sterility using USP methods
Endotoxin using LAL methods
Preparation of In Situ Gelling Collagen Solutions
Purified, pepsin-digested collagen will be precipitated by addition of solid NaCl to 0.8M. The resultant precipitate will be recovered by centrifugation at 3500 RPM, a wet weight determined, and the precipitate placed in dialysis tubing having a NMW cut-off of 50,000 Daltons. Attempts will be made to add enough precipitate to produce final collagen solutions at 30 and 50 mg/mL (3 and 5%). The tubing will be placed in 20 volumes of 0.035 M EDTA in deionized water, pH 5.0 and dialyzed with agitation for 24 hours. At this point, the dialysis tubing will be transferred to another 20 volumes of 0.035 M EDTA, pH 5.5. Dialysis will be conducted again for 24 hours after which the tubing will be placed in 0.035M EDTA, pH 6.0. This sequence will be continued until dialysis in a final EDTA solution at pH 7.5. This slow increase in pH during EDTA dialysis results in a collagen preparation that remains "soluble" at neutral pH. This is in contrast to standard collagen solutions that spontaneously undergo fibrillogenesis at neutral pH and room temperature. The neutral pH, EDTA-treated collagen solution will remain in solution during storage and will rapidly undergo gelation and fibril formation when exposed to physiological fluids.

Example 4

Use of ELISA-based Assay for Classical Complement Pathway Activation to Assess Complement Inhibiting Activity of Compstatin Analogs Materials:
Ninety six-well ELISA plate (Corning 3590)
Chicken OVA (Sigma A5378)
Polyclonal anti-chicken OVA (Abcam ab1221-100)
BSA 1% in PBS—Calbiochem #126626 1/30 dilution
Veronal Buffer+0.5 mM MgCl$_2$+0.15 mM CaCl$_2$ (VB$^{++}$)
Serum (collected with Lipirudin at 5 ug/ml final concentration)
Anti-human C3 HRP-conjugated Ab (Poly to C3-HRP Ab, Cappel 55237)
Tween-20 Wash Buffer (0.05% in PBS)
TMB (Peroxidase substrate)—1:1 mixture of BD 51-2607KC and 51-2606KC.
3M H$_2$SO$_4$
Micro-plate Reader Protocol:
1. Add 50 ul/well of 1% chicken OVA (in PBS)
2. Incubate for 2 hours at room temp
3. Remove by shaking and tapping the plate.
4. Block by adding 200 ul of 1% BSA/PBS
5. Incubate for 1 h at room temp
6. Remove by shaking and tapping the plate
7. Add 50 ul of 1/1000 dilution of Polyclonal anti-chicken OVA in 1% BSA/PBS
8. Incubate for 1 h at room temp
9. Wash twice with wash buffer
10. Add 50 ul VB$^{++}$ to wells #2 to 12
11. Add 100 ul of starting compound dilution (2× in VB$^{++}$) to well 1.
12. Serially dilute (1:2) the compound from wells 1 to 10 as follow
    a. Take 50 ul of solution from the originating well
    b. Add this to the next well
    c. Mix by pipetting several times
    d. Repeat up to well #10
Note: from well #10 remove 50 ul and discard.
13. Add 50 ul of 2× plasma dilution to wells 1 to 11
14. Incubate for 1 h
15. Wash twice with wash buffer
16. Add 50 ul of 1/1000 dilution of C3-HRP Ab in 1% BSA/PBS
17. Incubate for 1 h
18. Add 100 ul of TMB to all wells
19. Incubate for 30 min
20. Add 50 ul 3M H$_2$SO$_4$
21. Read the plate at 405 nm VB$^{++}$
Formula:

| | |
|---|---|
| Barbital | 5 mM |
| NaCl | 72.5 mM |
| MgCl$_2$ | 0.5 mM |
| CaCl$_2$ | 0.15 mM |
| pH | 7.3-7.4 |

Stock Solutions:

| Veronal Buffer (5X) | | | |
|---|---|---|---|
| | Prod # | MW | For 500 ml |
| 9 mM Sodium Barbitone | Sigma B0500 | 206.17 | 927 mg |
| 15.5 mM diethylbarbituric acid | Sigma B0375 | 184.19 | 1.42 grams |

| Mg—Cl2 (200X) | | | |
|---|---|---|---|
| | Prod # | MW | For 50 ml |
| 100 mM MgCl$_2$—6H$_2$O | Sigma M0250 | 203.30 | 1.00 gram |

| CaCl$_2$ (500x) | | | |
|---|---|---|---|
| | Prod # | MW | For 50 ml |
| 75 mM EGTA | Sigma C7902 | 147.01 | 551.28 mg |

The above assay is performed using a variety of different compstatin analogs. Percent inhibition may be normalized by considering 100% activation equal to activation occurring in the absence of compound or equal to activation occurring in the in the presence of an equal amount of an inactive variant of compstatin.

Example 5

Use of ELISA-based Assay for Alternative Complement Pathway Activation to Assess Complement Inhibiting Activity of Compstatin Analogs Materials:
Ninety six-well ELISA plate (Corning 3590)
LPS from *Salmonella* typhosa—Sigma L7136 (40 ug/ml in PBS)
BSA 1% in PBS—Calbiochem #126626 1/30 dilution
Veronal Buffer+10 mM MgCl$_2$+10 mM EGTA (VB-Mg EGTA)
Serum (collected with Lepirudin at 5 ug/ml final concentration)
Anti-human C3 HRP-conjugated Ab (Poli to C3-HRP Ab, Cappel 55237)
Tween-20 Wash Buffer (0.05% in PBS)

TMB (Peroxidase substrate)—1:1 mixture of BD 51-2607KC and 51-2606KC.

3M $H_2SO_4$

Micro-plate Reader

Protocol:
22. Add 50 ul/well of LPS at 40 ug/ml (in PBS)
23. Incubate for 2 hours at room temp
24. Remove by shaking and tapping the plate.
25. Block by adding 200 ul of 1% BSA/PBS
26. Incubate for 1 h at room temp
27. Remove by shaking and tapping the plate
28. Add 50 ul VB-Mg EGTA to wells #2 to 12
29. Add 100 ul of starting compound dilution (2× in VB-Mg EGTA) to well 1.
30. Serially dilute (1:2) the compound from wells 1 to 10 as follow
    a. Take 50 ul of solution from the originating well
    b. Add this to the next well
    c. Mix by pipetting several times
    d. Repeat up to well #10

Note: from well #10 remove 50 ul and discard.
31. Add 50 ul of 2× plasma dilution to wells 1 to 11
32. Incubate for 1 h
33. Wash twice with wash buffer
34. Add 50 ul of 1/1000 dilution of C3-HRP Ab in 1% BSA/PBS
35. Incubate for 1 h
36. Add 100 ul of TMB to all wells
37. Incubate for 10 min
38. Add 50 ul 3M $H_2SO_4$
39. Read the plate at 405 nm The above assay is performed using a variety of different compstatin analogs. Percent inhibition may be normalized by considering 100% activation equal to activation occurring in the absence of compound or equal to activation occurring in the in the presence of an equal amount of an inactive variant of compstatin.

Equivalents and Scope

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more elements or limitations found in any other claim that is dependent on the same base claim. Furthermore, where the claims recite a composition, it is to be understood that methods of administering the composition according to any of the methods disclosed herein, and methods of using the composition for any of the purposes disclosed herein are included, and methods of making the composition according to any of the methods of making disclosed herein are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. For purposes of conciseness only some of these embodiments have been specifically recited in haec verba herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

The inclusion of a "providing" step in certain methods of the invention is intended to indicate that the composition is administered to treat an eye disorder. Thus the subject will have or be at risk of an eye disorder and the composition is administered to treat the disorder, typically upon the sound recommendation of a medical or surgical practitioner, e.g., an ophthalmologist, who may or may not be the same individual who administers the composition. The invention includes embodiments in which a step of providing is not explicitly included and embodiments in which a step of providing is included. The invention also includes embodiments in which a step of identifying the subject as being at risk of or suffering from an eye disorder characterized by macular degeneration, CNV, RNV, proliferative retinopathy, diabetic retinopathy, glaucoma, ocular inflammation, or any combination of these, is included.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any particular compound), any method of administration, any eye disorder or condition or characteristic(s) thereof, or any subject characteristic(s) can be excluded from any one or more claims.

We claim:

1. A method of treating age-related macular degeneration (ARMD), comprising the step of: administering a composition comprising an effective amount of a compstatin analog to a subject suffering from ARMD.

2. The method of claim 1, wherein the compstatin analog is a compound that comprises a cyclic peptide having a core sequence of X'aa-Gln-Asp-Xaa-Gly (SEQ ID NO: 3), where X'aa and Xaa are selected from Trp and analogs of Trp.

3. The method of claim 1, wherein the compstatin analog is a compound that comprises a cyclic peptide having a core sequence of X'aa-Gln-Asp-Xaa-Gly-X"aa (SEQ ID NO: 4), where X'aa and Xaa are each independently selected from Trp and analogs of Trp and X"aa is selected from His, Ala, single methyl unbranched amino acids, Phe, Trp, and analogs of Trp.

4. The method of claim 3, wherein the peptide has a sequence of X'aa1-X'aa2-X'aa3-X'aa-Gln-Asp-Xaa-Gly-X"aa-X"aa2-X"aa3-X"aa4-X"aa5 (SEQ ID NO: 5), and X'aa1, X'aa2, X'aa3, X"aa2, X"aa3-X"aa4, and X"aa5 are identical to the amino acids at the corresponding positions in compstatin.

5. The method of claim 1, wherein the compstatin analog is a compound that comprises a cyclic peptide having a sequence of X'aa1-X'aa2-X'aa3-X'aa4-Gln-Asp-Xaa-Gly-X"aa1-X"aa2-X"aa3-X"aa4-X"aa- 5 (SEQ ID NO: 5), where X'aa4 and Xaa are selected from Trp and analogs of Trp, wherein X'aa1, X'aa2, X'aa3, X"aa1, X"aa2, X"aa3, X"aa4, and X"aa5 are independently selected from among amino acids and amino acid analogs, and the peptide is cyclized via a bond between X'aa2 and X"aa4.

6. The method of claim 1, wherein the compstatin analog is a compound that comprises a cyclic peptide having a sequence: Xaa1-Cys-Val-Xaa2-Gln-Asp-Xaa2*-Gly-Xaa3-His-Arg-Cys-Xaa4 (SEQ ID NO: 6); wherein: Xaa1 is Ile, Val, Leu, $B_1$-Ile, $B_1$-Val, $B_1$-Leu or a dipeptide comprising Gly-Ile or $B_1$-Gly-Ile, and $B_1$ represents a first blocking moiety; Xaa2 and Xaa2* are independently selected from Trp and analogs of Trp; Xaa3 is His, Ala or an analog of Ala, Phe, Trp, or an analog of Trp; Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B_2$; and the two Cys residues are joined by a disulfide bond.

7. The method of claim 6, wherein the peptide is acetylated at the N-terminus, amidated at the C-terminus, or both acetylated at the N-terminus and amidated at the C-terminus.

8. The method of claim 6, wherein Xaa1 is Ile, Val, Leu, Ac-Ile, Ac-Val, Ac-Leu or a dipeptide comprising Gly-Ile or Ac-Gly-Ile; Xaa2 and Xaa2* are independently selected from Trp and analogs of Trp; Xaa3 is His, Ala or an analog of Ala, Phe, Trp, or an analog of Trp; Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by —NH$_2$.

9. The method of claim 6, wherein Xaa2 is an analog of Trp having increased hydrophobic character relative to Trp.

10. The method of claim 6, wherein Xaa2 is an analog of Trp comprising a substituted or unsubstituted bicyclic aromatic ring component or two or more substituted or unsubstituted monocyclic aromatic ring components.

11. The method of claim 1, wherein the composition is administered intravitreally.

12. The method of claim 1, wherein the compstatin analog is a compound that comprises a cyclic peptide comprising a cyclic portion 11 amino acids in length, wherein the sequence of the peptide is at least 50% identical to the sequence of compstatin (SEQ ID NO: 8) or to the sequence of a compstatin analog that has higher activity than compstatin.

13. The method of claim 12, wherein the peptide comprises at least one non-standard amino acid.

14. The method of claim 13, wherein at least one non-standard amino acid is a singly or multiply halogenated amino acid, N-alkyl amino acid, or aromatic amino acid.

15. The method of claim 1, wherein the compstatin analog is a compound that comprises or consists of a sequence that is obtained by making 1, 2, 3, or 4 substitutions in the sequence of compstatin, wherein the peptide is cyclized via a bond between amino acids at positions that correspond to position 2 and position 12 of compstatin.

16. The method of claim 15, wherein 1, 2, 3, or 4 amino acids in the sequence of compstatin is replaced by a non-standard amino acid.

17. The method of claim 16, wherein at least one non-standard amino acid is a singly or multiply halogenated amino acid, N-alkyl amino acid, or aromatic amino acid.

18. The method of claim 1, wherein the compstatin analog binds to substantially the same region of human C3 as does compstatin and has a C3 inhibitory activity at least 10-fold as great as that of compstatin.

19. The method of claim 1, wherein the composition is locally administered to the eye or in the vicinity of the eye.

* * * * *

SEQUENCE LISTING

<160> NUMBER OF SEQ ID NOS: 32

<210> SEQ ID NO 1
<211> LENGTH: 6
<212> TYPE: PRT
<213> ORGANISM: Artificial Sequence
<220> FEATURE:
<223> OTHER INFORMATION: Synthetic Gap Peptide
<220> FEATURE:
<221> NAME/KEY: NON_CONS
<222> LOCATION: (3)..(4)

<400> SEQUENCE: 1

Ala Lys Leu Ser Ile Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Any amino acid or amino acid analog
<220> FEATURE:
<221> NAME/KEY: MISC_FEATURE
<222> LOCATION: (4)..(4)
<223> OTHER INFORMATION: Xaa =Trp or Trp analog
<220> FEATURE:
<221> NAME/KEY: MISC_FEATURE
<222> LOCATION: (6)..(6)
<223> OTHER INFORMATION: Xaa = Any amino acid or amino acid analog

<400> SEQUENCE: 2

Xaa Gln Asp Xaa Gly Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Trp or analog of Trp
<220> FEATURE:
<221> NAME/KEY: MISC_FEATURE
<222> LOCATION: (4)..(4)
<223> OTHER INFORMATION: Xaa = Trp or analog of Trp

<400> SEQUENCE: 3

Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Trp or analog of trp
<220> FEATURE:
<221> NAME/KEY: MISC_FEATURE
<222> LOCATION: (4)..(4)
<223> OTHER INFORMATION: Xaa = Trp or analog of Trp

```
<220> FEATURE:
<221> NAME/KEY: MISC_FEATURE
<222> LOCATION: (6)..(6)
<223> OTHER INFORMATION: Xaa = His, Ala, analogs of Ala, Phe, and Trp

<400> SEQUENCE: 4

Xaa Gln Asp Xaa Gly Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Ile, Val, Leu, B1 - Ile, B1-Val, B1-Leu
    or a dipeptide comprising Gly-Ile or B1-Gly-Ile, wherein B1
    represents a blocking moiety
<220> FEATURE:
<221> NAME/KEY: MISC_FEATURE
<222> LOCATION: (4)..(4)
<223> OTHER INFORMATION: Xaa = Trp or analog of Trp
<220> FEATURE:
<221> NAME/KEY: MISC_FEATURE
<222> LOCATION: (7)..(7)
<223> OTHER INFORMATION: Xaa = Trp or analog of Trp
<220> FEATURE:
<221> NAME/KEY: MISC_FEATURE
<222> LOCATION: (9)..(9)
<223> OTHER INFORMATION: Xaa = His, Ala or analog of Ala, Phe, Trp or
    analog of Trp
<220> FEATURE:
<221> NAME/KEY: MISC_FEATURE
<222> LOCATION: (13)..(13)
<223> OTHER INFORMATION: Xaa = L-Thr, D-Thr, Ile, Val, Gly, dipeptide
    selected from Thr-Ala and Thr-Asn, or  tripeptide comprising
    Thr-Ala-Asn, wherein a carboxy terminal -OH of any of the L-Thr,
    D-Thr, Ile, Val, Gly, Ala, or Asn optionally is replaced by a
    second blocking

<400> SEQUENCE: 6

Xaa Cys Val Xaa Gln Asp Xaa Gly Xaa His Arg Cys Xaa
1               5                   10

<210> SEQ ID NO 7
<211> LENGTH: 13
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ile, Val, Leu, Ac-Ile, Ac-Val, Ac-Leu or
      a dipeptide comprising Gly-Ile or Ac-Gly-Ile
<220> FEATURE:
<221> NAME/KEY: MISC_FEATURE
<222> LOCATION: (4)..(4)
<223> OTHER INFORMATION: Xaa = Trp or analog of Trp
<220> FEATURE:
<221> NAME/KEY: MISC_FEATURE
<222> LOCATION: (7)..(7)
<223> OTHER INFORMATION: Xaa = Trp or analog of Trp
<220> FEATURE:
<221> NAME/KEY: MISC_FEATURE
<222> LOCATION: (9)..(9)
<223> OTHER INFORMATION: Xaa = His, Ala or an analog of Ala, Phe, Trp,
      or an analog of Trp
<220> FEATURE:
<221> NAME/KEY: MISC_FEATURE
<222> LOCATION: (13)..(13)
<223> OTHER INFORMATION: Xaa =  L-Thr, D-Thr, Ile, Val, Gly, a dipeptide
      selected from Thr-Ala and Thr-Asn, or a tripeptide comprising Thr-
      Ala-Asn, wherein a carboxy terminal -OH of any of L-Thr, D-Thr,
      Ile, Val, Gly, Ala, or Asn optionally is replaced by -NH2

<400> SEQUENCE: 7

Xaa Cys Val Xaa Gln Asp Xaa Gly Xaa Gly Arg Cys Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: AMIDATION

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 10

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 2-naphthylalanine
<220> FEATURE:
<221> NAME/KEY: MOD_RES
<222> LOCATION: (13)..(13)
<223> OTHER INFORMATION: AMIDATION

<400> SEQUENCE: 14

Ile Cys Val Xaa Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 2-naphthylalanine

<400> SEQUENCE: 15

Ile Cys Val Xaa Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 1-naphthylalanine

<400> SEQUENCE: 16

Ile Cys Val Xaa Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 2-indanylglycine carboxylica acid
<220> FEATURE:
<221> NAME/KEY: MOD_RES
<222> LOCATION: (13)..(13)
<223> OTHER INFORMATION: AMIDATION
```

<400> SEQUENCE: 17

Ile Cys Val Xaa Gln Asp Trp Gly Ala His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 2-indanylglycine carboxylic acid

<400> SEQUENCE: 18

Ile Cys Val Xaa Gln Asp Trp Gly Ala His Arg Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = dihydrotryptophan

<400> SEQUENCE: 19

Ile Cys Val Xaa Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 4-benzyol-L-phenylalanine

<400> SEQUENCE: 20

Ile Cys Val Xaa Gln Asp Trp Gly Ala His Arg Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 4-benzoyl-L-phenylalanine
<220> FEATURE:
<221> NAME/KEY: MOD_RES
<222> LOCATION: (13)..(13)
<223> OTHER INFORMATION: AMIDATION

<400> SEQUENCE: 21

Ile Cys Val Xaa Gln Asp Trp Gly Ala His Arg Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Bta

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Bta
<220> FEATURE:
<221> NAME/KEY: MOD_RES
<222> LOCATION: (13)..(13)
<223> OTHER INFORMATION: AMIDATION

<400> SEQUENCE: 23

Ile Cys Val Xaa Gln Asp Trp Gly Ala His Arg Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (9)..(9)
<223> OTHER INFORMATION: Xaa = 2-alpha-aminobutyric acid
<220> FEATURE:
<221> NAME/KEY: MOD_RES
<222> LOCATION: (13)..(13)
```

```
<223> OTHER INFORMATION: AMIDATION

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 25

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 5-fluoro-L-tryptophan
<220> FEATURE:
<221> NAME/KEY: MOD_RES
<222> LOCATION: (13)..(13)
<223> OTHER INFORMATION: AMIDATION

<400> SEQUENCE: 26

Ile Cys Val Xaa Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 5-methyl-L-tryptophan
<220> FEATURE:
<221> NAME/KEY: MOD_RES
<222> LOCATION: (13)..(13)
<223> OTHER INFORMATION: AMIDATION

<400> SEQUENCE: 27

Ile Cys Val Xaa Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 1-methyl-tryptophan
<220> FEATURE:
<221> NAME/KEY: MISC_FEATURE
<222> LOCATION: (4)..(4)
<223> OTHER INFORMATION: Xaa = 1-methyltryptophan
<220> FEATURE:
<221> NAME/KEY: MOD_RES
<222> LOCATION: (13)..(13)
<223> OTHER INFORMATION: AMIDATION

<400> SEQUENCE: 28

Ile Cys Val Xaa Gln Asp Trp Gly Ala His Arg Cys Thr
 1               5                  10

<210> SEQ ID NO 29
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: Xaa = 5-fluoro-L-tryptophan
<220> FEATURE:
<221> NAME/KEY: MOD_RES
<222> LOCATION: (13)..(13)
<223> OTHER INFORMATION: AMIDATION

<400> SEQUENCE: 29

Ile Cys Val Trp Gln Asp Xaa Gly Ala His Arg Cys Thr
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 5-fluoro-L-tryptopham
<220> FEATURE:
<221> NAME/KEY: MISC_FEATURE
<222> LOCATION: (7)..(7)
<223> OTHER INFORMATION: Xaa = 5-fluoro-L-tryptopham
<220> FEATURE:
<221> NAME/KEY: MOD_RES
<222> LOCATION: (13)..(13)
<223> OTHER INFORMATION: AMIDATION

<400> SEQUENCE: 30

Ile Cys Val Xaa Gln Asp Xaa Gly Ala His Arg Cys Thr
 1               5                  10

<210> SEQ ID NO 31
<211> LENGTH: 13
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 5-methyl-L-tryptophan
<220> FEATURE:
<221> NAME/KEY: MISC_FEATURE
<222> LOCATION: (7)..(7)
<223> OTHER INFORMATION: Xaa = 5-fluoro-L-tryptophan
<220> FEATURE:
<221> NAME/KEY: MOD_RES
<222> LOCATION: (13)..(13)
<223> OTHER INFORMATION: AMIDATION

<400> SEQUENCE: 31

Ile Cys Val Xaa Gln Asp Xaa Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = 1-methyltryptophan
<220> FEATURE:
<221> NAME/KEY: MISC_FEATURE
<222> LOCATION: (7)..(7)
<223> OTHER INFORMATION: Xaa = 5-flouro-L-tryptophan
<220> FEATURE:
<221> NAME/KEY: MOD_RES
<222> LOCATION: (13)..(13)
<223> OTHER INFORMATION: AMIDATION

<400> SEQUENCE: 32

Ile Cys Val Xaa Gln Asp Xaa Gly Ala His Arg Cys Thr
1               5                   10
```